United States Patent
Riviere et al.

(10) Patent No.: US 11,673,961 B2
(45) Date of Patent: Jun. 13, 2023

(54) ANTI-CD20 ANTIBODY AND USES THEREOF

(71) Applicant: Memorial Sloan Kettering Cancer Center, New York, NY (US)

(72) Inventors: Isabelle Riviere, New York, NY (US); Ouathek Ouerfelli, New York, NY (US); Xiuyan Wang, New York, NY (US); Frances Weis-Garcia, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 167 days.

(21) Appl. No.: 16/970,805

(22) PCT Filed: Feb. 19, 2019

(86) PCT No.: PCT/US2019/018535
§ 371 (c)(1),
(2) Date: Aug. 18, 2020

(87) PCT Pub. No.: WO2019/164821
PCT Pub. Date: Aug. 29, 2019

(65) Prior Publication Data
US 2021/0107987 A1    Apr. 15, 2021

Related U.S. Application Data

(60) Provisional application No. 62/633,034, filed on Feb. 20, 2018.

(51) Int. Cl.
| | | |
|---|---|---|
| C07K 16/28 | (2006.01) | |
| A61P 35/00 | (2006.01) | |
| A61K 35/17 | (2015.01) | |
| C07K 14/725 | (2006.01) | |
| C07K 14/705 | (2006.01) | |
| G01N 33/574 | (2006.01) | |

(52) U.S. Cl.
CPC .......... *C07K 16/2887* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 14/70596* (2013.01); *G01N 33/57492* (2013.01); *C07K 2317/622* (2013.01); *C07K 2319/02* (2013.01); *C07K 2319/03* (2013.01); *G01N 2333/70596* (2013.01)

(58) Field of Classification Search
None
See application file for complete search history.

(56) References Cited

FOREIGN PATENT DOCUMENTS

| JP | 2016-208934 A2 | 12/2016 | |
|---|---|---|---|
| WO | WO-2010/117448 A2 | 10/2010 | |
| WO | WO-2013054127 A1 * | 4/2013 | ............ A61P 17/00 |
| WO | WO-2017011316 A1 * | 1/2017 | ............ A61K 35/17 |

OTHER PUBLICATIONS

Ernst J. A. et al. Biochemistry 44: 15150 (2005)) (Year: 2005).*
Almagro & Fransson, Frontiers in Bioscience 2008; 13:1619-33 (Year: 2008).*
International Search Report and Written Opinion, PCT/US2019/018535, Memorial Sloan Kettering Cancer Center (dated Jul. 5, 2019).
UniProtKB Accession No. A0A026WD16_OOCBI "Glycerate kinase", Jul. 9, 2014 (online]. [Retrieved on Jun. 17, 2019]. Retrieved from the internet: <URL:https://www.uniprot.org/uniprot/AOA026WD 16> Entire document.
UniProtKB Accession No. A0A1X4NOU5_9PROT "Glycerol-3-phosphate dehydrogenase", Jul. 5, 2017 [online]. [Retrieved on Jun. 17, 2019]. Retrieved from the internet: <URL: https://www.uniprot.org/uniprot/AOA 1 X4N0U5> Entire document.

* cited by examiner

*Primary Examiner* — Peter J Reddig
(74) *Attorney, Agent, or Firm* — Foley & Lardner LLP

(57) ABSTRACT

Provided herein are anti-CD20 antibodies and uses thereof for treatment and diagnosis. Also provided are CD20 antigens for the production of anti-CD20 antibodies and methods of generating anti-CD20 antibodies using the CD20 antigens.

20 Claims, 26 Drawing Sheets
Specification includes a Sequence Listing.

PRIOR ART

FIG. 3

| | |
|---|---|
| Canine: | NITISHFFKMENLNLIKAPMPYVDIHNCDPANPSEKNSLSIQYCGS |
| Human: | NIKISHFLKMESLNFIRAHTPYINIYNCEPANPSEKNSPSTQYCYS |
| Mouse: | NMTLSHFLKMRSLNFIRAHTPYINIYNCEPANPSEKNSPSTQYCNS |

FIG. 10
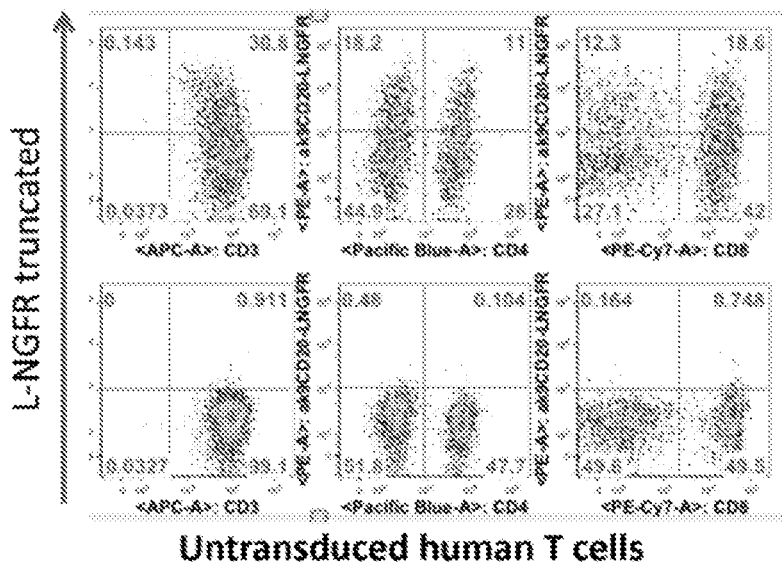
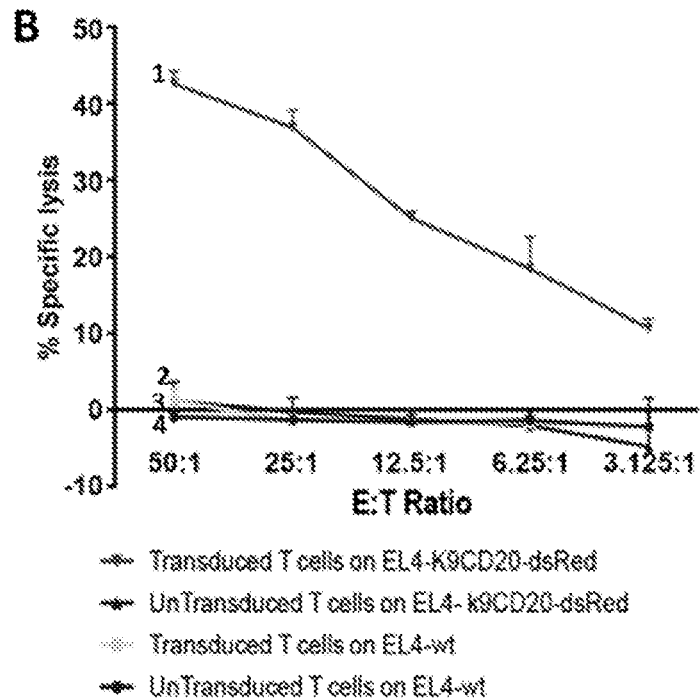

FIG. 13

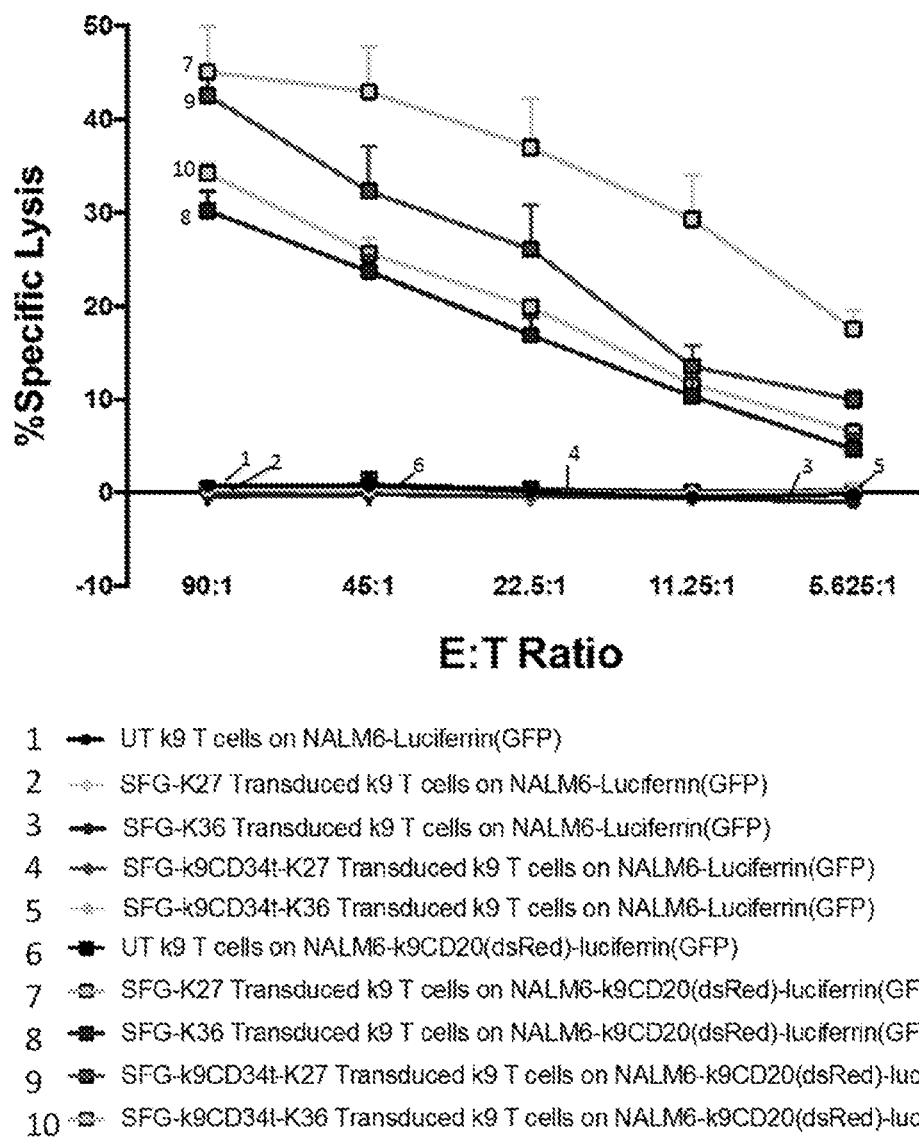

1   →— UT k9 T cells on NALM6-Luciferrin(GFP)
2   ⋯◇⋯ SFG-K27 Transduced k9 T cells on NALM6-Luciferrin(GFP)
3   →— SFG-K36 Transduced k9 T cells on NALM6-Luciferrin(GFP)
4   —▽— SFG-k9CD34t-K27 Transduced k9 T cells on NALM6-Luciferrin(GFP)
5   ⋯△⋯ SFG-k9CD34t-K36 Transduced k9 T cells on NALM6-Luciferrin(GFP)
6   —■— UT k9 T cells on NALM6-k9CD20(dsRed)-luciferrin(GFP)
7   ⋯□⋯ SFG-K27 Transduced k9 T cells on NALM6-k9CD20(dsRed)-luciferrin(GFP)
8   —■— SFG-K36 Transduced k9 T cells on NALM6-k9CD20(dsRed)-luciferrin(GFP)
9   —■— SFG-k9CD34t-K27 Transduced k9 T cells on NALM6-k9CD20(dsRed)-luciferrin(GFP)
10 ⋯□⋯ SFG-k9CD34t-K36 Transduced k9 T cells on NALM6-k9CD20(dsRed)-luciferrin(GFP)

FIG. 14
A.
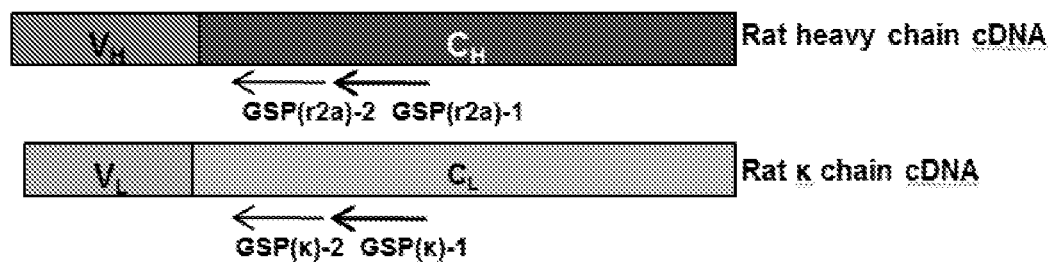
B.
C.
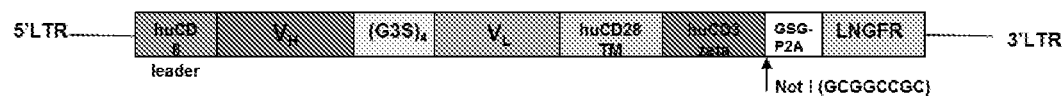
D.
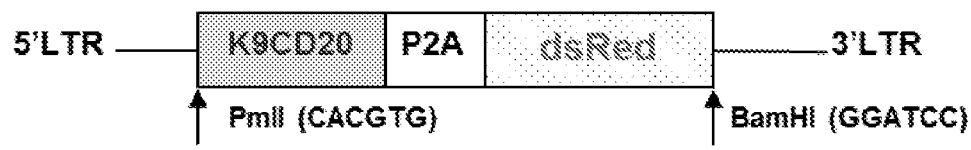
E.
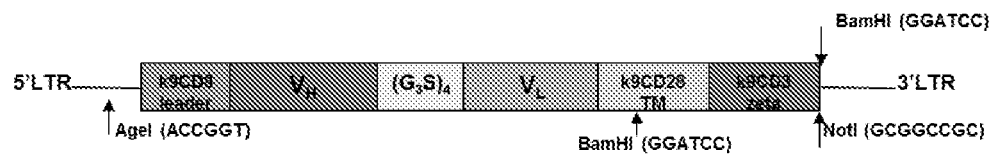

FIG. 14 (cont'd)
F.
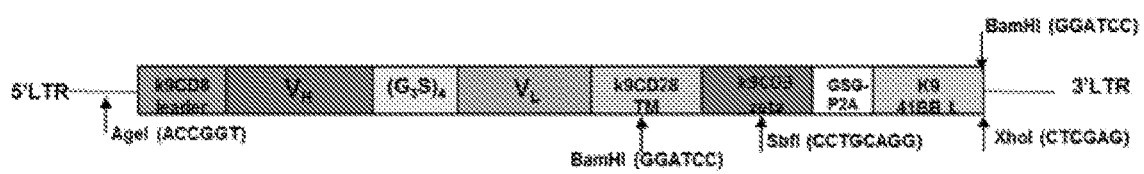
G.
H.
I.
J.
K.
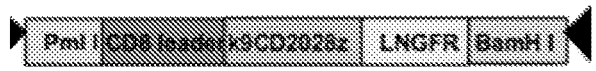

FIG. 24
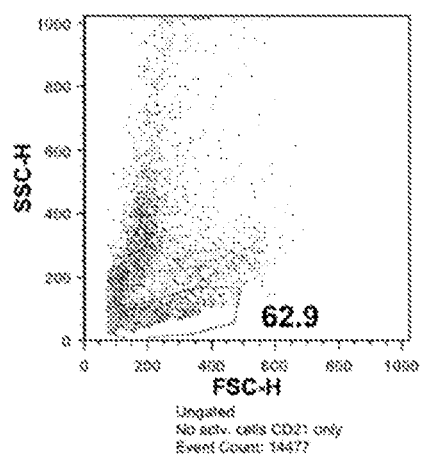
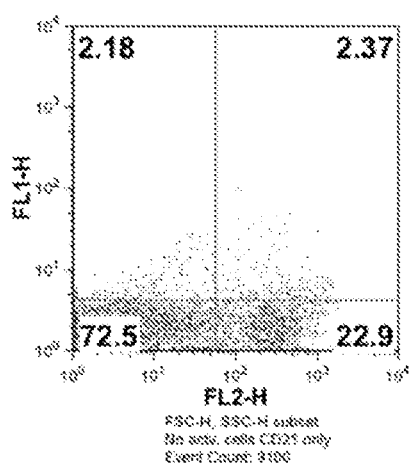
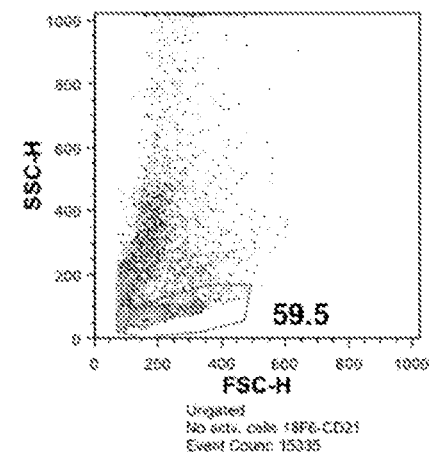
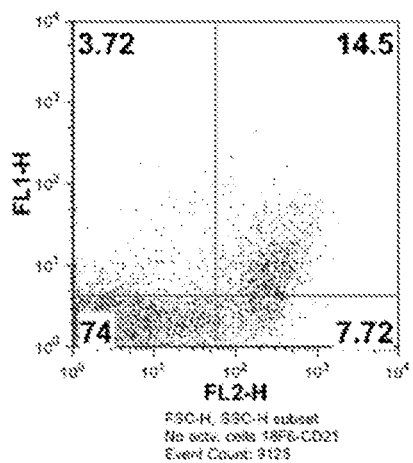

SEQUENCE LISTING

```
<160> NUMBER OF SEQ ID NOS: 62

<210> SEQ ID NO 1
<211> LENGTH: 46
<212> TYPE: PRT
<213> ORGANISM: Canis sp.

<400> SEQUENCE: 1

Asn Ile Thr Ile Ser His Phe Phe Lys Met Glu Asn Leu Asn Leu Ile
1               5                   10                  15

Lys Ala Pro Met Pro Tyr Val Asp Ile His Asn Cys Asp Pro Ala Asn
            20                  25                  30

Pro Ser Glu Lys Asn Ser Leu Ser Ile Gln Tyr Cys Gly Ser
        35                  40                  45

<210> SEQ ID NO 2
<211> LENGTH: 46
<212> TYPE: PRT
<213> ORGANISM: Homo sapiens

<400> SEQUENCE: 2

Asn Ile Lys Ile Ser His Phe Leu Lys Met Glu Ser Leu Asn Phe Ile
1               5                   10                  15

Arg Ala His Thr Pro Tyr Ile Asn Ile Tyr Asn Cys Glu Pro Ala Asn
            20                  25                  30
```

Pro Ser Glu Lys Asn Ser Pro Ser Thr Gln Tyr Cys Tyr Ser
        35                  40                  45

<210> SEQ ID NO 3
<211> LENGTH: 46
<212> TYPE: PRT
<213> ORGANISM: Mus sp.

<400> SEQUENCE: 3

Asn Met Thr Leu Ser His Phe Leu Lys Met Arg Ser Leu Asn Phe Ile
1               5                   10                  15

Arg Ala His Thr Pro Tyr Ile Asn Ile Tyr Asn Cys Glu Pro Ala Asn
            20                  25                  30

Pro Ser Glu Lys Asn Ser Pro Ser Thr Gln Tyr Cys Asn Ser
        35                  40                  45

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Lys Pro Gly Thr
1               5                   10                  15

Ser Leu Lys Leu Ser Cys Val Ala Ser Gly Phe Ser Phe Ser Asp Cys
            20                  25                  30

Trp Met Ser Trp Ala Arg Gln Thr Pro Gly Lys Thr Met Glu Trp Ile
        35                  40                  45

Gly Asp Ile Lys Tyr Asp Gly Arg Ala Thr Asn Tyr Ala Pro Ser Leu
    50                  55                  60

Gln Thr Arg Phe Ile Ile Ser Arg Asp Asn Ala Lys Ser Thr Leu Tyr
65                  70                  75                  80

Leu Gln Met Thr Asn Val Arg Ser Glu Asp Thr Ala Thr Tyr Tyr Cys
                85                  90                  95

Thr Gly Asn His Tyr Gly Gly Tyr Thr Leu Arg Phe Ala Tyr Trp Gly
            100                 105                 110

Gln Gly Thr Leu Val Thr Val Ser Ser
        115                 120

<210> SEQ ID NO 5
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaagtacagc ttgtggagtc tggaggaggt ttggtgaaac ctgggacttc tctgaaactc      60
tcttgtgtag cctcgggatt cagtttcagt gactgctgga tgagctgggc tcgccagact     120
cctggaaaga ccatggagtg gattggagat attaaatatg atggcagggc cacaaactat     180
gcaccttccc ttcagactcg attcataatt ccagagaca atgccaagag taccctgtac      240
ctgcagatga ccaatgtgag atctgaggac acagccactt attattgtac tgggaaccac     300
tacggaggct ataccctccg gtttgcttac tggggccaag gcactctggt cactgtctct     360

```
<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Val Val Leu Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Asn Gly Asn Thr Tyr Leu His Trp Phe Leu Gln Arg Pro Gly Gln Ser
        35                  40                  45

Pro Gln Leu Leu Ile Tyr Leu Val Ser Arg Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Val Gln Gly
                85                  90                  95

Thr His Ala Pro Pro Thr Phe Gly Gly Gly Ala Gly Thr Asn Leu
            100                 105                 110

Glu Leu Lys Arg Ala
        115

<210> SEQ ID NO 7
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gatgttgtgc tgacccagac tccacccact ttatcggcta ccattggaca atcagtctcc      60
atctcttgca ggtcaagtca gagtctctta catagtaatg gaaacaccta tttacattgg     120
ttcctacaga ggccaggcca atctccacag cttctaattt acttggtttc cagactggaa     180 tctgggtcc ccaacaggtt cagtggcagt gggtcaggaa ctgatttcac actcaaaatc      240
agtggagtag aggctgagga tttgggagtt tattactgtg ttcaaggtac ccatgctcct     300
ccgacgttcg gtggcggcgg agctgggacc aacctggagc tgaaacgggc t              351

<210> SEQ ID NO 8
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Lys Pro Gly Thr
1               5                   10                  15

Ser Leu Lys Leu Ser Cys Val Ala Ser Gly Phe Ser Phe Ser Asp Cys
            20                  25                  30

Trp Met Ser Trp Ala Arg Gln Thr Pro Gly Lys Thr Met Glu Trp Ile
        35                  40                  45
``` tca                                                                    363

Gly Asp Ile Lys Tyr Asp Gly Arg Ala Thr Asn Tyr Ala Pro Ser Leu
            50                  55                  60

Gln Thr Arg Phe Ile Ile Ser Arg Asp Asn Ala Lys Ser Thr Leu Tyr
65                  70                  75                  80

Leu Gln Met Thr Asn Val Arg Ser Glu Asp Thr Ala Thr Tyr Tyr Cys
                85                  90                  95

Thr Gly Asn His Tyr Gly Gly Tyr Thr Leu Arg Phe Ala Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Val Val Leu Thr Gln Thr Pro
    130                 135                 140

Pro Thr Leu Ser Ala Thr Ile Gly Gln Ser Val Ser Ile Ser Cys Arg
145                 150                 155                 160

Ser Ser Gln Ser Leu Leu His Ser Asn Gly Asn Thr Tyr Leu His Trp
                165                 170                 175

Phe Leu Gln Arg Pro Gly Gln Ser Pro Gln Leu Leu Ile Tyr Leu Val
            180                 185                 190

Ser Arg Leu Glu Ser Gly Val Pro Asn Arg Phe Ser Gly Ser Gly Ser
        195                 200                 205

Gly Thr Asp Phe Thr Leu Lys Ile Ser Gly Val Glu Ala Glu Asp Leu
    210                 215                 220

Gly Val Tyr Tyr Cys Val Gln Gly Thr His Ala Pro Pro Thr Phe Gly
225                 230                 235                 240

Gly Gly Gly Ala Gly Thr Asn Leu Glu Leu Lys Arg Ala
                245                 250

<210> SEQ ID NO 9
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaagtacagc ttgtggagtc tggaggaggt ttggtgaaac ctgggacttc tctgaaactc      60
tcttgtgtag cctcgggatt cagtttcagt gactgctgga tgagctgggc tcgccagact     120
cctggaaaga ccatggagtg gattggagat attaaatatg atggcagggc cacaaactat     180
gcaccttccc ttcagactcg attcataatt ccagagaca atgccaagag taccctgtac      240
ctgcagatga ccaatgtgag atctgaggac acagccactt attattgtac tgggaaccac     300 tacgaggct ataccctccg gtttgcttac tggggccaag gcactctggt cactgtctct      360
tcaggtggag gtggatcagg tggaggtgga tctggtggag gtggatctga tgttgtgctg     420
acccagactc cacccacttt atcggctacc attggacaat cagtctccat ctcttgcagg     480
tcaagtcaga gtctcttaca tagtaatgga acacctatt tacattggtt cctacagagg      540
ccaggccaat ctccacagct tctaatttac ttggtttcca gactggaatc tggggtcccc     600
aacaggttca gtggcagtgg gtcaggaact gatttcacac tcaaaatcag tggagtagag     660
gctgaggatt tgggagtttta ttactgtgtt caaggtaccc atgctcctcc gacgttcggt     720
ggcggcggag ctgggaccaa cctggagctg aaacgggct                             759

<210> SEQ ID NO 10

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggtggaggtg gatcaggtgg aggtggatct ggtggaggtg gatct              45

<210> SEQ ID NO 12
<211> LENGTH: 21
<212> TYPE: PRT
<213> ORGANISM: Canis sp.

<400> SEQUENCE: 12

Met Ala Ser Arg Val Thr Ala Leu Leu Leu Pro Leu Ala Leu Leu Leu
1               5                   10                  15

Arg Ala Ala Ala Ala
            20

<210> SEQ ID NO 13
<211> LENGTH: 63
<212> TYPE: DNA
<213> ORGANISM: Canis sp.

<400> SEQUENCE: 13
atggcctctc gggtgaccgc cctgctcctg ccgctggccc tgctgctccg tgccgcggcg   60
gcc                                                                63

<210> SEQ ID NO 14
<211> LENGTH: 107
<212> TYPE: PRT
<213> ORGANISM: Canis sp.

<400> SEQUENCE: 14

Ile Glu Val Met Tyr Pro Pro Pro Tyr Ile Gly Asn Glu Lys Ser Asn
1               5                   10                  15

Gly Thr Ile Ile His Val Lys Glu Lys His Leu Cys Pro Asp Glu Leu
            20                  25                  30

Phe Pro Asp Ser Ser Lys Pro Phe Trp Ala Leu Val Val Val Gly Ala
        35                  40                  45

Val Leu Val Phe Tyr Ser Leu Leu Val Thr Val Ala Leu Cys Ala Tyr
    50                  55                  60

Trp Ile Lys Ser Lys Ser Ser Arg Ile Leu Gln Ser Asp Tyr Met Asn
65                  70                  75                  80

Met Thr Pro Arg Arg Pro Gly Pro Thr Arg Arg His Tyr Gln Pro Tyr
                85                  90                  95

Ala Pro Ala Arg Asp Phe Ala Ala Tyr Arg Ser
            100                 105
```

<210> SEQ ID NO 15
<211> LENGTH: 321
<212> TYPE: DNA
<213> ORGANISM: Canis sp.

<400> SEQUENCE: 15
attgaggtca tgtatccacc tccttacatt ggcaatgaga agagcaatgg gaccattatc    60
catgtgaaag aaaaacatct ttgtccagat gagctgtttc ctgattcttc taagccattt   120
tgggcactgg tggtggttgg tgcagtccta gttttctata gcttgctagt aacagtggct   180
ctttgtgcct actggataaa gagtaagagt agcaggatcc ttcagagtga ctacatgaac   240 atgaccccc ggaggccggg gcccacccga aggcactacc aaccctatgc cccagcacgc   300
gactttgcag cataccgctc c                                              321

<210> SEQ ID NO 16
<211> LENGTH: 121
<212> TYPE: PRT
<213> ORGANISM: Canis sp.

<400> SEQUENCE: 16

Arg Leu Arg Ser Thr Arg Pro Ala Ala Pro Gly Ala Pro Arg Gly
 1               5                  10                  15

Pro Gly Gln Ser Pro Arg Ser Ser Arg Leu Leu Gln Glu Leu Asn
                20                  25                  30

Leu Arg Gly Arg Glu Glu Tyr Glu Val Leu Asp Lys Arg Arg Gly Leu
            35                  40                  45

Asp Pro Glu Met Gly Gly Lys Gln Arg Lys Arg Asn Pro Gln Glu Val
        50                  55                  60

Val Tyr Asn Ala Leu Gln Lys Asp Lys Met Ala Glu Ala Tyr Ser Glu
 65                  70                  75                  80

Ile Gly Ile Lys Ser Glu Asn Gln Arg Arg Gly Lys Gly His Asp
                85                  90                  95

Gly Leu Tyr Gln Gly Leu Ser Thr Ala Thr Lys Asp Thr Tyr Asp Ala
                100                 105                 110

Leu His Met Gln Ala Leu Pro Pro Arg
            115                 120

<210> SEQ ID NO 17
<211> LENGTH: 363
<212> TYPE: DNA
<213> ORGANISM: Canis sp.

<400> SEQUENCE: 17
cggctccgct ccaccaggcc cgcggctccc ccgggcgccc cacggggtcc aggccagagc    60
ccccgacggt cttcccgcct cctgcaggag ctcaatctgc gaggaagaga ggagtacgag   120
gttttggata agagacgcgg cctggacccg gagatgggag aaagcagag gaagaggaac   180 cctcaggagg tcgtgtacaa tgcactgcag aaagacaaga tggcagaggc ctacagtgag   240
attgggataa aaagcgagaa ccagcgtcgg agagggaagg gcatgatgg cctttaccag   300 gggctcagca cggccaccaa ggacacctat gatgccctcc acatgcaggc cctgcctcct   360
cgc                                                                  363

<210> SEQ ID NO 18
<211> LENGTH: 254
<212> TYPE: PRT

<213> ORGANISM: Canis sp.

<400> SEQUENCE: 18

```
Met Arg Pro Arg Ser Asp Ala Ala Pro Asp Pro Glu Ala Pro Arg Pro
1               5                   10                  15
Pro Ala Pro Pro Gly Arg Ala Cys Ser Pro Leu Pro Trp Ala Leu Ser
                20                  25                  30
Ala Ala Met Leu Leu Leu Val Gly Thr Cys Ala Ala Cys Ala Leu Arg
            35                  40                  45
Ala Trp Val Val Pro Gly Pro Arg Pro Pro Ala Leu Pro Ala Leu Pro
        50                  55                  60
Ala Pro Leu Pro Asp Ala Gly Ala Arg Leu Pro Asp Ser Pro Gln Ala
65                  70                  75                  80
Val Phe Ala Gln Leu Val Ala Arg Asp Val Gln Leu Lys Glu Gly Pro
                85                  90                  95
Leu Arg Trp Tyr Ser Asp Pro Gly Leu Ala Gly Val Phe Leu Gly Pro
                100                 105                 110
Gly Leu Ser Tyr Asp Gln His Thr Arg Glu Leu Met Val Val Glu Pro
            115                 120                 125
Gly Leu Tyr Tyr Val Phe Leu His Leu Lys Leu Gln Arg Val Met Ser
        130                 135                 140
Ser Thr Gly Ser Gly Ser Val Ser Ala Ala Leu His Leu Gln Pro Leu
145                 150                 155                 160
Gly Thr Glu Ala Ala Ala Leu Asp Leu Thr Leu Asp Leu Pro Pro Pro
                165                 170                 175
Ser Ser Glu Ala Arg Asp Ser Ala Ala Gly Phe Arg Gly Ser Leu Leu
                180                 185                 190
His Leu Asp Ala Gly Gln Arg Leu Arg Val His Leu Arg Ala Glu Ala
            195                 200                 205
Gly Ala His Pro Ala Trp Gln Leu Ala Gln Gly Ala Thr Ile Leu Gly
        210                 215                 220
Leu Phe Arg Val Ala Thr Lys Val Pro Thr Gly Leu Pro Ser Ser Trp
225                 230                 235                 240
Pro Met Asp Thr Gly Pro Gly Ser Pro Pro Leu Asp Gly Glu
                245                 250
```

<210> SEQ ID NO 19
<211> LENGTH: 762
<212> TYPE: DNA
<213> ORGANISM: Canis sp.

<400> SEQUENCE: 19

```
atgcgccccc gcagcgacgc cgccccggac cccgaggccc cgcggccgcc cgcgccccc       60 ggccgcgcct gcagcccgct gccctgggcg ctgagcgccg cgatgctgct gctcgtcggc      120
acctgcgccg cctgcgcgct ccgcgcctgg gtggtccccg gccccgcc ccccgcgctc       180 cccgcgctcc ccgcgcccct gccggacgcc ggcgcccgcc tccccgactc cccgcaggcc     240
gtgttcgcgc agctggtggc ccgagatgta cagctgaagg aaggacccct gcgctggtac     300
agtgacccgg gctggcagg tgtattcctg gggccgggcc tgagttatga ccagcacact     360
cgggagctga tggtggtgga acccgggctc tactatgttt tcttgcacct gaagctgcag    420
cgggtaatgt ccagcacggg ctccggctct gtctctgctg ccctgcacct gcagccactt    480
ggcaccgagg ctgcagccct ggacctgacc ttgacctgc ctccaccatc ctcggaggcc     540
cgtgactcag cagctggttt ccggggcagc ctgctgcacc tggacgcagg ccagcgcctc    600
```

```
cgtgttcact tgcgagctga ggcaggggcc caccctgcct ggcagctggc acaaggtgcc    660
acgatcttgg gcctcttcag agtggccacc aaagtcccca ctggactccc ctcgtcatgg    720
cccatggaca cggggcctgg gtccccgccc ctggatggag aa                       762
```

<210> SEQ ID NO 20
<211> LENGTH: 23
<212> TYPE: PRT
<213> ORGANISM: Canis sp.

<400> SEQUENCE: 20

Tyr Val Asp Ile His Asn Cys Asp Pro Ala Asn Pro Ser Glu Lys Asn
1               5                   10                  15

Ser Leu Ser Ile Gln Tyr Cys
            20

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Asn Cys Glu Pro Ala Asn Pro Ser Glu Lys Asn Ser Pro Ser Thr
1               5                   10                  15

<210> SEQ ID NO 22
<211> LENGTH: 326
<212> TYPE: PRT
<213> ORGANISM: Canis sp.

<400> SEQUENCE: 22

Met Leu Ala Gly Arg Gly Ala Arg Ala Gly Gly Leu Pro Arg Gly
1               5                   10                  15

Trp Thr Ala Leu Cys Leu Leu Ser Leu Leu Pro Phe Gly Phe Thr Asn
                20                  25                  30

Thr Glu Thr Val Ile Thr Pro Thr Val Pro Thr Ser Thr Glu Ile
            35                  40                  45

Met Ser Ala Val Ser Glu Asn Thr Ser Lys Arg Glu Ala Ile Thr Leu
    50                  55                  60

Thr Pro Ser Gly Thr Thr Thr Leu Tyr Ser Val Ser Gln Asp Ser Ser
65                  70                  75                  80

Gly Thr Thr Ala Thr Ile Ser Glu Thr Thr Val His Val Thr Ser Thr
                85                  90                  95

Ser Glu Ile Thr Leu Thr Pro Gly Thr Met Asn Ser Ser Val Gln Ser
            100                 105                 110

Gln Thr Ser Leu Ala Ile Thr Val Ser Phe Thr Pro Thr Asn Phe Ser
        115                 120                 125

Thr Ser Ser Val Thr Leu Glu Pro Ser Leu Leu Pro Gly Asn Gly Ser
    130                 135                 140

Asp Pro Pro Tyr Asn Ser Thr Ser Leu Val Thr Ser Pro Thr Glu Tyr
145                 150                 155                 160

Tyr Thr Ser Leu Ser Pro Thr Pro Ser Arg Asn Asp Thr Pro Ser Thr
                165                 170                 175

Ile Lys Gly Glu Ile Lys Cys Ser Gly Val Lys Glu Val Lys Leu Asn
            180                 185                 190

```
Gln Gly Ile Cys Leu Glu Leu Asn Glu Thr Ser Ser Cys Glu Asp Phe
            195                 200                 205

Lys Lys Asp Asn Glu Glu Lys Leu Thr Gln Val Leu Cys Glu Lys Glu
    210                 215                 220

Pro Ala Glu Ala Gly Ala Gly Val Cys Ser Leu Leu Ala Gln Ser
225                 230                 235                 240

Glu Val Arg Pro His Cys Leu Leu Val Leu Ala Asn Lys Thr Glu
                245                 250                 255

Leu Phe Ser Lys Leu Gln Leu Leu Arg Lys His Gln Ser Asp Leu Lys
                260                 265                 270

Lys Leu Gly Ile Arg Asp Phe Thr Glu Gln Asp Val Gly Ser His Gln
            275                 280                 285

Ser Tyr Ser Arg Lys Thr Leu Ile Ala Leu Val Thr Ser Gly Ile Leu
        290                 295                 300

Leu Ala Val Leu Gly Thr Thr Gly Tyr Phe Leu Met Asn Arg Arg Ser
305                 310                 315                 320

Trp Ser Pro Thr Gly Glu
                325
```

<210> SEQ ID NO 23
<211> LENGTH: 978
<212> TYPE: DNA
<213> ORGANISM: Canis sp.

<400> SEQUENCE: 23

```
atgctggcgg gcaggggcgc gcgcgcgggc ggcgggctgc cgcggggctg gaccgcgctc    60
tgcctgctca gtctgctgcc ctttgggttc acaaacacag aaaccgtgat tactcctacc   120
acagtgccaa cctccacaga aataatgtca gctgtttctg agaatacatc caaacgggaa   180
gccatcacac taactccttc tggaactacc accctgtact ctgtctctca agacagcagt   240
gggaccacag caaccatctc agagactaca gtccatgtca catctacctc tgagatcacc   300
ctaacgcctg ggaccatgaa ctcttctgtt cagtcgcaga cctctttagc tatcacggta   360
tcttttaccc caaccaactt ttcaacttca agtgtgacct ggagcccag cctgctacct   420
ggaaatggtt cggatccccc ctacaacagc accagccttg tgcatccccc cacggaatat   480
tatacatcac tttctcctac cccaagtaga aatgacaccc caagtaccat caagggagaa   540
atcaaatgtt ccggagtcaa agaagtgaaa ttgaaccaag gtatctgcct agagctaaat   600
gagacctcca gctgtgagga ctttaagaaa gataacgaag aaaaactgac ccaagtcctg   660
tgtgagaagg agccagctga ggctggggcc ggggtgtgct ccctgcttct ggcccagtct   720
gaggtgaggc ctcactgcct gctgctggtc ttggccaaca aaacagaact tttcagtaaa   780
ctccaacttc tgagaaagca ccagtctgac ctgaaaaagc tggggatccg agacttcact   840
gaacaagatg ttgggagcca ccagagctat cccgcaagaa ccctgattgc actggtcacc   900
tcagggatcc tgctggctgt cttgggcacc actggttact tcctgatgaa ccgccgcagt   960
tggagcccta caggagaa                                                  978
```

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ggaaatagcc cttgaccagg c                                            21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagccagtgg atagacagat g                                            21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtggatagac agatggggct g                                            21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aggatgatgt cttatgaaca a                                            21

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atgaacaacc tcacaggtat agagg                                        25

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctcacaggta tagaggttat g                                            21

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggcccacgtg gccaccatga caacacccag aaatt        35

<210> SEQ ID NO 31
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggtccggga ttctccacgt cacctgcttg tttgagtagt gagaagtttg ttgctccaga        60
tccagggatg ctgtcgtttt ctattggt        88

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caagcaggtg acgtggagga gaatcccgga cccatggaca acaccgagga cgtcat        56

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttaaggatcc ctactgggag ccggagtggc ggg        33

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggccggatcc ttcagagtga ctacatgaa        29

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttaaggatcc gcggccgctc agcgaggagg cagggcctgc atg        43

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

-continued

```
ggccagcgct gccaccatgc tggcgg                                        26
```

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
gggtccaggg ttctcctcca cgt                                           23
```

<210> SEQ ID NO 38
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
gctggagacg tggaggagaa ccctggaccc atggcctctc gggtgaccgc cc           52
```

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
ttaacctgca ggaggcggga agaccg                                        26
```

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Phe Ser Phe Ser Asp Cys Trp
1               5

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
ggattcagtt tcagtgactg ctgg                                          24
```

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Lys Tyr Asp Gly Arg Ala Thr
1               5

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
attaaatatg atggcagggc caca                                              24

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Gly Asn His Tyr Gly Gly Tyr Thr Leu Arg Phe Ala Tyr
1               5                   10

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
actgggaacc actacggagg ctataccctc cggtttgctt actg                        44

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Leu Leu His Ser Asn Gly Asn Thr Tyr
1               5                   10

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cagagtctct tacatagtaa tggaaacacc tat                                    33

<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Val Ser
1

<210> SEQ ID NO 49
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 ttggtttcc                                                                9

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Gln Gly Thr His Ala Pro Pro Thr Phe Gly Gly
1               5                   10

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gttcaaggta cccatgctcc tccgacgttc ggtggc                                  36

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ser Gly Gly Gly Lys
1               5

<210> SEQ ID NO 53
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

```
Arg Met Ser Pro Ser Asn Gln Thr Asp Lys Leu Ala Ala Phe Pro Glu
     50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln
145
```

<210> SEQ ID NO 54
<211> LENGTH: 435
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 54

```
ccaggatggt tcttagactc cccagacagg ccctggaacc cccccacctt ctccccagcc      60
ctgctcgtgg tgaccgaagg ggacaacgcc accttcacct gcagcttctc caacacatcg     120
gagagcttcg tgctaaactg gtaccgcatg agccccagca accagacgga caagctggcc     180
gccttccccg aggaccgcag ccagcccggc caggactgcc gcttccgtgt cacacaactg     240
cccaacgggc gtgacttcca catgagcgtg gtcagggccc ggcgcaatga cagcggcacc     300
tacctctgtg gggccatctc cctggccccc aaggcgcaga tcaaagagag cctgcgggca     360
gagctcaggg tgacagagag aagggcagaa gtgcccacag cccaccccag cccctcaccc     420
aggccagccg gccag                                                      435
```

<210> SEQ ID NO 55
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 55

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
```

```
                100              105              110
Ala Arg Arg Asn Asp Ser Gly Thr Tyr Leu Cys Gly Ala Ile Ser Leu
            115                  120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln
            165

<210> SEQ ID NO 56
<211> LENGTH: 495
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcaggggcc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccaccccag cccctcaccc     480
aggccagccg gccag                                                       495

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Met Gln Ile Pro Gln Ala Pro Trp Pro Val Val Trp Ala Val Leu Gln
1               5                   10                  15

Leu Gly Trp Arg
            20

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser Gly Gly Gly
1               5

<210> SEQ ID NO 59
<211> LENGTH: 297
<212> TYPE: PRT
<213> ORGANISM: Homo sapiens
```

<400> SEQUENCE: 59

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 60
<211> LENGTH: 44
<212> TYPE: PRT
<213> ORGANISM: Homo sapiens

<400> SEQUENCE: 60

Ile Ser His Phe Leu Lys Met Glu Ser Leu Asn Phe Ile Arg Ala His
1               5                   10                  15

Thr Pro Tyr Ile Asn Ile Tyr Asn Cys Glu Pro Ala Asn Pro Ser Glu
            20                  25                  30

Lys Asn Ser Pro Ser Thr Gln Tyr Cys Tyr Ser Ile
        35                  40

<210> SEQ ID NO 61

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Tyr Val Asp Ile His Asn Cys Asp Pro Ala Asn Pro Ser Glu Lys Asn
1               5                   10                  15

Ser Leu Ser Ile Gln Tyr Cys Gly Ser Gly Gly Gly Lys
            20                  25

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Gly Ser Gly Gly Gly Ser Gly Gly Gly Ser Gly Gly Gly Ser
1               5                   10                  15
```

ANTI-CD20 ANTIBODY AND USES THEREOF

CROSS-REFERENCE TO RELATED APPLICATION

This application is a National Stage Application of PCT/US2019/018535, filed Feb. 19, 2019, which claims priority to U.S. provisional application No. 62/633,034, filed Feb. 20, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 22, 2019, is named 115872-0538_SL.txt and is 36,516 bytes in size.

BACKGROUND OF THE INVENTION

The majority of adult B-cell malignancies, including acute lymphoblastic leukemia (ALL), chronic lymphocytic leukemia, and non-Hodgkin's lymphoma, are incurable despite currently available therapies. However, adoptive therapy with genetically engineered chimeric antigen receptor (CAR) T cells is one approach that has been recently highly successful in patients with acute lymphocytic leukemia (ALL) and has also generated responses in patients with chronic lymphocytic leukemia (CLL) and B cell non-Hodgkin lymphoma (NHL), although less profound (Park et al. (2016) *Blood* 127(26):3312-20; Davila et al. (2014) *Science Translational Medicine* 6(224):224ra25; Davila et al. (2016) *Int J Hematol.* 104(1):6-17; Turtle et al. (2016) *Science Translational Medicine* 8(355):355ra116).

Adoptive cell transfer (ACT) is a form of immunotherapy that involves the transfer of immune cells with antitumor activity into patients. ACT typically involves isolation of lymphocytes with antitumor activity from a patient, culturing the lymphocytes in vitro to expand the population, and then infusing the lymphocytes into the cancer-bearing host. Lymphocytes used for adoptive transfer can either be derived from the stroma of resected tumors (e.g., tumor infiltrating lymphocytes), from the lymphatics or lymph nodes, or from the blood. In some cases, the isolated lymphocytes are genetically engineered to express anti-tumor T cell receptors (TCRs) or chimeric antigen receptors (CARs). The lymphocytes used for infusion can be isolated from a donor (allogeneic ACT), or from the cancer-bearing host (autologous ACT). Immunotherapy is a targeted therapy that has the potential to provide for the treatment of cancer.

However, malignant cells adapt to generate an immunosuppressive microenvironment to protect themselves from immune recognition and elimination. This "hostile" tumor microenvironment poses a challenge to methods of treatment involving stimulation of an immune response, such as targeted T cell therapies. Accordingly, novel therapeutic strategies for treating neoplasia are needed.

SUMMARY OF THE INVENTION

Provided herein, in certain embodiments, are anti-CD20 antibodies and CD20 antigen binding fragments thereof. In some embodiments, the anti-CD20 antibodies and CD20 antigen binding fragments thereof are specific for canine CD20. In some embodiments, the isolated antibody or an antigen binding portion thereof that specifically binds to a canine CD20 cyclic peptide having the sequence of SEQ ID NO: 20, wherein the cysteine at position 7 of SEQ ID NO: 20 forms a disulfide bond with the cysteine at position 23 of SEQ ID NO: 20. In some embodiments, the antibody or an antigen binding portion thereof binds to the canine CD20 cyclic peptide at a higher affinity than a linear peptide having the sequence of SEQ ID NO: 21. In some embodiments, the antibody or an antigen binding portion thereof comprises a heavy chain variable domain (VH) comprising SEQ ID NO: 4, or is at least 80%, 85%, 90%, 95%, 96%, 97%, 98%, or 99% identical to SEQ ID NO: 4. In some embodiments, the antibody or an antigen binding portion thereof comprises a VH complementarity determining region (CDR)1 of SEQ ID NO: 40, or is at least 80%, 90%, 91%, 92%, 93%, 94%, 95%, 96%, 97%, 98%, or 99% identical to SEQ ID NO: 40. In some embodiments, the antibody or an antigen binding portion thereof comprises a VH CDR2 of SEQ ID NO: 42, or is at least 80%, 90%, 91%, 92%, 93%, 94%, 95%, 96%, 97%, 98%, or 99% identical to SEQ ID NO: 42. In some embodiments, the antibody or an antigen binding portion thereof comprises a VH CDR3 consisting of a threonine (T) residue. In some embodiments, the antibody or an antigen binding portion thereof comprises a light chain variable domain (LH) comprising SEQ ID NO: 6, or is at least 80%, 85%, 90%, 95%, 96%, 97%, 98%, or 99% identical to SEQ ID NO: 6. In some embodiments, the antibody or an antigen binding portion thereof comprises a VL CDR1 of SEQ ID NO: 46, or is at least 80%, 90%, 91%, 92%, 93%, 94%, 95%, 96%, 97%, 98%, or 99% identical to SEQ ID NO: 46. In some embodiments, the antibody or an antigen binding portion thereof comprises a VL CDR2 of SEQ ID NO: 48 or a VL CDR2 having at least 80%, 90%, 91%, 92%, 93%, 94%, 95%, 96%, 97%, 98%, 99% or more sequence identity with SEQ ID NO: 48. In some embodiments, the antibody or an antigen binding portion thereof comprises a VL CDR3 of SEQ ID NO: 50 or a VL CDR3 having at least 80%, 90%, 91%, 92%, 93%, 94%, 95%, 96%, 97%, 98%, 99% or more sequence identity with SEQ ID NO: 50. In some embodiments, the isolated antibody or an antigen binding portion thereof is a full length antibody, a Fab fragment, a F(ab')2 fragment, or a single chain variable fragment (scFV). In some embodiments, the isolated antibody or an antigen binding portion thereof is a scFv. In some embodiments, the isolated antibody or an antigen binding portion thereof comprises SEQ ID NO: 8, or is at least 85%, 90%, 95%, 96%, 97%, 98%, or 99% identical to SEQ ID NO: 8. In some embodiments, the isolated antibody or an antigen binding portion thereof is a chimeric antigen receptor (CAR).

Provided herein, in certain embodiments are fusion proteins comprising the isolated antibody or an antigen binding portion thereof provided herein where the fusion protein comprises a scFv-Fc fusion protein, immunoconjugate, or bispecific antibody. In some embodiments, the fusion protein comprises a second component selected from the group consisting of a cytotoxin, a detectable label, a radioisotope, a therapeutic agent, a liposome, a nanoparticle, a binding protein, or an antibody.

Provided herein, in certain embodiments, are nucleic acids encoding the isolated an antibody or antigen binding portion thereof provided herein. Also provided herein, in certain embodiments, are expression vectors comprising a nucleic acid provided herein. Also provided herein, in certain embodiments, are cells comprising a nucleic acid or vector provided herein. In some embodiments, the cell is an immune cell. In some embodiments, the immune cell is a T-cell or natural killer (NK) cell.

Provided herein, in certain embodiments, are methods for the production of anti-CD20 antibodies and CD20 antigen binding fragments thereof. In some embodiments, the anti-CD20 antibody or antigen binding fragment thereof is labeled with a detectable moiety. In some embodiments, the anti-CD20 antibody or antigen binding fragment thereof is a full immunoglobulin, a heavy chain variable region (VH), a light chain variable region (VL) or a single-chain variable fragment (scFv).

Provided herein, in certain embodiments, are chimeric T cell receptors comprising one or more complementarity determining regions (CDR) of an anti-CD20 antibody or antigen binding fragment thereof provided herein. Provided herein, in certain embodiments, are chimeric T cell receptors comprising CDR1, CDR2, and/or CDR3 of an anti-CD20 antibody or antigen binding fragment thereof provided herein. Provided herein, in certain embodiments, are chimeric T cell receptors comprising the light chain or an antigen-binding portion thereof of an anti-CD20 antibody provided herein. Provided herein, in certain embodiments, are chimeric T cell receptors comprising the heavy chain or an antigen-binding portion thereof of an anti-CD20 antibody provided herein. Provided herein, in certain embodiments, are chimeric T cell receptors comprising a heavy chain or an antigen-binding portion thereof and a light chain or an antigen-binding portion thereof of an anti-CD20 antibody provided herein. In some embodiments, the chimeric T cell receptor comprises a co-stimulatory portion. In some embodiments, the co-stimulatory portion is a human, rodent, or canine co-stimulatory protein. In some embodiments, the chimeric T cell receptor comprises a CD3 zeta chain. In some embodiments, the co-stimulatory portion is a human, rodent, or canine CD3 zeta chain.

In some embodiments, a chimeric antigen receptor provided herein comprises (i) antigen binding portion comprising the isolated antibody or antigen binding portion thereof provided here or a fusion protein provided herein; (ii) a transmembrane portion; and (iii) a cytoplasmic signaling portion. In some embodiments, the antigen binding portion comprises a heavy chain variable domain (VH) comprising SEQ ID NO: 4, or is at least 80%, 85%, 90%, 95%, 96%, 97%, 98%, or 99% identical to SEQ ID NO: 4 and/or a light chain variable domain (LH) comprising SEQ ID NO: 6, or is at least 80%, 85%, 90%, 95%, 96%, 97%, 98%, or 99% identical to SEQ ID NO: 6. In some embodiments, the antigen binding portion comprises (a) a heavy chain variable domain (VH) comprising (i) a variable heavy chain (VH) complementarity determining region (CDR) 1 of SEQ ID NO: 40, or at least 80%, 90%, 91%, 92%, 93%, 94%, 95%, 96%, 97%, 98%, or 99% identical to SEQ ID NO: 40; (ii) a VH CDR2 of SEQ ID NO: 42, or at least 80%, 90%, 91%, 92%, 93%, 94%, 95%, 96%, 97%, 98%, or 99% identical to SEQ ID NO: 42; and/or (iii) a VH CDR3 consisting of a threonine (T) residue; and/or (b) a light chain variable domain (LH) comprising (i) a light chain variable domain (VL) complementarity determining region (CDR) 1 of SEQ ID NO: 46, or at least 80%, 90%, 91%, 92%, 93%, 94%, 95%, 96%, 97%, 98%, or 99% identical to SEQ ID NO: 46; (b) a VL CDR2 of SEQ ID NO: 48, or at least 80%, 90%, 91%, 92%, 93%, 94%, 95%, 96%, 97%, 98%, or 99% identical to SEQ ID NO: 48; and/or (c) a VL CDR3 of SEQ ID NO: 50, or at least 80%, 90%, 91%, 92%, 93%, 94%, 95%, 96%, 97%, 98%, or 99% identical to SEQ ID NO: 50. In some embodiments, the antigen binding portion comprises SEQ ID NO: 8, or is at least 85%, 90%, 95%, 96%, 97%, 98%, or 99% identical to SEQ ID NO: 8. In some embodiments, the chimeric antigen receptor comprises a CD8 leader sequence, a CD28 costimulatory domain, a CD3ζ-chain, a 4-1BBL costimulatory domain, a PD1-DNR domain, a CD34 domain, or any combination thereof.

Provided herein, in certain embodiments, are cells expressing the chimeric antigen receptor provided herein. In some embodiments, the cell is a T cell or natural killer (NK) cell.

Provided herein, in certain embodiments, are methods for the production of chimeric T cell receptors comprising an anti-CD20 antibody or antigen binding fragment thereof provided herein.

Provided herein, in certain embodiments, are pharmaceutical compositions comprising an antigen-binding protein or fragment or derivative thereof provided herein or a fusion protein provided herein; and a physiologically acceptable diluent, excipient or carrier.

Provided herein, in certain embodiments, are methods of treatment using the anti-CD20 antibodies or antigen binding fragments thereof provided herein.

Provided herein, in certain embodiments, are methods for inhibiting tumor growth or metastasis comprising contacting a tumor cell with an effective amount of the antibody or an antigen binding portion thereof provided herein. In some embodiments, the tumor cell is a canine tumor cell.

Provided herein, in certain embodiments, are methods for treating a condition mediated by B-cells in a subject in need thereof comprising administering an effective amount of the antibody or an antigen binding portion thereof provided herein. In some embodiments, the condition mediated by B-cells is a B cell lymphoma. In some embodiments, the condition mediated by B-cells is an immune mediated disease. In some embodiments, the immune mediated disease is an autoimmune disease. In some embodiments, the autoimmune disease is selected from the group consisting of rheumatoid arthritis, systemic lupus erythematosus (SLE), Sjogren's syndrome, vasculitis, multiple sclerosis, Graves' disease, idiopathic thrombocytopenia, dermatomyositis, immune mediated thrombocytopenia, polymyocytosis, pemphigus, immune mediated hemolytic anemia and bullous pemphigoid.

Provided herein, in certain embodiments, are methods for treatment comprising isolating T-cells from a subject, transfecting the T-cells with a vector comprising a nucleic acid encoding an antibody or an antigen binding portion thereof provided herein, and administering the transfected T-cells to the subject. In some embodiments, the subject is a canine subject.

Provided herein, in certain embodiments, are uses of an antibody or an antigen binding fragment thereof that specifically binds to a canine CD20 cyclic peptide having the sequence of SEQ ID NO: 20, wherein the cysteine at position 7 of SEQ ID NO: 20 forms a disulfide bond with the cysteine at position 23 of SEQ ID NO: 20 in the preparation of a medicament for the treatment or prevention of a condition mediated by B-cells in a subject in need thereof, wherein the cysteine at position 7 of SEQ ID NO: 20 forms a disulfide bond with the cysteine at position 23 of SEQ ID NO: 20. In some embodiments, the condition mediated by B-cells is a B cell lymphoma or leukemia. In some embodiments, the condition mediated by B-cells is an immune mediated disease. In some embodiments, the immune mediated disease is an autoimmune disease. In some embodiments, the autoimmune disease is selected from the group consisting of rheumatoid arthritis, systemic lupus erythematosus (SLE), Sjogren's syndrome, vasculitis, multiple sclerosis, Graves' disease, idiopathic thrombocytopenia, dermatomyositis, immune mediated thrombocytopenia, polymyocytosis, pemphigus, immune mediated hemolytic anemia and bullous pemphigoid. In some embodiments, the isolated antibody or an antigen binding portion thereof comprises a heavy chain variable domain (VH) comprising SEQ ID NO: 4, or is at least 85%, 90%, 95%, 96%, 97%, 98%, or 99% identical to SEQ ID NO: 4. In some embodiments, the isolated antibody or an antigen binding portion thereof comprises a light chain variable domain (LH) comprising SEQ ID NO: 6, or is at least 85%, 90%, 95%, 96%, 97%, 98%, or 99% identical to SEQ ID NO: 6. In some embodiments, the isolated antibody or an antigen binding portion thereof is a full length antibody, a Fab fragment, a F(ab')2 fragment, or a single chain variable fragment (scFV). In some embodiments, the antibody is a scFv. In some embodiments, the isolated antibody or an antigen binding portion thereof comprises SEQ ID NO: 8, or is at least 85%, 90%, 95%, 96%, 97%, 98%, or 99% identical to SEQ ID NO: 8.

Provided herein, in certain embodiments, are antigens for the production anti-CD20 antibodies or antigen binding fragments thereof provided herein. In some embodiments, provided is a canine CD20 cyclic peptide comprising a canine CD20 epitope having the sequence of SEQ ID NO: 20, wherein the cysteine at position 7 of SEQ ID NO: 20 forms a disulfide bond with the cysteine at position 23 of SEQ ID NO: 20. In some embodiments, the canine CD20 cyclic peptide further comprises a carrier protein. In some embodiments, the carrier protein is KLH. In some embodiments, the carrier protein is conjugated to a linker. In some embodiments, the linker is a sulfosuccinimidyl 4-(N-maleimidomethyl)cyclohexane-1-carboxylate linking group. In some embodiments, the canine CD20 cyclic peptide comprises a peptide spacer between the canine CD20 epitope and the carrier protein. In some embodiments, the peptide spacer comprises the sequence of SEQ ID NO:4. Also provided herein are methods of producing antibodies using a canine CD20 cyclic peptide provided herein. Also provided herein are methods of stimulating of an immune response in vitro or in vivo using a canine CD20 cyclic peptide provided herein.

Provided herein, in certain embodiments, are methods for the detection of CD20 protein or an extracellular domain of a CD20 protein in a biological sample with any of the anti-CD20 antibodies or antigen binding fragments thereof provided herein. In some embodiments, the methods for detecting a CD20 protein or an extracellular domain of a CD20 protein in a biological sample, comprises contacting a biological sample with the antibody or an antigen binding portion thereof provided herein. In some embodiments, the biological sample is a biopsy, tissue, blood, serum, plasma, or lymphatic fluid sample. In some embodiments, the biological sample comprises cells that express a CD20 protein or a fragment thereof or is a cell lysate prepared from cells that express a CD20 protein or a fragment thereof. In some embodiments, the biological sample comprises B cells or a B cell lysate.

Also provided are compositions, kits, and methods of treatment relating to antigen-binding proteins that bind to a canine CD20 antigenic peptide (K9CD20). The antigen-binding proteins disclosed herein demonstrate improved specificity for an epitope comprised in the extracellular domain of canine CD20 protein, and can mediate killing of B-cell lymphoma in vitro and in vivo. In some embodiments, a kits for detecting a CD20 protein or an extracellular domain of a CD20 protein in a biological sample comprises an antibody or an antigen binding portion thereof provided herein and at least one reagent for the detection of the antibody or antigen binding portion thereof.

BRIEF DESCRIPTION OF THE DRAWINGS

FIG. 3. illustrates CD20 extracellular sequences in canine (SEQ ID NO: 1), human (SEQ ID NO: 2), and mouse (SEQ ID NO: 3) for epitope design. The highlighted portion in the human sequence is the rituximab epitope. The highlighted portion of the canine CD20 represents the epitope that was used in the present disclosure to generate canine CD20 antibodies. The two cysteines in the canine epitope are cyclized through cysteine side chains.

FIG. 4 discloses the full-length sequence as SEQ ID NO: 61.

FIG. 5 discloses the full-length sequence as SEQ ID NO: 61.

FIG. 10A shows the transduction efficiency in K9CD20-targeted chimeric antigen receptor (CAR) T cells assessed by coexpression of L-NGFR. FIG. 10B shows the results of a Cr51 cytotoxic release assay in EL4 tumor cells. FIG. 10C shows the results of a Cr51 cytotoxic release assay in NALM6 or NALM6-K9CD20 tumor cells.

FIG. 13 shows the results of a Cr51 cytotoxic release assay in NALM6 or NALM6-K9CD20 tumor cells.

FIG. 14 illustrates schematics of CAR cloning constructs. FIG. 14A illustrates the cloning construct for the light and heavy chain variable regions of the rat anti-canine CD20. FIG. 14B illustrates the anti-K9CD20 scFv construct. FIG. 14B discloses "(G3S)4" as SEQ ID NO: 62. FIG. 14C illustrates the SFG-anti-K9CD20 CAR LNGFR construct. FIG. 14C discloses "(G3S)4" as SEQ ID NO: 62. FIG. 14D illustrates the SFG-K9CD20-dsRed construct. FIG. 14E illustrates the SFG-K27-CAR construct. FIG. 14E discloses "(G3S)4" as SEQ ID NO: 62. FIG. 14F illustrates the SFG-K36-CAR construct. FIG. 14F discloses "(G3S)4" as SEQ ID NO: 62. FIG. 14G illustrates the SFG-K9CD34t-K27 construct. FIG. 14G discloses "(G3S)4" as SEQ ID NO: 62. FIG. 14H illustrates the SFG-K9CD34t-K36 construct. FIG. 14H discloses "(G3S)4" as SEQ ID NO: 62. FIG. 14I illustrates the K27/PD1-DNR construct. FIG. 14I discloses "(G3S)4" as SEQ ID NO: 62. FIG. 14J illustrates SFG vector backbone. FIG. 14K illustrates the SFG-PmlI-αk9CD2028z-LNGFR-BamHI construct.

FIG. 17A illustrates the forward scatter and side scatter plot. FIG. 17B illustrates the histogram for FITC-A.

FIG. 18A illustrates the forward scatter and side scatter plot. FIG. 18B illustrates the histogram for FITC-A.

FIG. 19A illustrates the forward scatter and side scatter plot. FIG. 19B illustrates the histogram for FITC-A.

FIG. 20A illustrates the forward scatter and side scatter plot. FIG. 20B illustrates the histogram for FITC-A.

FIG. 21 discloses SEQ ID NO: 61.

FIG. 22 discloses SEQ ID NO: 61, 61, and 61.

FIG. 23 discloses SEQ ID NO: 61, 61, and 61.

FIG. 24 illustrates flow cytometry data for Canine PBMCs cells stained with CD21 and anti-CD20 hybridoma clone 18F6. The top panels show cells stained with CD21 (PE/FL2-H) and no stain on FL1-H. The bottom panels show cells stained with CD21 (PE/FL2-H) and the antibody from hybridoma clone 18F6 (18F6+Goat anti rat IgG-FITC/FL1-H). The left panels of each set illustrate the forward scatter and side scatter plots (FSC v. SSC), and the right panels of each set illustrate the fluorescence plots.

DETAILED DESCRIPTION OF THE INVENTION

Figure 1:
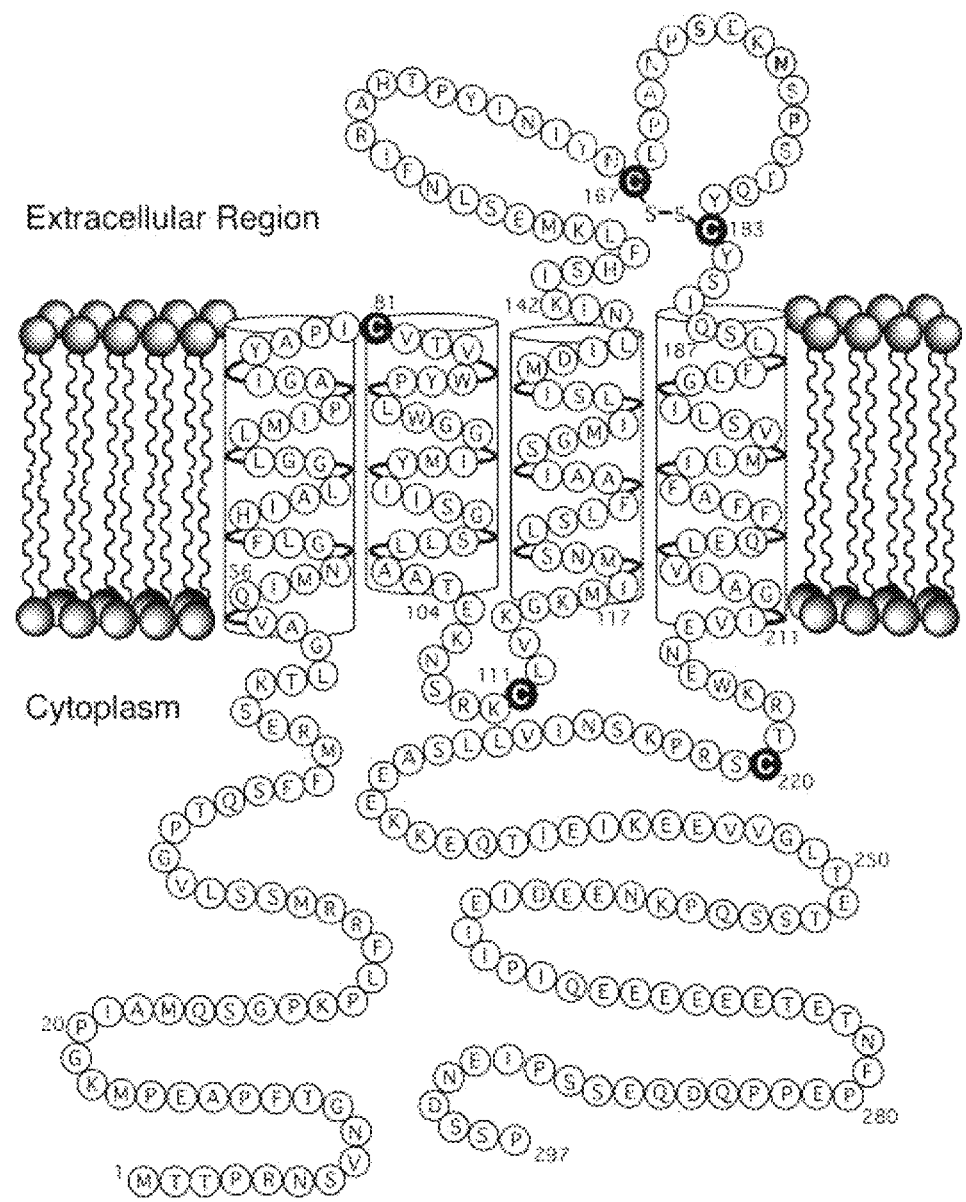
FIG. 1 illustrates the structure human CD20 (SEQ ID NO: 59)_(adapted from Ernst J. A. et al. *Biochemistry* 44: 15150 (2005)).

The present disclosure is not to be limited in terms of the particular embodiments described in this application, which are intended as single illustrations of individual aspects of the present disclosure. All the various embodiments of the present disclosure will not be described herein. Many modifications and variations of the present disclosure can be made without departing from its spirit and scope, as will be apparent to those skilled in the art. Functionally equivalent methods and apparatuses within the scope of the present disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the present disclosure are described in terms of Markush groups, those skilled in the art will recognize that the present disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Unless defined otherwise, all technical and scientific terms used herein have the same meaning as commonly understood by one of ordinary skill in the art to which this disclosure belongs.

I. Definitions

The terminology used herein is for the purpose of describing particular embodiments only and is not intended to be limiting of the present disclosure. In the description that follows, certain conventions will be followed regarding the usage of terminology. Generally, terms used herein are intended to be interpreted consistently with the meaning of those terms as described below and as they are known to those of skill in the art.

As used herein, the singular forms "a", "an" and "the" are intended to include the plural forms as well, unless the context clearly indicates otherwise.

As used herein, the term "about" means that a value can vary +/−20%, +/−15%, +/−10% or +/−5% and remain within the scope of the present disclosure. For example, "a concentration of about 200 IU/mL" encompasses a concentration between 160 IU/mL and 240 IU/mL.

As used herein, the term "administration" of an agent to a subject includes any route of introducing or delivering the agent to a subject to perform its intended function. Administration can be carried out locally or systemically (e.g., enteral or parenteral administration). Administration can be carried out by any suitable route, including intravenously, intramuscularly, intraperitoneally, orally, topically, intradermally, transdermally, intratumorally, intraocularly, intracerebrally, epidurally, intrathecally intranasally, intratracheally, intraosseously, epicutaneously, or subcutaneously. Administration includes self-administration and the administration by another.

As used herein, the term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

As used herein, the terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, an "antigen-binding protein" is a protein or polypeptide that comprises an antigen-binding region or antigen-binding portion that has a strong affinity for another molecule to which it binds (antigen). Antigen-binding proteins encompass antibodies, antibody fragments, antibody derivatives, antibody analogs, fusion proteins, and antigen receptors including chimeric antigen receptors (CARs). An antigen-binding protein or fragment or derivative thereof optionally comprises a scaffold or framework portion that allows the antigen-binding portion to adopt a conformation that promotes binding of the antigen-binding protein to the antigen. The antigen-binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen-binding protein as well as wholly synthetic scaffolds comprising, for example, a biocompatible polymer. See, for example, Komdorfer et al., 2003, Proteins: Structure, Function, and Bioinformatics, Volume 53, Issue 1:121-129 and Roque et al., 2004, *Biotechnol. Prog.* 20:639-654. In addition, peptide antibody mimetics ("PAMs") can be used, as well as scaffolds based on antibody mimetics utilizing fibronectin components as a scaffold.

In some embodiments, an antigen-binding protein or fragment or derivative thereof or fusion protein thereof has a single binding site. In some embodiments, an antigen-binding protein or fragment or derivative thereof or fusion protein thereof has more than one binding site. In some embodiments where there is more than one binding site, the binding sites are identical to one another. In some embodiments where there is more than one binding site, the binding sites are different. For example, a naturally occurring human immunoglobulin typically has two identical binding sites, while a "bispecific antibody" or "bifunctional antibody" has two different binding sites.

As used herein, an "antibody" and "antibodies" refer to antigen-binding proteins that arise in the context of the immune system. The term "antibody" as referred to herein includes whole, full length antibodies and any fragment or derivative thereof in which the "antigen-binding portion" or "antigen-binding region" or single chains thereof are retained. A naturally occurring "antibody" (immunoglobulin) is a glycoprotein comprising at least two heavy (H) chains and two light (L) chains inter-connected by disulfide bonds. Each heavy chain is comprised of a heavy chain variable region (abbreviated herein as VH) and a heavy chain constant region. Heavy chains are classified as mu, delta, gamma, alpha, or epsilon, and define the antibody's isotype as IgM, IgD, IgG, IgA, and IgE, respectively. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs arranged from amino terminus to carboxyl-terminus in the following order: FR1, CDR1, FR2, CDR2, FR3, CDR3, FR4. The heavy and light chains form two regions: the Fab (fragment, antigen binding) region, also referred to as the variable (Fv) region, and the Fc (fragment, crystallizable) region. The variable regions (Fv) of the heavy and light chains contain a binding domain that interacts with an antigen. The constant (Fc) regions of the antibodies can mediate the binding to host tissues or factors, including various cells of the immune system (e.g., effector cells) and the first component (C1q) of the classical complement system. The term "Fc" as used herein includes native and mutant forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns. One suitable Fc polypeptide is derived from the human IgG1 antibody.

Antibodies can be obtained from sources such as serum or plasma that contain immunoglobulins having varied antigenic specificity or recombinantly produced. If such antibodies are subjected to affinity maturation, they can be enriched for a particular antigenic specificity. Such affinity matured preparations of antibodies usually are made of less than about 10% of antibodies having specific binding activity for the particular antigen. Subjecting these preparations to several rounds of affinity maturation can increase the proportion of antibody having specific binding activity for the antigen. Antibodies prepared in this manner are often referred to as "affinity matured."

Fragments, derivatives, or analogs of antigen-binding proteins such as antibodies can be readily prepared using techniques well-known in the art. The term "fragment" as used herein refers to a polypeptide that has an amino-terminal and/or carboxyl-terminal deletion as compared to a corresponding full-length antigen-binding protein. Examples of fragments of antigen-binding proteins encompassed within the term "fragments" include a Fab fragment; a monovalent fragment consisting of the VL, VH, CL and CH1 domains; a F(ab')2 fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., 1989, *Nature,* 341:544-546), which consists of a VH domain; an isolated complementarity determining region (CDR); and a single chain variable fragment (scFv). A "derivative" of an antigen-binding protein is a polypeptide (e.g., an antibody) that has been chemically modified, e.g., via conjugation to another chemical moiety (such as, for example, polyethylene glycol or albumin, e.g., human serum albumin), phosphorylation, and/or glycosylation.

As used herein, a "scFv" is a monovalent molecule that can be engineered by joining, using recombinant methods, the two domains of the Fv fragment, VL and VH, by a synthetic linker that enables them to be made as a single protein chain (see e.g., Bird et al., 1988, *Science,* 242:423-426; and Huston et al., 1988, *Proc. Natl. Acad. Sci.* 85:5879-5883). Such single chain antigen-binding peptides are also intended to be encompassed within the term "antigen-binding portion." These antibody fragments are obtained using conventional techniques known to those of skill in the art, and the fragments are screened for utility in the same manner as are intact antibodies. An exemplary scFv molecule is provided below as SEQ ID NO: 10, which contains a VL segment represented as SEQ ID NO: 6 and a VH segment represented as SEQ ID NO: 4 connected by a linker sequence represented as SEQ ID NO: 10.

As used herein, "monoclonal antibody" refers to a population of identical antibodies, meaning that each individual antibody molecule in a population of monoclonal antibodies is identical to the others. This property is in contrast to that of a polyclonal population of antibodies, which contains antibodies having a plurality of different sequences. Monoclonal antibodies can be produced by a number of well-known methods (Smith et al. (2004) 1 Clin. *Pathol.* 57: 912-917; and Nelson et al. (2000)*J Clin Pathol,* 53: 111-117). For example, monoclonal antibodies can be produced by immortalization of a B cell, for example through fusion with a myeloma cell to generate a hybridoma cell line or by infection of B cells with virus such as EBV. Recombinant technology also can be used to produce antibodies in vitro from clonal populations of host cells by transforming the host cells with plasmids carrying artificial sequences of nucleotides encoding the antibodies.

As used herein, the term "chimeric antigen receptor" or "CAR" as used herein refers to an antigen-binding domain that is fused to an intracellular signaling domain (also called cytoplasmic signaling domain) capable of activating or stimulating an immune cell. Most commonly, the CAR's extracellular binding domain is composed of a single chain variable fragment (scFv) derived from fusing the variable heavy and light regions of a murine or humanized monoclonal antibody. Alternatively, scFvs can be used that are derived from Fab's (instead of from an antibody, e.g., obtained from Fab libraries). In various embodiments, this scFv is fused to a transmembrane domain and then to an intracellular signaling domain. "First-generation" CARs include those that solely provide CD3 signals upon antigen binding, "Second-generation" CARs include those that provide both costimulation (e.g., CD28 or CD137) and activation (CD3ζ). "Third-generation" CARs include those that provide multiple costimulation (e.g., CD28 and CD137/4-1BBL) and activation (CD3). In various embodiments, the CAR is selected to have high affinity or avidity for the antigen.

As used herein, a "CD28 polypeptide" refers to a protein having at least 85, 90, 95, 96, 97, 98, 99 or 100% identity to GenBank Accession No: NP_001003087.2 or a fragment thereof that has stimulatory activity, for example, amino acids 115 through 221 of GenBank Accession No: NP_001003087.2. An exemplary CD28 polypeptide is provided below as SEQ ID NO: 14.

As used herein, a "CD28 nucleic acid molecule" refers to polynucleotide encoding a CD28 polypeptide. An exemplary CD28 nucleic acid molecule is provided below as SEQ ID NO: 15.

As used herein, a "CD3 zeta chain polypeptide" or "CD3 polypeptide" refers to a protein having at least 85, 90, 95, 96, 97, 98, 99 or 100% identity to GenBank Accession No: XP_005623027.1 or a fragment thereof that has stimulatory activity, for example, amino acids 65 through 185 of GenBank Accession No: XP_005623027.1. An exemplary CD3ζ polypeptide is provided below as SEQ ID NO: 16.

As used herein, a "CD3 zeta chain nucleic acid molecule" or "CD3 nucleic acid molecule" refers to a polynucleotide encoding a CD3 polypeptide. An exemplary CD3 nucleic acid molecule is provided below as SEQ ID NO: 17.

As used herein, a "4-1BBL polypeptide" refers to a protein having at least 85%, 90%, 95%, 96%, 97%, 98%, 99% or 100% identity to GenBank Accession No: XP_005633029.1 or a fragment thereof that that acts as a tumor necrosis factor (TNF) ligand. An exemplary 4-1BB is provided below as SEQ ID NO: 18.

As used herein, a "4-1BBL nucleic acid molecule" refers to a polynucleotide encoding a 4-1BBL polypeptide. An exemplary 4-1BBL nucleic acid molecule is provided below as SEQ ID NO: 19.

As used herein, the phrase "activates an immunoresponsive cell" refers to induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds antigen, a formation of an immunological synapse occurs that includes clustering of many molecules near the bound receptor (e.g., CD4, CD8, CD3γ, CD3=δ6, CD3ε, or CD3ζ) This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

As used herein, the phrase "stimulates an immunoresponsive cell" refers to a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Without being bound to a particular theory, receiving multiple stimulatory signals is important to mount a robust and long-term T cell mediated immune response. Without receiving these stimulatory signals, T cells quickly become inhibited and unresponsive to antigen. While the effects of these co-stimulatory signals vary and remain partially understood, they generally result in modifying gene expression (e.g., increasing or decreasing) in order to generate long lived, proliferative, and anti-apoptotic T cells that robustly respond to antigen for complete and sustained eradication.

As used herein, the term "affinity" refers to a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

As used herein, the term "immunostimulatory activity" refers to induction of signal transduction or changes in protein expression in a cell (e.g., an activated immunoresponsive cell) resulting in an increase in an immune response. Immunostimulatory activity can include pro-inflammatory activity. Polypeptides known to stimulate or increase an immune response via their binding include, but are not limited to, CD28, OX-40, 4-1BB, and their corresponding ligands, including B7-1, B7-2, OX-40L, and 4-1BBL. Such polypeptides are present in the tumor microenvironment and activate immune responses to neoplastic cells. In various embodiments, promoting, stimulating, or agonizing pro-inflammatory polypeptides and/or their ligands enhances the immune response of the immunoresponsive cell.

As used herein, an "epitope" refers to the portion of a molecule that is bound by an antigen-binding protein or fragment or derivative thereof (e.g., by an antibody). An epitope can comprise noncontiguous portions of the molecule, for example, in a polypeptide, amino acid residues that are not contiguous in the polypeptide's primary sequence, but that, in the context of the polypeptide's tertiary and quaternary structure, are near enough to each other to be bound by an antigen-binding protein).

As used herein, a "CD20 polypeptide" refers to a protein having at least 85, 90, 95, 96, 97, 98, 99 or 100% identity to GenBank Accession NO: XP_005633357.1 or a fragment thereof that has activating or stimulatory activity, such as a CD20 epitope. As used herein, a "CD20 extracellular domain" refers to a CD20 polypeptide that represents the extracellular portion of a native CD20 protein. A few exemplary CD20 polypeptides derived from the CD20 extracellular domains of canine, human and mouse CD20 are provided below as SEQ ID NOs: 1, 2 and 3, respectively.

As used herein, the term "isolated" when referring to a molecule, for example, an antigen-binding protein or fragment or derivative thereof, is a molecule that by virtue of its origin or source of derivation (1) is not associated with naturally associated components that accompany it in its native state, (2) is substantially free of other molecules from the same species (3) is expressed by a cell from a different species, or (4) does not occur in nature without human intervention. In other words, an "isolated antigen-binding protein" or "isolated antibody" is one which has been identified and separated and/or recovered from a component of its natural environment. Thus, a molecule that is chemically synthesized, or synthesized in a cellular system different from the cell from which it naturally originates, will be "isolated" from its naturally associated components. A molecule also can be rendered substantially free of naturally associated components by isolation, using purification techniques well known in the art. Molecule purity or homogeneity can be assayed by a number of means well known in the art. For example, the purity of a polypeptide sample can be assayed using polyacrylamide gel electrophoresis and staining of the gel to visualize the polypeptide using techniques well known in the art. For certain purposes, higher resolution can be provided by using HPLC or other means well known in the art for purification.

As used herein, a "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W.F1. Freeman and Company, New York (1984)); Introduction to Protein Structure (C. Branden and J. Tooze, eds., Garland Publishing, New York, N.Y. (1991)); and Thornton et al. Nature, 1991, 354: 105, which are each incorporated herein by reference.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5)

presentation of a polypeptide or protein on the cell surface; and (6) secretion or presentation or release of a polypeptide or protein from a cell.

As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple VH and VL domains). An exemplary linker sequence used in the present disclosure is GGGGSGGGGSGGGS (SEQ ID NO: 10).

As used herein, the terms "therapeutically effective" or "effective" refers to an amount of a peptide or composition provided herein effective to achieve a desired clinical effect. In some embodiments, the amount depends on the condition of a subject and the specific peptide administered. An effective amount varies with the nature of the condition being treated, the length of time that activity is desired, and the age and the condition of the subject, and ultimately is determined by the health care provider. In some aspects, an effective amount of an antigen-binding protein or fragment thereof according to the present disclosure is an amount effective to reduce or stop tumor growth.

As used herein, the term "immunoresponsive cells" refers to any cell that plays a role in the immune response. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

As used herein, the term "lymphocyte" refers to all immature, mature, undifferentiated and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, B-2 cells and anergic AN1/T3 cell populations.

As used herein, the term T-cell includes naïve T cells, CD4+ T cells, CD8+ T cells, memory T cells, activated T cells, anergic T cells, tolerant T cells, chimeric B cells, and antigen-specific T cells.

As used herein, the terms "B cell" or "B cells" refers to, by way of non-limiting example, a pre-B cell, progenitor B cell, early pro-B cell, late pro-B cell, large pre-B cell, small pre-B cell, immature B cell, mature B cell, naïve B cells, plasma B cells, activated B cells, anergic B cells, tolerant B cells, chimeric B cells, antigen-specific B cells, memory B cell, B-1 cell, B-2 cells and anergic AN1/T3 cell populations. In some embodiments, the term B cell includes a B cell that expresses an immunoglobulin heavy chain and/or light chain on its cells surface. In some embodiments, the term B cell includes a B cell that expresses and secretes an immunoglobulin heavy chain and/or light chain. In some embodiments, the term B cell includes a cell that binds an antigen on its cell-surface. In some embodiments disclosed herein, B cells or AN1/T3 cells are utilized in the processes described. In certain embodiments, such cells are optionally substituted with any animal cell suitable for expressing, capable of expressing (e.g., inducible expression), or capable of being differentiated into a cell suitable for expressing an antibody including, e.g., a hematopoietic stem cell, a naïve B cell, a B cell, a pre-B cell, a progenitor B cell, an early Pro-B cell, a late pro-B cell, a large pre-B cell, a small pre-B cell, an immature B cell, a mature B cell, a plasma B cell, a memory B cell, a B-1 cell, a B-2 cell, an anergic B cell, or an anergic AN1/T3 cell.

As used herein, an "adoptive cell therapeutic composition" refers to any composition comprising cells suitable for adoptive cell transfer. In exemplary embodiments, the adoptive cell therapeutic composition comprises a cell type selected from a group consisting of a tumor infiltrating lymphocyte (TIL), TCR (e.g., a heterologous T-cell receptor) modified lymphocytes and CAR (i.e., a chimeric antigen receptor) modified lymphocytes. In another embodiment, the adoptive cell therapeutic composition comprises a cell type selected from a group consisting of T-cells, CD8+ cells, CD4+ cells, NK-cells, delta-gamma T-cells, regulatory T-cells and peripheral blood mononuclear cells. In another embodiment, TILs, T-cells, CD8+ cells, CD4+ cells, NK-cells, delta-gamma T-cells, regulatory T-cells or peripheral blood mononuclear cells form the adoptive cell therapeutic composition. In one embodiment, the adoptive cell therapeutic composition comprises T cells.

As used herein, "tumor-infiltrating lymphocytes" or TILs refer to white blood cells that have left the bloodstream and migrated into a tumor.

As used herein, "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells)

As used herein, a "pathogen" refers to a virus, bacteria, fungi, parasite or protozoa capable of causing disease. Exemplary viruses include, but are not limited to, Retroviridae (e.g., human immunodeficiency viruses, such as HIV-1 (also referred to as HDTV-III, LAVE or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Naira viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Exemplary bacteria include, but are not limited to, *Pasteurella, Staphylococci, Streptococcus, Escherichia coli, Pseudomonas species*, and *Salmonella* species. Specific examples of infectious bacteria include but are not limited to, *Helicobacter pyloris, Borelia burgdorferi, Legionella pneumophilia, Mycobacteria* sps (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp *Fusobacterium nucleatum, Streptobacillus moniliformis, Treponema pallidium, Treponema pertenue, Leptospira, Rickettsia*, and *Actinomyces israelli*.

As used herein, "signal sequence" or "leader sequence" refers to a peptide sequence (5, 10, 15, 20, 25, 30 amino acids long) present at the N-terminus of newly synthesized proteins that directs their entry to the secretory pathway. Exemplary leader sequences include the CD8 leader sequence set forth in SEQ ID NO: 12 (canine).

As used herein, "specifically binds" refers to a polypeptide or fragment thereof that recognizes and binds a biological molecule of interest (e.g., a polypeptide), but which does not substantially recognize and bind other molecules in a sample, for example, a biological sample, which naturally includes a polypeptide of the present disclosure. For example, in some embodiments antibodies of the present disclosure specifically bind canine CD20. In this context "specifically binds" means that the antibody recognizes and binds to canine CD20 with greater affinity than to other, non-specific molecules that are not canine CD20. For example, an antibody raised against an antigen (polypeptide) to which it binds more efficiently than to a non-specific antigen (e.g., a canine protein that is not related to or homologous to CD20) can be described as specifically binding to the antigen. Binding specificity can be tested using, for example, an enzyme-linked immunosorbent assay (ELISA), a radioimmunoassay (MA), or a western blot assay using methodology well known in the art.

As used herein, the term "tumor antigen" refers to an antigen (e.g., a polypeptide) that is uniquely or differentially expressed on a tumor cell compared to a normal cell. With reference to the present disclosure, a tumor antigen includes any polypeptide expressed by a tumor that is capable of activating or inducing an immune response via an antigen recognizing receptor (e.g., CD20).

As used herein, the term "virus antigen" refers to a polypeptide expressed by a virus that is capable of inducing an immune response.

As used herein, the terms "comprises", "comprising", and are intended to have the broad meaning ascribed to them in U.S. Patent Law and can mean "includes", "including" and the like.

As used herein, the terms "patient," "subject," "individual," and the like are used interchangeably herein, and refer to an animal, typically a mammal. In a one embodiment, the patient, subject, or individual is a mammal. In one embodiment, the patient, subject or individual is in the canine family, such as domestic dogs, wolves, foxes, jackals, dingoes.

As used herein, the terms "treating" or "treatment" refers to the treatment of a disease in a subject, such as a human, and includes: (i) inhibiting a disease, i.e., arresting its development; (ii) relieving a disease, i.e., causing regression of the disease; (iii) slowing progression of the disease; and/or (iv) inhibiting, relieving, or slowing progression of one or more symptoms of the disease. With respect to a cancer, "treating" or "treatment" also encompasses regression of a tumor, slowing tumor growth, inhibiting metastasis of a tumor, inhibiting relapse or recurrent cancer and/or maintaining remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment can be a continuous prolonged treatment for a chronic disease or a single, or few time administrations for the treatment of an acute condition.

As used herein, the term "therapeutic" refers to a treatment and/or prophylaxis. A therapeutic effect is obtained by suppression, remission, or eradication of a disease state.

Overview

There are various methods that can be employed to raise an antibody against a protein or peptide antigen. Traditional methods of antibody generation are based on digests of proteins to produce peptide antigens, which produce mixtures of antibodies that are purified from bleeds of immunized animals. Other methods involve the generation of multiple synthetic linear peptides that are conjugated to carrier protein for immunization. Monoclonal antibodies can then be subsequently purified in a complex activity-guided affinity chromatography. In all of the above methods, the determination of the antigen sequence is rather cumbersome and in most cases left unknown. Provided herein is an improved method which takes into account the three dimensional protein structure.

In the present disclosure, the structure of the canine CD20 extracellular domain was analyzed and used to recreate a three dimensional canine CD20 antigen for immunization. Based on this analysis, a canine extracellular CD20 sequence was chemically synthesized in high purity, conjugated to a carrier protein, and inoculated in a suitable animal model for production of CD20 specific antibodies. Unlike other strategies, chemical synthesis provided the cyclized extracellular sequence in a pure form with a structure that is close to the native extracellular conformation of CD20, which in turn provided an improved anti-CD20 antibody. Accordingly, the methods provided herein using the synthetic CD20 peptide epitope produce high affinity antibodies to anti-CD20. In some embodiments, the synthetic CD20 peptide epitope can also be used as an affinity reagent by covalently attaching it to a solid surface, such as a bio-bead or a plate. In some embodiments, attachment is through the same chemistry which was used for conjugation to carrier protein. This allows for necessary quality control assays, such as an ELISA.

Once isolated, the high affinity anti-CD20 antibodies or CD20 binding fragments thereof, e.g., anti-CD20 antibodies or CD20 binding fragments that bind canine CD20 as provided herein, can be employed in diagnostic and therapeutic methods as described in further detail herein. In addition, the anti-CD20 antibodies or CD20 binding fragments can be modified as described herein to generate fusion proteins, including chimeric antigen receptors for adoptive cell therapy, using the nucleic acid sequence encoding the anti-CD20 antibodies or CD20 binding fragments thereof. As described herein in the examples, chimeric antigen receptors were constructed using the heavy and light chain antigen binding portions of an anti-CD20 antibody generated using the cyclized canine CD20 antigen as described herein. As demonstrated herein, T cells expressing these chimeric antigen receptors are able to specifically target and kill CD20 expressing tumor cells in vitro and in vivo. Accordingly, the anti-CD20 antibodies or CD20 binding fragments thereof are effective for the treatment of CD20 associated cancers, such as B cell lymphomas and leukemias.

Generation of an Exemplary CD20 Antigen for Antibody Production

Figure 2:
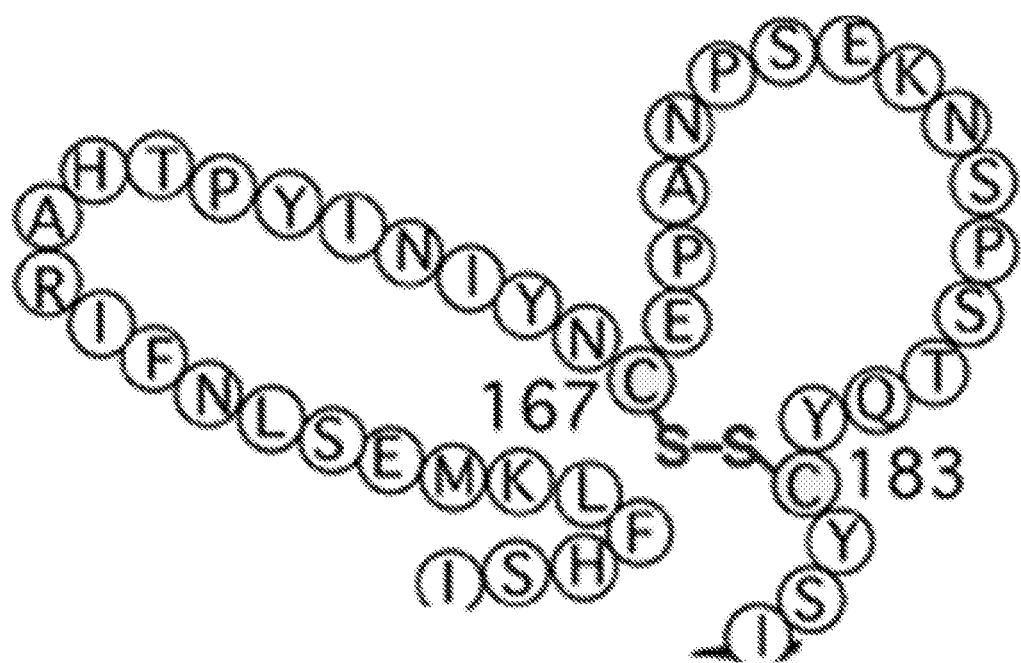
FIG. 2 illustrates the extracellular portion of human CD20 (SEQ ID NO: 60).

CD20 is an activated-glycosylated phosphoprotein expressed on the surface of all B-cells. CD20 is a membrane-spanning four helix protein with both C and N termini located on the cytoplasmic side in a manner protruding from two of four trans-membrane helices (FIG. 1). On the extracellular domain, there are two loops with the smaller loop composed of amino acids starting at cysteine 167 through cysteine 183 (positions referring to human CD20). Together these two cysteines unite through their sulfhydryl side chains by forming a sulfur-sulfur bridge that closes the ring (FIG. 2). The folding and presentation of the small loop is crucial to recognition by many therapeutic antibodies such as rituximab and its biosimilars.

The present disclosure provides antigen-binding proteins, for example, antibodies, fragments and derivatives thereof, which specifically bind to a CD20 extracellular domain. The extracellular sequences of canine (SEQ ID NO:1), human (SEQ ID NO:2), and mouse (SEQ ID NO:3) CD20 (FIG. 3, Table 1) show a high degree of similarity though not complete identity. Therefore, anti-CD20 antibodies developed to one species have a likelihood of interspecies overlap in antibody recognition and can be used for comparative studies. In one embodiment, the antigen-binding protein of the present disclosure specifically binds to the extracellular domain of canine CD20 (SEQ ID NO: 1).

Unless otherwise indicated, each polypeptide sequence provided herein has an amino terminus at the left and a carboxyl terminus at the right. Polypeptide sequences are indicated using standard one-letter abbreviations.

In some embodiments, the CD20 antigen is canine CD20 cyclic peptide comprising a CD20 epitope sequence: YVDIHNCDPANPSEKNSLSIQYC (SEQ ID NO: 20), representing a portion of the canine CD20 extracellular domain of SEQ ID NO:2, in particular, the smaller loop of canine CD20 extracellular domain and six additional amino acids of the larger loop of canine CD20 extracellular domain. In some embodiments, the CD20 antigen is canine CD20 cyclic peptide, wherein the CD20 portion of the antigen consists of the sequence: YVDIHNCDPANPSEKNSLSIQYC (SEQ ID NO: 20). In some embodiments, the canine CD20 cyclic peptide comprises the sequence of SEQ ID NO: 20, wherein the cysteine at position 7 of SEQ ID NO: 20 forms a disulfide bond with the cysteine at position 23 of SEQ ID NO: 20.

In exemplary methods, the canine CD20 epitope sequence for the antigen construct includes the 17 amino acids of the smaller extracellular loop of canine CD20 and extended six additional amino acids into the larger extracellular loop: YVDIHNCDPANPSEKNSLSIQYC (SEQ ID NO: 20). The presence of the ring and formation of a partial secondary structure is intended mimic that of native extracellular loop of CD20. This allows for antibody recognition that is conformational as opposed to linear as in the case of the linear 16 amino acid epitope for rituximab (YNCEPANPSEKNSPST (SEQ ID NO: 21)).

In some embodiments, additional design elements are included in the CD20 antigen synthesis procedure to facilitate the chemical synthesis of the antigen construct and/or focus immunogenicity on the CD20 epitope sequence rather than the spacer elements. For example, in some embodiments, the N-terminal amino acid in the construct is kept as a free amino group instead of an acetylated N-terminus in order to give an advantage to immunogenicity towards N-acetylated termini. In some embodiments, a spacer, such as a small neutral peptide sequence, can be inserted on the C terminal side of the CD20 epitope sequence to insure proper separation and presentation by a carrier protein (e.g., keyhole limpet hemocyanin (KLH)). In some embodiments, the spacer sequence is composed of a series of glycine and serine residues. In an exemplary embodiment, the spacer sequence of Gly-Ser-Gly-Gly-Gly (SEQ ID NO: 58) is employed. In some embodiments, the peptide terminates in a lysine to facilitate linking chemistry to a carrier protein (e.g., KLH) or other molecules. In some embodiments, the

TABLE 1

| | | Sequence | SEQ ID NO |
|---|---|---|---|
| CD20 Extracellular domain | canine | NITISHFFKMENLNLIKAPMPYVDIHNCDPANPSEKN SLSIQYCGS | 1 |
| | human | NIKISHFLKMESLNFIRAHTPYINIYNCEPANPSEKNS PSTQYCYS | 2 |
| | mouse | NMTLSHFLKMRSLNFIRAHTPYINIYNCEPANPSEKN SPSTQYCNS | 3 |

In some embodiments, the antigen-binding proteins are generated by immunization of subject with a CD20 antigen provided herein. In some embodiments, the CD20 antigen is derived from an extracellular domain of a CD20 protein, for example, a canine, human or mouse CD20 extracellular domain. In particular embodiments, the CD20 antigen is derived from the canine CD20 extracellular domain of SEQ ID NO:2. In particular embodiments, the CD20 antigen comprises a portion of the canine CD20 extracellular domain of SEQ ID NO:2.

Figure 4:
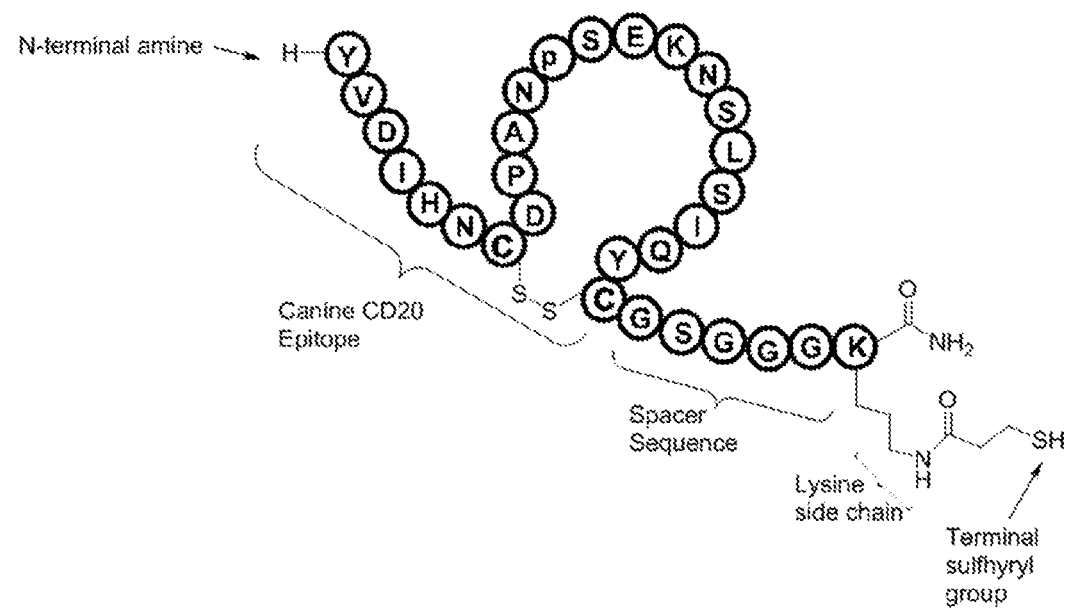
FIG. 4 illustrates canine CD20 epitope design comprising the canine CD20 epitope (SEQ ID NO: 20) and the space sequence (SEQ ID NO: 52).

C-terminal lysine is further linked to a terminal sulfhydryl group to facilitate linking chemistry to a carrier protein (e.g., KLH) or other molecules. FIG. 4 illustrates an exemplary canine CD20 antigen construct prior to attachment of the carrier protein. In some embodiments, the carrier protein such as KLH is used without attachment of an artificial immunogenic group such as a polyethylene glycol (PEG) or the like. In some embodiments, the carrier protein such as KLH is used with attachment of an artificial immunogenic group such as a polyethylene glycol (PEG) or the like.

The number of sulfhydryl groups present on the CD20 epitope and their structural arrangement vis-a-vis the small extracellular loop and its correct formation and consequent conformation presents a challenge to chemical synthesis of the antigen. In particular, there are two sulfhydryl groups emanating from the two cysteine side chains at positions 7 and 23 of SEQ ID NO:20 (i.e. cysteines 167 and 183 of the full-length CD20), which must form the extracellular loop, and a terminal sulfhydryl, which is used for linking to KLH. Together, the three sulfhydryl groups have the tendency to scramble at oxidation or cyclization step should they be liberated at the same time and could form a multitude of cyclic peptides as well as linear polymers connected through S—S bonds. Therefore, in some embodiments, the synthesis steps and protecting group strategy are planned such that only the two cysteine side chains are released for cyclization in a synchronous manner with the terminal sulfhydryl protected during cyclization reaction.

Figure 5:
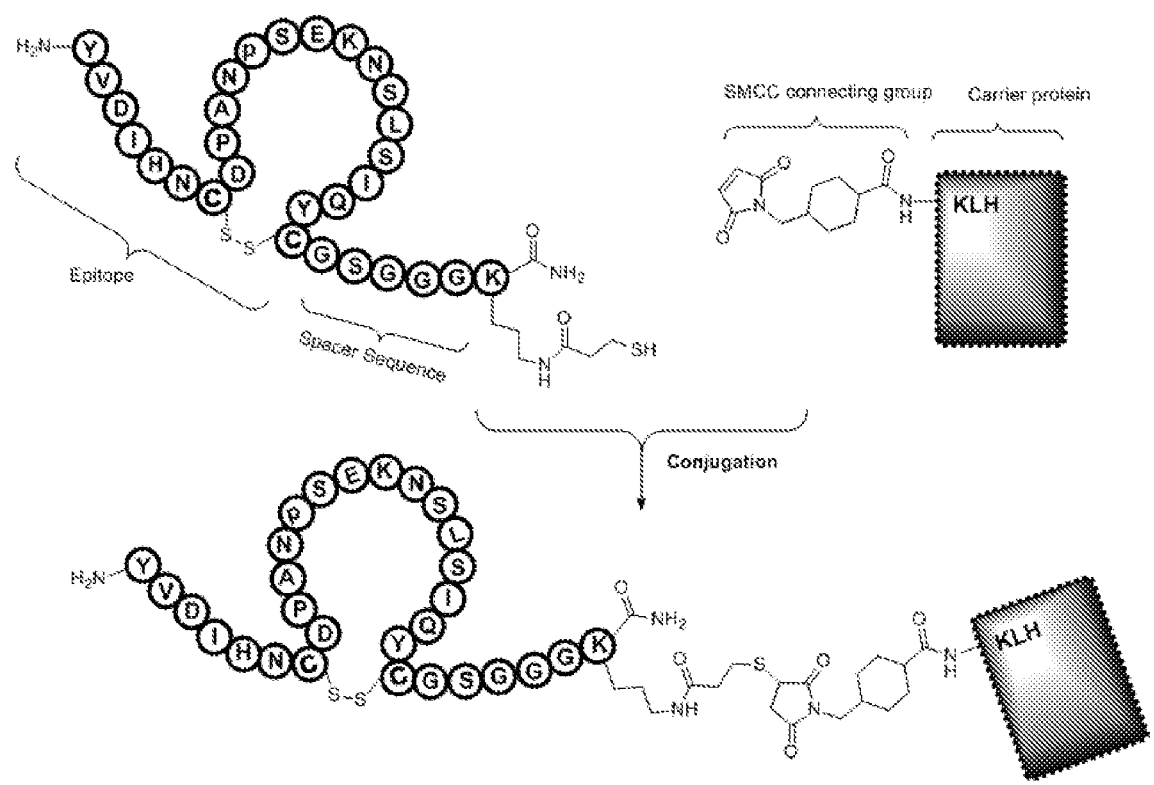
FIG. 5 illustrates an exemplary schema for conjugation of the prepared canine CD20 antigen comprising the canine CD20 epitope (SEQ ID NO: 20) and the space sequence (SEQ ID NO: 52) to carrier protein KLH.

In some embodiments, an additional connecting group is used to connect the terminal sulfhydryl group to KLH. The additional connecting group also provides further flexibility as well as ease of synthesis by offering a better protecting group control, for example, in order to execute on-bead transformations prior to release of the full construct. In some embodiments, a lysine with an orthogonal protecting group, such as Dde (1-(4,4-dimethyl-2,6,-dioxocyclohex-1-ylidene)ethyl, at its side chain can be removed on-bead without deprotecting the other amino acids side chains. Once the lysine side chain is released from Dde protecting group, an S-trityl mercapto propionic acid can be connected to the liberated ε-amino group resulting in the full construct on-bead. Selective oxidation of cysteines 167 and 183 and final deblocking of the whole sequence under non-reducing conditions results in generation of the crude construct. This crude construction can then be precipitated and purified to a high level (e.g., 99+%). In some embodiments, the fractions containing the product can then be lyophilized. In some embodiments, the fractions containing the product can then be conjugated to KLH, for example, KLH preactivated with a cross-linker such as Sulfo-SMCC (sulfosuccinimidyl 4-(N-maleimidomethyl)cyclohexane-1-carboxylate) (FIG. 5).

In some embodiments, the KLH conjugated CD20 antigen is then used to inoculate a suitable host for antibody production. Generally, antibodies are produced by immunizing an animal (e.g., a rodent or domesticated animal) with the CD20 antigen, obtaining antibody-producing cells from the animal (e.g., by harvesting splenocytes from an animal identified as producing antibodies following inoculation), and fusing the antibody-producing cells with strains of myeloma cells, e.g., tumor cells, to produce hybridomas which are isolated and cultured as monoclones. The monoclonal hybridomas can either be cultured in vitro or can be grown as tumors in a host animal. Because each antibody-producing cell produces a single unique antibody, the monoclonal cultures of hybridomas each produce a homogeneous antibody which may be obtained either from the culture medium of hybridoma cultures grown in vitro or from the cells, ascitic fluid, or serum of a tumor-bearing host animal. Once a monoclonal hybridoma is identified, the nucleic acid sequences encoding the heavy chain and light chains of the antibody can be cloned using standard techniques and further manipulated to produce the antigen-binding proteins provided herein.

CD20 Antigen Binding Sequences

The present disclosure provides antigen-binding proteins, for example, antibodies, fragments and derivatives thereof, which specifically bind to a CD20 extracellular domain. In some embodiments the antigen-binding proteins specifically bind to a canine, human, or mouse CD20 extracellular domain. In some embodiments the antigen-binding proteins specifically bind to a CD20 extracellular domain having the sequence of SEQ ID NO: 1, 2, or 3 as shown in Table 1. In particular embodiments, the antigen-binding proteins specifically bind to a canine CD20 extracellular domain. In particular embodiments, the antigen-binding proteins specifically bind to a canine CD20 extracellular domain of SEQ ID NO:1. In some embodiments the antigen-binding proteins are generated by inoculating a suitable host animal with a canine CD20 cyclic peptide having the sequence of SEQ ID NO: 20. In some embodiments, the canine CD20 cyclic peptide comprises the sequence of SEQ ID NO: 20, wherein the cysteine at position 7 of SEQ ID NO: 20 forms a disulfide bond with the cysteine at position 23 of SEQ ID NO: 20. In some embodiments the antigen-binding proteins bind with higher affinity to a CD20 extracellular domain having the sequence of SEQ ID NO: 1 as compared to an anti-CD20 antibody generated by using a linear CD20 peptide antigen.

In certain embodiments, the present disclosure provides antigen-binding proteins, for example, antibodies, fragments and derivatives thereof and fusion proteins comprising amino acid sequences, or encoded by the nucleic acid sequences described in Table 2. For example, provided are antigen-binding proteins, for example, antibodies, fragments and derivatives thereof and fusion proteins comprising a variable heavy chain (VH) of SEQ ID NO: 4 and/or a variable light chain (VL) of SEQ ID NO: 6. In some embodiments, provided is an antibody or an antigen binding fragment thereof comprising a variable heavy chain (VH) of SEQ ID NO: 4 or a variable heavy chain (VH) having at least 80%, 90%, 91%, 92%, 93%, 94%, 95%, 96%, 97%, 98%, 99% or more sequence identity with SEQ ID NO: 4. In some embodiments, provided is an antibody or an antigen binding fragment thereof comprising a variable light chain (VL) of SEQ ID NO: 6 or a variable light chain (VL) having at least 80%, 90%, 91%, 92%, 93%, 94%, 95%, 96%, 97%, 98%, 99% or more sequence identity with SEQ ID NO: 6.

In some embodiments, provided is an antibody or antigen binding fragment thereof comprising (a) a variable light chain (VL) complementarity determining region (CDR) 1 of SEQ ID NO: 46 or a VL CDR1 having at least 80%, 90%, 91%, 92%, 93%, 94%, 95%, 96%, 97%, 98%, 99% or more sequence identity with SEQ ID NO: 46; (b) a variable light chain (VL) complementarity determining region (CDR) 2 of SEQ ID NO: 48 or a VL CDR2 having at least 80%, 90%, 91%, 92%, 93%, 94%, 95%, 96%, 97%, 98%, 99% or more sequence identity with SEQ ID NO: 48; and/or (c) a variable light chain (VL) complementarity determining region (CDR) 3 of SEQ ID NO: 50 or a VL CDR3 having at least 80%, 90%, 91%, 92%, 93%, 94%, 95%, 96%, 97%, 98%, 99% or more sequence identity with SEQ ID NO: 50. In some embodiments, provided is an antibody or antigen binding fragment thereof comprising a variable light chain (VL) complementarity determining region (CDR) 1 of SEQ ID NO: 46 or a VL CDR1 having at least 80%, 90%, 91%, 92%, 93%, 94%, 95%, 96%, 97%, 98%, 99% or more sequence identity with SEQ ID NO: 46. In some embodiments, provided is an antibody or antigen binding fragment thereof comprising a variable light chain (VL) complementarity determining region (CDR) 2 of SEQ ID NO: 48 or a VL CDR2 having at least 80%, 90%, 91%, 92%, 93%, 94%, 95%, 96%, 97%, 98%, 99% or more sequence identity with SEQ ID NO: 48. In some embodiments, provided is an antibody or antigen binding fragment thereof comprising a variable light chain (VL) complementarity determining region (CDR) 3 of SEQ ID NO: 50 or a VL CDR3 having at least 80%, 90%, 91%, 92%, 93%, 94%, 95%, 96%, 97%, 98%, 99% or more sequence identity with SEQ ID NO: 50.

In some embodiments, provided is an antibody or antigen binding fragment thereof comprising (a) a variable heavy chain (VH) complementarity determining region (CDR) 1 of SEQ ID NO: 40 or a VH CDR1 having at least 80%, 90%, 91%, 92%, 93%, 94%, 95%, 96%, 97%, 98%, 99% or more sequence identity with SEQ ID NO: 40; (b) a variable heavy chain (VH) complementarity determining region (CDR) 2 of SEQ ID NO: 42 or a VH CDR2 having at least 80%, 90%, 91%, 92%, 93%, 94%, 95%, 96%, 97%, 98%, 99% or more sequence identity with SEQ ID NO: 42; and/or (c) a variable heavy chain (VH) complementarity determining region (CDR) 3 consisting of a threonine (T) residue. In some embodiments, provided is an antibody or antigen binding fragment thereof comprising a variable heavy chain (VH) complementarity determining region (CDR) 1 of SEQ ID NO: 40 or a VH CDR1 having at least 80%, 90%, 91%, 92%, 93%, 94%, 95%, 96%, 97%, 98%, 99% or more sequence identity with SEQ ID NO: 40. In some embodiments, provided is an antibody or antigen binding fragment thereof comprising a variable heavy chain (VH) complementarity determining region (CDR) 2 of SEQ ID NO: 42 or a VH CDR2 having at least 80%, 90%, 91%, 92%, 93%, 94%, 95%, 96%, 97%, 98%, 99% or more sequence identity with SEQ ID NO: 42. In some embodiments, provided is an antibody or antigen binding fragment thereof comprising a variable heavy chain (VH) complementarity determining region (CDR) 3 consisting of a threonine (T) residue.

In some embodiments, provided is an antibody or antigen binding fragment thereof comprising (a) a variable light chain (VL) comprising (i) a complementarity determining region (CDR) 1 of SEQ ID NO: 46 or a CDR1 having at least 80%, 90%, 91%, 92%, 93%, 94%, 95%, 96%, 97%, 98%, 99% or more sequence identity with SEQ ID NO: 46; (ii) a CDR2 of SEQ ID NO: 48 or a CDR2 having at least 80%, 90%, 91%, 92%, 93%, 94%, 95%, 96%, 97%, 98%, 99% or more sequence identity with SEQ ID NO: 48; and/or (iii) a CDR3 of SEQ ID NO: 50 or a CDR3 having at least 80%, 90%, 91%, 92%, 93%, 94%, 95%, 96%, 97%, 98%, 99% or more sequence identity with SEQ ID NO: 50; and (b) a variable heavy chain (VH) of SEQ ID NO: 4 or a variable heavy chain (VH) having at least 80%, 90%, 91%, 92%, 93%, 94%, 95%, 96%, 97%, 98%, 99% or more sequence identity with SEQ ID NO: 4.

In some embodiments, provided is an antibody or antigen binding fragment thereof comprising (a) a variable light chain (VL) of SEQ ID NO: 6 or a variable light chain (VL) having at least 80%, 90%, 91%, 92%, 93%, 94%, 95%, 96%, 97%, 98%, 99% or more sequence identity with SEQ ID NO: 6; and (b) a variable heavy chain (VH) comprising (i) a complementarity determining region (CDR) 1 of SEQ ID NO: 40 or a CDR1 having at least 80%, 90%, 91%, 92%, 93%, 94%, 95%, 96%, 97%, 98%, 99% or more sequence identity with SEQ ID NO: 40; (ii) a CDR2 of SEQ ID NO: 42 or a CDR2 having at least 80%, 90%, 91%, 92%, 93%, 94%, 95%, 96%, 97%, 98%, 99% or more sequence identity with SEQ ID NO: 42; and/or (ii) a CDR3 consisting of a threonine (T) residue.

In some embodiments, provided is an antibody or antigen binding fragment thereof comprising (a) a variable light chain (VL) comprising (i) a complementarity determining region (CDR) 1 of SEQ ID NO: 46 or a CDR1 having at least 80%, 90%, 91%, 92%, 93%, 94%, 95%, 96%, 97%, 98%, 99% or more sequence identity with SEQ ID NO: 46; (ii) a CDR2 of SEQ ID NO: 48 or a CDR2 having at least 80%, 90%, 91%, 92%, 93%, 94%, 95%, 96%, 97%, 98%, 99% or more sequence identity with SEQ ID NO: 48; and/or (iii) a CDR3 of SEQ ID NO: 50 or a CDR3 having at least 80%, 90%, 91%, 92%, 93%, 94%, 95%, 96%, 97%, 98%, 99% or more sequence identity with SEQ ID NO: 50; and (b) a variable heavy chain (VH) comprising (i) a complementarity determining region (CDR) 1 of SEQ ID NO: 40 or a CDR1 having at least 80%, 90%, 91%, 92%, 93%, 94%, 95%, 96%, 97%, 98%, 99% or more sequence identity with SEQ ID NO: 40; (ii) a CDR2 of SEQ ID NO: 42 or a CDR2 having at least 80%, 90%, 91%, 92%, 93%, 94%, 95%, 96%, 97%, 98%, 99% or more sequence identity with SEQ ID NO: 42; and/or (ii) a CDR3 consisting of a threonine (T) residue.

In some embodiments, provided are antigen-binding proteins, for example, antibodies, fragments and derivatives thereof and fusion proteins comprising a variable heavy chain (VH) encoded by the nucleic acid of SEQ ID NO: 5 and/or a variable light chain (VL) encoded by the nucleic acid of SEQ ID NO:7. In some embodiments, provided is an antibody or an antigen binding fragment thereof comprising a variable heavy chain (VH) encoded by the nucleic acid having at least 80%, 90%, 91%, 92%, 93%, 94%, 95%, 96%, 97%, 98%, 99% or more sequence identity with SEQ ID NO: 5. In some embodiments, provided is an antibody or an antigen binding fragment thereof comprising a variable light chain (VL) encoded by the nucleic acid having at least 80%, 90%, 91%, 92%, 93%, 94%, 95%, 96%, 97%, 98%, 99% or more sequence identity with SEQ ID NO: 7.

In some embodiments, provided is an antibody or antigen binding fragment thereof comprising (a) a variable light chain (VL) complementarity determining region (CDR) 1 encoded by the nucleic acid of SEQ ID NO: 47 or a VL CDR1 encoded by the nucleic acid having at least 80%, 90%, 91%, 92%, 93%, 94%, 95%, 96%, 97%, 98%, 99% or more sequence identity with SEQ ID NO: 47; (b) a variable light chain (VL) complementarity determining region (CDR) 2 encoded by the nucleic acid of SEQ ID NO: 49 or a VL CDR2 encoded by the nucleic acid having at least 80%, 90%, 91%, 92%, 93%, 94%, 95%, 96%, 97%, 98%, 99% or more sequence identity with SEQ ID NO: 49; and/or (c) a variable light chain (VL) complementarity determining region (CDR) 3 encoded by the nucleic acid of SEQ ID NO: 51 or a VL CDR3 encoded by the nucleic acid having at least 80%, 90%, 91%, 92%, 93%, 94%, 95%, 96%, 97%, 98%, 99% or more sequence identity with SEQ ID NO: 51. In some embodiments, provided is an antibody or antigen binding fragment thereof comprising a variable light chain (VL) complementarity determining region (CDR) 1 encoded by the nucleic acid of SEQ ID NO: 47 or a VL CDR1 encoded by the nucleic acid having at least 80%, 90%, 91%, 92%, 93%, 94%, 95%, 96%, 97%, 98%, 99% or more sequence identity with SEQ ID NO: 47. In some embodiments, provided is an antibody or antigen binding fragment thereof comprising a variable light chain (VL) complementarity determining region (CDR) 2 encoded by the nucleic acid of SEQ ID NO: 49 or a VL CDR2 encoded by the nucleic acid having at least 80%, 90%, 91%, 92%, 93%, 94%, 95%, 96%, 97%, 98%, 99% or more sequence identity with SEQ ID NO: 49. In some embodiments, provided is an antibody or antigen binding fragment thereof comprising a variable light chain (VL) complementarity determining region (CDR) 3 encoded by the nucleic acid of SEQ ID NO: 51 or a VL CDR3 encoded by the nucleic acid having at least 80%, 90%, 91%, 92%, 93%, 94%, 95%, 96%, 97%, 98%, 99% or more sequence identity with SEQ ID NO: 51.

In some embodiments, provided is an antibody or antigen binding fragment thereof comprising (a) a variable heavy chain (VH) complementarity determining region (CDR) 1 encoded by the nucleic acid of SEQ ID NO: 41 or a VH CDR1 encoded by the nucleic acid having at least 80%, 90%, 91%, 92%, 93%, 94%, 95%, 96%, 97%, 98%, 99% or more sequence identity with SEQ ID NO: 41; (b) a variable heavy chain (VH) complementarity determining region (CDR) 2 encoded by the nucleic acid of SEQ ID NO: 43 or a VH CDR2 encoded by the nucleic acid having at least 80%, 90%, 91%, 92%, 93%, 94%, 95%, 96%, 97%, 98%, 99% or more sequence identity with SEQ ID NO: 43; and/or (c) a variable heavy chain (VH) complementarity determining region (CDR) 3 encoded by the nucleic acid consisting of SEQ ID NO: 45. In some embodiments, provided is an antibody or antigen binding fragment thereof comprising a variable heavy chain (VH) complementarity determining region (CDR) 1 encoded by the nucleic acid of SEQ ID NO: 41 or a VH CDR1 encoded by the nucleic acid having at least 80%, 90%, 91%, 92%, 93%, 94%, 95%, 96%, 97%, 98%, 99% or more sequence identity with SEQ ID NO: 41. In some embodiments, provided is an antibody or antigen binding fragment thereof comprising a variable heavy chain (VH) complementarity determining region (CDR) 2 encoded by the nucleic acid of SEQ ID NO: 43 or a VH CDR2 encoded by the nucleic acid having at least 80%, 90%, 91%, 92%, 93%, 94%, 95%, 96%, 97%, 98%, 99% or more sequence identity with SEQ ID NO: 43. In some embodiments, provided is an antibody or antigen binding fragment thereof comprising a variable heavy chain (VH) complementarity determining region (CDR) 3 encoded by the nucleic acid consisting of SEQ ID NO: 45.

In some embodiments, provided is an antibody or antigen binding fragment thereof comprising (a) a variable light chain (VL) comprising (i) a complementarity determining region (CDR) 1 encoded by the nucleic acid of SEQ ID NO: 47 or a CDR1 encoded by the nucleic acid having at least 80%, 90%, 91%, 92%, 93%, 94%, 95%, 96%, 97%, 98%, 99% or more sequence identity with SEQ ID NO: 47; (ii) a CDR2 encoded by the nucleic acid of SEQ ID NO: 49 or a CDR2 encoded by the nucleic acid having at least 80%, 90%, 91%, 92%, 93%, 94%, 95%, 96%, 97%, 98%, 99% or more sequence identity with SEQ ID NO: 49; and/or (iii) a CDR3 encoded by the nucleic acid of SEQ ID NO: 51 or a CDR3 encoded by the nucleic acid having at least 80%, 90%, 91%, 92%, 93%, 94%, 95%, 96%, 97%, 98%, 99% or more sequence identity with SEQ ID NO: 51; and (b) a variable heavy chain (VH) encoded by the nucleic acid of SEQ ID NO: 5 or a variable heavy chain (VH) encoded by the nucleic acid having at least 80%, 90%, 91%, 92%, 93%, 94%, 95%, 96%, 97%, 98%, 99% or more sequence identity with SEQ ID NO: 5.

In some embodiments, provided is an antibody or antigen binding fragment thereof comprising (a) a variable light chain (VL) encoded by the nucleic acid of SEQ ID NO: 7 or a variable light chain (VL) encoded by the nucleic acid having at least 80%, 90%, 91%, 92%, 93%, 94%, 95%, 96%, 97%, 98%, 99% or more sequence identity with SEQ ID NO: 7; and (b) a variable heavy chain (VH) comprising (i) a complementarity determining region (CDR) 1 encoded by the nucleic acid of SEQ ID NO: 41 or a CDR1 encoded by the nucleic acid having at least 80%, 90%, 91%, 92%, 93%, 94%, 95%, 96%, 97%, 98%, 99% or more sequence identity with SEQ ID NO: 41; (ii) a CDR2 encoded by the nucleic acid of SEQ ID NO: 43 or a CDR2 encoded by the nucleic acid having at least 80%, 90%, 91%, 92%, 93%, 94%, 95%, 96%, 97%, 98%, 99% or more sequence identity with SEQ ID NO: 43; and/or (ii) a CDR3 encoded by the nucleic acid consisting of SEQ ID NO: 45.

In some embodiments, provided is an antibody or antigen binding fragment thereof comprising (a) a variable light chain (VL) comprising (i) a complementarity determining region (CDR) 1 encoded by the nucleic acid of SEQ ID NO: 47 or a CDR1 encoded by the nucleic acid having at least 80%, 90%, 91%, 92%, 93%, 94%, 95%, 96%, 97%, 98%, 99% or more sequence identity with SEQ ID NO: 47; (ii) a CDR2 encoded by the nucleic acid of SEQ ID NO: 49 or a CDR2 encoded by the nucleic acid having at least 80%, 90%, 91%, 92%, 93%, 94%, 95%, 96%, 97%, 98%, 99% or more sequence identity with SEQ ID NO: 49; and/or (iii) a CDR3 encoded by the nucleic acid of SEQ ID NO: 51 or a CDR3 encoded by the nucleic acid having at least 80%, 90%, 91%, 92%, 93%, 94%, 95%, 96%, 97%, 98%, 99% or more sequence identity with SEQ ID NO: 51; and (b) a variable heavy chain (VH) comprising (i) a complementarity determining region (CDR) 1 encoded by the nucleic acid of SEQ ID NO: 41 or a CDR1 encoded by the nucleic acid having at least 80%, 90%, 91%, 92%, 93%, 94%, 95%, 96%, 97%, 98%, 99% or more sequence identity with SEQ ID NO: 41; (ii) a CDR2 encoded by the nucleic acid of SEQ ID NO: 43 or a CDR2 encoded by the nucleic acid having at least 80%, 90%, 91%, 92%, 93%, 94%, 95%, 96%, 97%, 98%, 99% or more sequence identity with SEQ ID NO: 43; and/or (ii) a CDR3 encoded by the nucleic acid consisting of SEQ ID NO: 45.

In some embodiments, provided is a single chain variable fragment (scFv) comprising a heavy chain variable chain of SEQ ID NO: 4 or a variable heavy chain (VH) having at least 80%, 90%, 91%, 92%, 93%, 94%, 95%, 96%, 97%, 98%, 99% or more sequence identity with SEQ ID NO: 4 and/or a light chain variable chain of SEQ ID NO: 6. In some embodiments, provided is a single chain variable fragment (scFv) comprising a heavy chain variable chain of SEQ ID NO: 4 and/or a light chain variable chain of SEQ ID NO: 6 or a variable light chain (VL) having at least 80%, 90%, 91%, 92%, 93%, 94%, 95%, 96%, 97%, 98%, 99% or more sequence identity with SEQ ID NO: 6. In some embodiments, the scFv has an amino acid sequence of SEQ ID NO: 8, or is encoded by the nucleic acid of SEQ ID NO: 9. In some embodiments, the scFv has an amino acid sequence that has at least 80%, 90%, 91%, 92%, 93%, 94%, 95%, 96%, 97%, 98%, 99% or more sequence identity with SEQ ID NO: 8. In some embodiments, the scFv is encoded by the nucleic acid of SEQ ID NO: 9 or a CDR2 encoded by the nucleic acid having at least 80%, 90%, 91%, 92%, 93%, 94%, 95%, 96%, 97%, 98%, 99% or more sequence identity with SEQ ID NO: 9. In some embodiments, the scFv has a linker sequence that joins the VH and VL chains. In some embodiments, the linker sequence has an amino acid sequence of SEQ ID NO: 10, or is encoded by the nucleic acid of SEQ ID NO: 11.

In some embodiments, provided is a single chain variable fragment (scFv) comprising (a) a variable light chain (VL) complementarity determining region (CDR) 1 of SEQ ID NO: 46 or a VL CDR1 having at least 80%, 90%, 91%, 92%, 93%, 94%, 95%, 96%, 97%, 98%, 99% or more sequence identity with SEQ ID NO: 46; (b) a variable light chain (VL) complementarity determining region (CDR) 2 of SEQ ID NO: 48 or a VL CDR2 having at least 80%, 90%, 91%, 92%, 93%, 94%, 95%, 96%, 97%, 98%, 99% or more sequence identity with SEQ ID NO: 48; and/or (c) a variable light chain (VL) complementarity determining region (CDR) 3 of SEQ ID NO: 50 or a VL CDR3 having at least 80%, 90%, 91%, 92%, 93%, 94%, 95%, 96%, 97%, 98%, 99% or more sequence identity with SEQ ID NO: 50. In some embodiments, provided is a single chain variable fragment (scFv) comprising a variable light chain (VL) complementarity determining region (CDR) 1 of SEQ ID NO: 46 or a VL CDR1 having at least 80%, 90%, 91%, 92%, 93%, 94%, 95%, 96%, 97%, 98%, 99% or more sequence identity with SEQ ID NO: 46. In some embodiments, provided is a single chain variable fragment (scFv) comprising a variable light chain (VL) complementarity determining region (CDR) 2 of SEQ ID NO: 48 or a VL CDR2 having at least 80%, 90%, 91%, 92%, 93%, 94%, 95%, 96%, 97%, 98%, 99% or more sequence identity with SEQ ID NO: 48. In some embodiments, provided is a single chain variable fragment (scFv) comprising a variable light chain (VL) complementarity determining region (CDR) 3 of SEQ ID NO: 50 or a VL CDR3 having at least 80%, 90%, 91%, 92%, 93%, 94%, 95%, 96%, 97%, 98%, 99% or more sequence identity with SEQ ID NO: 50.

In some embodiments, provided is a single chain variable fragment (scFv) comprising (a) a variable heavy chain (VH) complementarity determining region (CDR) 1 of SEQ ID NO: 40 or a VH CDR1 having at least 80%, 90%, 91%, 92%, 93%, 94%, 95%, 96%, 97%, 98%, 99% or more sequence identity with SEQ ID NO: 40; (b) a variable heavy chain (VH) complementarity determining region (CDR) 2 of SEQ ID NO: 42 or a VH CDR2 having at least 80%, 90%, 91%, 92%, 93%, 94%, 95%, 96%, 97%, 98%, 99% or more sequence identity with SEQ ID NO: 42; and/or (c) a variable heavy chain (VH) complementarity determining region (CDR) 3 consisting of a threonine (T) residue. In some embodiments, provided is a single chain variable fragment (scFv) comprising a variable heavy chain (VH) complementarity determining region (CDR) 1 of SEQ ID NO: 40 or a VH CDR1 having at least 80%, 90%, 91%, 92%, 93%, 94%, 95%, 96%, 97%, 98%, 99% or more sequence identity with SEQ ID NO: 40. In some embodiments, provided is a single chain variable fragment (scFv) comprising a variable heavy chain (VH) complementarity determining region (CDR) 2 of SEQ ID NO: 42 or a VH CDR2 having at least 80%, 90%, 91%, 92%, 93%, 94%, 95%, 96%, 97%, 98%, 99% or more sequence identity with SEQ ID NO: 42. In some embodiments, provided is a single chain variable fragment (scFv) comprising a variable heavy chain (VH) complementarity determining region (CDR) 3 consisting of a threonine (T) residue.

In some embodiments, provided is a single chain variable fragment (scFv) comprising (a) a variable light chain (VL) comprising (i) a complementarity determining region (CDR) 1 of SEQ ID NO: 46 or a CDR1 having at least 80%, 90%, 91%, 92%, 93%, 94%, 95%, 96%, 97%, 98%, 99% or more sequence identity with SEQ ID NO: 46; (ii) a CDR2 of SEQ ID NO: 48 or a CDR2 having at least 80%, 90%, 91%, 92%, 93%, 94%, 95%, 96%, 97%, 98%, 99% or more sequence identity with SEQ ID NO: 48; and/or (iii) a CDR3 of SEQ ID NO: 50 or a CDR3 having at least 80%, 90%, 91%, 92%, 93%, 94%, 95%, 96%, 97%, 98%, 99% or more sequence identity with SEQ ID NO: 50; and (b) a variable heavy chain (VH) of SEQ ID NO: 4 or a variable heavy chain (VH) having at least 80%, 90%, 91%, 92%, 93%, 94%, 95%, 96%, 97%, 98%, 99% or more sequence identity with SEQ ID NO: 4.

In some embodiments, provided is a single chain variable fragment (scFv) comprising (a) a variable light chain (VL) of SEQ ID NO: 6 or a variable light chain (VL) having at least 80%, 90%, 91%, 92%, 93%, 94%, 95%, 96%, 97%, 98%, 99% or more sequence identity with SEQ ID NO: 6; and (b) a variable heavy chain (VH) comprising (i) a complementarity determining region (CDR) 1 of SEQ ID NO: 40 or a CDR1 having at least 80%, 90%, 91%, 92%, 93%, 94%, 95%, 96%, 97%, 98%, 99% or more sequence identity with SEQ ID NO: 40; (ii) a CDR2 of SEQ ID NO: 42 or a CDR2 having at least 80%, 90%, 91%, 92%, 93%, 94%, 95%, 96%, 97%, 98%, 99% or more sequence identity with SEQ ID NO: 42; and/or (ii) a CDR3 consisting of a threonine (T) residue.

In some embodiments, provided is a single chain variable fragment (scFv) comprising (a) a variable light chain (VL) comprising (i) a complementarity determining region (CDR) 1 of SEQ ID NO: 46 or a CDR1 having at least 80%, 90%, 91%, 92%, 93%, 94%, 95%, 96%, 97%, 98%, 99% or more sequence identity with SEQ ID NO: 46; (ii) a CDR2 of SEQ ID NO: 48 or a CDR2 having at least 80%, 90%, 91%, 92%, 93%, 94%, 95%, 96%, 97%, 98%, 99% or more sequence identity with SEQ ID NO: 48; and/or (iii) a CDR3 of SEQ ID NO: 50 or a CDR3 having at least 80%, 90%, 91%, 92%, 93%, 94%, 95%, 96%, 97%, 98%, 99% or more sequence identity with SEQ ID NO: 50; and (b) a variable heavy chain (VH) comprising (i) a complementarity determining region (CDR) 1 of SEQ ID NO: 40 or a CDR1 having at least 80%, 90%, 91%, 92%, 93%, 94%, 95%, 96%, 97%, 98%, 99% or more sequence identity with SEQ ID NO: 40; (ii) a CDR2 of SEQ ID NO: 42 or a CDR2 having at least 80%, 90%, 91%, 92%, 93%, 94%, 95%, 96%, 97%, 98%, 99% or more sequence identity with SEQ ID NO: 42; and/or (ii) a CDR3 consisting of a threonine (T) residue.

In some embodiments, provided is a single chain variable fragment (scFv) comprising a variable heavy chain (VH) encoded by the nucleic acid of SEQ ID NO: 5 and/or a variable light chain (VL) encoded by the nucleic acid of SEQ ID NO:7. In some embodiments, provided is a single chain variable fragment (scFv) comprising a variable heavy chain (VH) encoded by the nucleic acid having at least 80%, 90%, 91%, 92%, 93%, 94%, 95%, 96%, 97%, 98%, 99% or more sequence identity with SEQ ID NO: 5. In some embodiments, provided is a single chain variable fragment (scFv) comprising a variable light chain (VL) encoded by the nucleic acid having at least 80%, 90%, 91%, 92%, 93%, 94%, 95%, 96%, 97%, 98%, 99% or more sequence identity with SEQ ID NO: 7.

In some embodiments, provided is a single chain variable fragment (scFv) comprising (a) a variable light chain (VL) complementarity determining region (CDR) 1 encoded by the nucleic acid of SEQ ID NO: 47 or a VL CDR1 encoded by the nucleic acid having at least 80%, 90%, 91%, 92%, 93%, 94%, 95%, 96%, 97%, 98%, 99% or more sequence identity with SEQ ID NO: 47; (b) a variable light chain (VL) complementarity determining region (CDR) 2 encoded by the nucleic acid of SEQ ID NO: 49 or a VL CDR2 encoded by the nucleic acid having at least 80%, 90%, 91%, 92%, 93%, 94%, 95%, 96%, 97%, 98%, 99% or more sequence identity with SEQ ID NO: 49; and/or (c) a variable light chain (VL) complementarity determining region (CDR) 3 encoded by the nucleic acid of SEQ ID NO: 51 or a VL CDR3 encoded by the nucleic acid having at least 80%, 90%, 91%, 92%, 93%, 94%, 95%, 96%, 97%, 98%, 99% or more sequence identity with SEQ ID NO: 51. In some embodiments, provided is a single chain variable fragment (scFv) comprising a variable light chain (VL) complementarity determining region (CDR) 1 encoded by the nucleic acid of SEQ ID NO: 47 or a VL CDR1 encoded by the nucleic acid having at least 80%, 90%, 91%, 92%, 93%, 94%, 95%, 96%, 97%, 98%, 99% or more sequence identity with SEQ ID NO: 47. In some embodiments, provided is a single chain variable fragment (scFv) comprising a variable light chain (VL) complementarity determining region (CDR) 2 encoded by the nucleic acid of SEQ ID NO: 49 or a VL CDR2 encoded by the nucleic acid having at least 80%, 90%, 91%, 92%, 93%, 94%, 95%, 96%, 97%, 98%, 99% or more sequence identity with SEQ ID NO: 49. In some embodiments, provided is a single chain variable fragment (scFv) comprising a variable light chain (VL) complementarity determining region (CDR) 3 encoded by the nucleic acid of SEQ ID NO: 51 or a VL CDR3 encoded by the nucleic acid having at least 80%, 90%, 91%, 92%, 93%, 94%, 95%, 96%, 97%, 98%, 99% or more sequence identity with SEQ ID NO: 51.

In some embodiments, provided is a single chain variable fragment (scFv) comprising (a) a variable heavy chain (VH) complementarity determining region (CDR) 1 encoded by the nucleic acid of SEQ ID NO: 41 or a VH CDR1 encoded by the nucleic acid having at least 80%, 90%, 91%, 92%, 93%, 94%, 95%, 96%, 97%, 98%, 99% or more sequence identity with SEQ ID NO: 41; (b) a variable heavy chain (VH) complementarity determining region (CDR) 2 encoded by the nucleic acid of SEQ ID NO: 43 or a VH CDR2 encoded by the nucleic acid having at least 80%, 90%, 91%, 92%, 93%, 94%, 95%, 96%, 97%, 98%, 99% or more sequence identity with SEQ ID NO: 43; and/or (c) a variable heavy chain (VH) complementarity determining region (CDR) 3 encoded by the nucleic acid consisting of SEQ ID NO: 45. In some embodiments, provided is a single chain variable fragment (scFv) comprising a variable heavy chain (VH) complementarity determining region (CDR) 1 encoded by the nucleic acid of SEQ ID NO: 41 or a VH CDR1 encoded by the nucleic acid having at least 80%, 90%, 91%, 92%, 93%, 94%, 95%, 96%, 97%, 98%, 99% or more sequence identity with SEQ ID NO: 41. In some embodiments, provided is a single chain variable fragment (scFv) comprising a variable heavy chain (VH) complementarity determining region (CDR) 2 encoded by the nucleic acid of SEQ ID NO: 43 or a VH CDR2 encoded by the nucleic acid having at least 80%, 90%, 91%, 92%, 93%, 94%, 95%, 96%, 97%, 98%, 99% or more sequence identity with SEQ ID NO: 43. In some embodiments, provided is a single chain variable fragment (scFv) comprising a variable heavy chain (VH) complementarity determining region (CDR) 3 encoded by the nucleic acid consisting of SEQ ID NO: 45.

In some embodiments, provided is a single chain variable fragment (scFv) comprising (a) a variable light chain (VL) comprising (i) a complementarity determining region (CDR) 1 encoded by the nucleic acid of SEQ ID NO: 47 or a CDR1 encoded by the nucleic acid having at least 80%, 90%, 91%, 92%, 93%, 94%, 95%, 96%, 97%, 98%, 99% or more sequence identity with SEQ ID NO: 47; (ii) a CDR2 encoded by the nucleic acid of SEQ ID NO: 49 or a CDR2 encoded by the nucleic acid having at least 80%, 90%, 91%, 92%, 93%, 94%, 95%, 96%, 97%, 98%, 99% or more sequence identity with SEQ ID NO: 49; and/or (iii) a CDR3 encoded by the nucleic acid of SEQ ID NO: 51 or a CDR3 encoded by the nucleic acid having at least 80%, 90%, 91%, 92%, 93%, 94%, 95%, 96%, 97%, 98%, 99% or more sequence identity with SEQ ID NO: 51; and (b) a variable heavy chain (VH) encoded by the nucleic acid of SEQ ID NO: 5 or a variable heavy chain (VH) encoded by the nucleic acid having at least 80%, 90%, 91%, 92%, 93%, 94%, 95%, 96%, 97%, 98%, 99% or more sequence identity with SEQ ID NO: 5.

In some embodiments, provided is a single chain variable fragment (scFv) comprising (a) a variable light chain (VL) encoded by the nucleic acid of SEQ ID NO: 7 or a variable light chain (VL) encoded by the nucleic acid having at least 80%, 90%, 91%, 92%, 93%, 94%, 95%, 96%, 97%, 98%, 99% or more sequence identity with SEQ ID NO: 7; and (b) a variable heavy chain (VH) comprising (i) a complementarity determining region (CDR) 1 encoded by the nucleic acid of SEQ ID NO: 41 or a CDR1 encoded by the nucleic acid having at least 80%, 90%, 91%, 92%, 93%, 94%, 95%, 96%, 97%, 98%, 99% or more sequence identity with SEQ ID NO: 41; (ii) a CDR2 encoded by the nucleic acid of SEQ ID NO: 43 or a CDR2 encoded by the nucleic acid having at least 80%, 90%, 91%, 92%, 93%, 94%, 95%, 96%, 97%, 98%, 99% or more sequence identity with SEQ ID NO: 43; and/or (ii) a CDR3 encoded by the nucleic acid consisting of SEQ ID NO: 45.

In some embodiments, provided is a single chain variable fragment (scFv) comprising (a) a variable light chain (VL) comprising (i) a complementarity determining region (CDR) 1 encoded by the nucleic acid of SEQ ID NO: 47 or a CDR1 encoded by the nucleic acid having at least 80%, 90%, 91%, 92%, 93%, 94%, 95%, 96%, 97%, 98%, 99% or more sequence identity with SEQ ID NO: 47; (ii) a CDR2 encoded by the nucleic acid of SEQ ID NO: 49 or a CDR2 encoded by the nucleic acid having at least 80%, 90%, 91%, 92%, 93%, 94%, 95%, 96%, 97%, 98%, 99% or more sequence identity with SEQ ID NO: 49; and/or (iii) a CDR3 encoded by the nucleic acid of SEQ ID NO: 51 or a CDR3 encoded by the nucleic acid having at least 80%, 90%, 91%, 92%, 93%, 94%, 95%, 96%, 97%, 98%, 99% or more sequence identity with SEQ ID NO: 51; and (b) a variable heavy chain (VH) comprising (i) a complementarity determining region (CDR) 1 encoded by the nucleic acid of SEQ ID NO: 41 or a CDR1 encoded by the nucleic acid having at least 80%, 90%, 91%, 92%, 93%, 94%, 95%, 96%, 97%, 98%, 99% or more sequence identity with SEQ ID NO: 41; (ii) a CDR2 encoded by the nucleic acid of SEQ ID NO: 43 or a CDR2 encoded by the nucleic acid having at least 80%, 90%, 91%, 92%, 93%, 94%, 95%, 96%, 97%, 98%, 99% or more sequence identity with SEQ ID NO: 43; and/or (ii) a CDR3 encoded by the nucleic acid consisting of SEQ ID NO: 45.

In some embodiments, the antigen-binding protein provided herein specifically binds to a CD20 protein or extracellular portion thereof in vitro and/or in vivo. In some embodiments, the antigen-binding protein provided herein specifically binds to a CD20 protein or extracellular portion thereof expressed on the surface of a cell. In some embodiments, the cell is a B cell. In some embodiments, the cell is a cancer cell. In some embodiments, the cell is a leukemia or a cancer cell.

TABLE 2

| | | Sequence | SEQ ID NO |
|---|---|---|---|
| α-K9CD20 VH | amino acid | EVQLVESGGGLVKPGTSLKLSCVASGFSFSDCWM SWARQTPGKTMEWIGDIKYDGRATNYAPSLQTRF IISRDNAKSTLYLQMTNVRSEDTATYYCTGNHYG GYTLRFAYWGQGTLVTVSS | 4 |

TABLE 2-continued

| | | Sequence | SEQ ID NO |
|---|---|---|---|
| | nucleic acid | gaagtacagcttgtggagtctggaggaggtttggtgaaacctgggacttctctg aaactctcttgtgtagcctcgggattcagtttcagtgactgctggatgagctggg ctcgccagactcctggaaagaccatggagtggattggagatattaaatatgatg gcagggccacaaactatgcaccttcccttcagactcgattcataatttccagag acaatgccaagagtaccctgtacctgcagatgaccaatgtgagatctgaggac acagccacttattattgtactgggaaccactacggaggctataccctccggtttg cttactggggccaaggcactctggtcactgtctcttca | 5 |
| α-K9CD20 VL | amino acid | DVVLTQTPPTLSATIGQSVSISCRSSQSLLHSNGNT FLQRPGQSPQLLIYLVSRLESGVPNRFSGSG SGTDFTLKISGVEAEDLGVYYCVQGTHAPPTFGG GGAGTNLELKRA | 6 |
| | nucleic acid | gatgttgtgctgacccagactccacccactttatcggctaccattggacaatcag tctccatctcttgcaggtcaagtcagagtctcttacatagtaatggaaacacctat ttacattggttcctacagaggccaggccaatctccacagcttctaatttacttggtt tccagactggaatctggggtccccaacaggttcagtggcagtgggtcaggaa ctgatttcacactcaaaatcagtggagtagaggctgaggatttgggagtttatta ctgtgttcaaggtacccatgctcctccgacgttcggtggcggcggagctggga ccaacctggagctgaaacgggct | 7 |
| α-K9CD20 scFv | amino acid | EVQLVESGGGLVKPGTSLKLSCVASGFSFSDCWM SWARQTPGKTMEWIGDIKYDGRATNYAPSLQTRF IISRDNAKSTLYLQMTNVRSEDTATYYCTGNHYG GYTLRFAYWGQGTLVTVSSGGGGSGGGGSGGGG SDVVLTQTPPTLSATIGQSVSISCRSSQSLLHSNGN TYLHWFLQRPGQSPQLLIYLVSRLESGVPNRF SGS GSGTDFTLKISGVEAEDLGVYYCVQGTHAPPTFG GGGAGTNLELKRA | 8 |
| | nucleic acid | gaagtacagcttgtggagtctggaggagggtttggtgaaacctgggacttctctg aaactctcttgtgtagcctcgggattcagtttcagtgactgctggatgagctggg ctcgccagactcctggaaagaccatggagtggattggagatattaaatatgatg gcagggccacaaactatgcaccttcccttcagactcgattcataatttccagag acaatgccaagagtaccctgtacctgcagatgaccaatgtgagatctgaggac acagccacttattattgtactgggaaccactacggaggctataccctccggttg cttactggggccaaggcactctggtcactgtctcttcaggtggaggtggatcag gtggaggtggatctggtggaggtggatctgatgttgtgctgacccagactcca cccactttatcggctaccattggacaatcagtctccatctcttgcaggtcaagtca gagtctcttacatagtaatggaaacacctatttacattggttcctacagaggcca ggccaatctccacagcttctaatttacttggtttccagactggaatctggggtccc caacaggttcagtggcagtgggtcaggaactgatttcacactcaaaatcagtg gagtagaggctgaggatttgggagtttattactgtgttcaaggtacccatgctcc tccgacgttcggtggcggcggagctgggaccaacctggagctgaaacgggc t | 9 |
| scFv Linker | amino acid | GGGGSGGGGSGGGGS | 10 |
| | nucleic acid | ggtggaggtggatcaggtggaggtggatctggtggaggtggatct | 11 |
| α-K9CD20 VH CDR1 | amino acid | GFSFSDCW | 40 |
| | nucleic acid | ggattcagtttcagtgactgctgg | 41 |
| α-K9CD20 VH CDR2 | amino acid | IKYDGRAT | 42 |
| | nucleic acid | attaaatatgatggcagggccaca | 43 |
| α-K9CD20 VH CDR3 | amino acid | TGNHYGGYTLRFAY | 44 |
| | nucleic acid | actgggaaccactacggaggctataccctccggtttgcttactg | 45 |
| α-K9CD20 VL CDR1 | amino acid | QSLLHSNGNTY | 46 |
| | nucleic acid | cagagtctcttacatagtaatggaaacacctat | 47 |
| α-K9CD20 VL CDR2 | amino acid | LVS | 48 |
| | nucleic acid | ttggtttcc | 49 |

TABLE 2-continued

| | | Sequence | SEQ ID NO |
|---|---|---|---|
| α-K9CD20 VL CDR3 | amino acid | VQGTHAPPTFGG | 50 |
| | nucleic acid | gttcaaggtacccatgctcctccgacgttcggtggc | 51 |
| Spacer sequence | | GSGGGK | 52 |
| PD1 extracellular sequence | amino acid | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQ | 53 |
| | nucleic acid | ccaggatggttatagactccccagacaggccctggaaccccccaccttctc cccagccctgctcgtggtgaccgaaggggacaacgccaccttcacctgcagc ttctccaacacatcggagagatcgtgctaaactggtaccgcatgagcccag caaccagacggacaagctggccgccttccccgaggaccgcagccagccg gccaggactgccgcttccgtgtcacacaactgcccaacgggcgtgacttcca catgagcgtggtcagggcccggcgcaatgacagcggcacctacctctgtgg ggccatctccctggcccccaaggcgcagatcaaagagagcctgcgggcaga gctcagggtgacagagagaagggcagaagtgcccacagcccaccccagcc cctcacccaggccagccggccag | 54 |
| PD-1 signal peptide and extracellular sequence | amino acid | MQIPQAPWPVVWAVLQLGWR PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQ | 55 |
| | nucleic acid | atgcagatcccacaggcgccctggccagtcgtctgggcggtgctacaactgg gctggcggccaggatggttcttagactccccagacaggccctggaaccccc caccttctccccagccctgctcgtggtgaccgaaggggacaacgccaccttca cctgcagatctccaacacatcggagagatcgtgctaaactggtaccgcatga gccccagcaaccagacggacaagctggccgccttccccgaggaccgcagc cagcccgccaggactgccgcttccgtgtcacacaactgcccaacgggcgt gacttccacatgagcgtggtcagggcccggcgcaatgacagcggcacctac ctctgtggggccatctccctggcccccaaggcgcagatcaaagagagcctgc gggcagagctcagggtgacagagagaagggcagaagtgcccacagccca ccccagcccctcacccaggccagccggccag | 56 |
| Signal peptide PD-1 | | MQIPQAPWPVVWAVLQLGWR | 57 |

The antigen-binding proteins, fragments and derivatives thereof, and fusion proteins of the present disclosure also include substantially homologous polypeptides that are 80%, 85%, 90%, 95%, 97%, 98%, or 99% identical to the peptides described in Table 1.

In some embodiments, the antigen-binding proteins, fragments and derivatives thereof, and fusion proteins of the present disclosure can specifically bind canine CD20 with a wide range of disassociation constants (Kd). For example, in some embodiments, antigen-binding proteins, fragments and derivatives thereof, and fusion proteins of the present disclosure can bind canine CD20 with a Kd equal to or less than about $10^{-7}$ M, such as, but not limited to, $0.1$-$9.9 \times 10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$ or any range or value therein, as determined by e.g., surface plasmon resonance or Kinexa method. The present disclosure encompasses antibodies that bind canine CD20 polypeptides with a disassociation constant or Kd that is within any one of the ranges that are between each of the individual recited values.

Antigen-binding proteins according to the present disclosure can be prepared by any of a number of conventional techniques. For example, they can be purified from cells that naturally express them (e.g., an antibody can be purified from a hybridoma that produces it), or produced in recombinant expression systems, using any technique known in the art. See, for example, Monoclonal Antibodies, Hybridoma: A New Dimension in Biological Analyses, Kennet et al. (eds.), Plenum Press, New York, 1980; Antibodies: A Laboratory Manual, Harlow and Land (eds.), Cold Spring Harbor Laboratory Press, Cold Spring Harbor, N.Y., 1988.

Any expression system known in the art can be used to make the recombinant polypeptides of the present disclosure. In general, host cells are transformed with a recombinant expression vector that comprises DNA encoding a desired polypeptide. Exemplary host cells that can be employed for protein expression include prokaryotes, yeast or higher eukaryotic cells. Prokaryotes include gram negative or gram positive organisms, for example E. coli or Bacillus bacteria. Higher eukaryotic cells include mammalian, insect, and plant cells and established cell lines thereof. Examples of suitable mammalian host cell lines include, but are not limited to the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) (McMahan et al., 1991, EMBO 110: 2821). Appropriate cloning and expression vectors for use with bacterial, fungal, yeast, and mammalian cellular hosts are described in the art, e.g., by Pouwels et al., Cloning Vectors: A Laboratory Manual, Elsevier, New York, 1985. The transformed cells can be cultured under conditions that promote expression of the polypeptide, and the polypeptide recovered by conventional protein purification procedures.

In some embodiments, the antigen-binding proteins according to the present disclosure are purified directly from serum of animals immunized with an antigen which the antigen-binding proteins, fragments and derivatives thereof, and fusion proteins of the present disclosure specifically recognizes. In some embodiments, the antigen-binding proteins according to the present disclosure are purified directly from hybridoma cell lines or animals bearing hybridoma cell tumors.

The amino acid sequence of the polypeptides disclosed herein can be verified by any means known in the art, and can be identical to the sequences disclosed herein in Table 2, or can differ from those sequences at one or more amino acid residues as result of processing. For example, on all or a portion of the substantially homogenous polypeptides, a C-terminal amino acid from either the light chain or the heavy chain (or relevant single-chain molecule) can be removed, by proteolytic processing or other processing that occurs during culture, for example, processing of C-terminal Lys residues. In some embodiments, more than one C-terminal amino acid residue can be removed, for example two C-terminal amino acids, or three, four or five C-terminal amino acids. Similarly, in some embodiments, N-terminal amino acids can be removed, for example, one, two, three, four or five N-terminal amino acids can be removed.

In some embodiments, the antigen-binding proteins, fragments and derivatives thereof, and fusion proteins of the present disclosure undergo post-translational modifications, for example but not limited to, a glutamine can be cyclized or converted to pyroglutamic acid; additionally, or alternatively, amino acids can undergo deamidation, isomerization, glycation and/or oxidation. The polypeptides of the present disclosure can undergo additional post-translational modification, including glycosylation, for example N-linked or O-linked glycosylation, at sites that are well-known in the art. As described previously, changes can be made in the amino acid sequence of a polypeptide to preclude or minimize such alterations, or to facilitate them in circumstances where such processing is beneficial.

Antigen-binding polypeptides according to the present disclosure can be prepared, and screened for desired properties, by any of a number of known techniques. Certain of the techniques involve isolating a nucleic acid encoding a polypeptide chain (or portion thereof) of an antigen-binding protein of interest, and manipulating the nucleic acid through recombinant DNA technology. In some embodiments, the nucleic acid is fused to another nucleic acid of interest, or altered (e.g., by mutagenesis or other conventional techniques) to add, delete, or substitute one or more amino acid residues, for example.

Polypeptides of the present disclosure include polypeptides that have been modified, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Additionally, single or multiple amino acid substitutions (e.g., conservative amino acid substitutions) made in a sequence described in Table 1 (e.g., in the portion of the polypeptide outside the domain(s) forming intermolecular contacts) are encompassed by the present disclosure. Consensus sequences can be used to select amino acid residues for substitution; those of skill in the art recognize that additional amino acid residues can also be substituted.

Antigen-binding proteins (e.g., antibodies, antibody fragments, antibody derivatives, chimeric antigen receptors, and fusion proteins) of the present disclosure can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one aspect, the light or heavy chain constant region is a fragment, derivative, variant, or mutant of a naturally occurring constant region.

In one aspect, the antigen-binding protein of the present disclosure comprises a fragment of an antibody. Such fragments can consist entirely of antibody-derived sequences or can comprise additional sequences. Fragments can be, for example, at least 5, 6, 7, 8, 9, 10, 11, 12, 13, 14, 15, 20, 50, 60, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. Fragments can also result from proteolytic (or other) processing, which, for example, results in variation in the amino and/or carboxyl terminus of from one to five amino acids from that predicted. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence or a tag protein). Amino and carboxyl-termini of fragments or analogs can occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, *Science* 253:164.

Examples of antigen-binding fragments include Fab, F(ab')2, single chain antibodies such as scFvs, diabodies, triabodies, tetrabodies, and domain antibodies. Other examples of antigen-binding fragments are known in the art, e.g., as provided in Lunde et al., 2002, *Biochem. Soc. Trans.* 30:500-06.

In another aspect, the antigen-binding protein of the present disclosure comprises a derivative of an antibody. The derivative can comprise any molecule or substance that imparts a desired property, such as increased half-life in a particular use. Examples of molecules that can be used to form a derivative include, but are not limited to, albumin (e.g., human serum albumin) and polyethylene glycol (PEG). Albumin-linked and PEGylated derivatives of antibodies can be prepared using techniques well known in the art.

In one embodiment, the present disclosure provides an isolated antigen-binding protein or fragment or derivative thereof, comprising one or more amino acid sequences selected from the group consisting of SEQ ID NOs: 4, 6 or 8. In one embodiment, the present disclosure provides an isolated antigen-binding protein or fragment or derivative thereof, comprising one or more amino acid sequences selected from the group encoded by SEQ ID NOs: 5, 7 or 9.

In one aspect, an isolated antigen-binding protein of the present disclosure is an antibody. In one aspect, the antibody is a full-length antibody, a substantially intact antibody, or an antibody fragment, e.g., a Fab fragment, a F(ab')2 fragment, or a single chain variable fragment (scFv). In some embodiments, a scFv is formed by linking heavy and light chain variable domain (Fv region) fragments via an amino acid bridge (short peptide linker), resulting in a single polypeptide chain. Such single chain Fvs (scFvs) have been prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different VL and VH-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

In one embodiment, the present disclosure provides an isolated scFv comprising a VH and a VL, wherein the VH and VL, respectively, comprise amino acid sequences represented by SEQ ID NOs: 4 and 6. In one embodiment, the present disclosure provides an isolated scFv comprising a VH and a VL, wherein the VH and VL, respectively, comprise amino acid sequences encoded by the nucleic acid set forth in SEQ ID NOs: 5 and 7.

In one embodiment, the present disclosure provides an isolated scFv comprising a VH and a VL linked by an amino acid linker. In one embodiment, the amino acid linker comprises serine and glycine residues. In one embodiment, the linker comprises the amino acid sequence set forth in SEQ ID NO: 10. In one embodiment, the linker comprises the amino acid sequence encoded by the nucleic acid sequence set forth in SEQ ID NO: 11.

In one embodiment, the present disclosure provides an isolated scFv comprising a VH and a VL linked by an amino acid linker, wherein the VH, VL and linker, respectively, comprise amino acid sequences represented by SEQ ID NOs: 4, 6, and 10. In one embodiment, the present disclosure provides an isolated scFv comprising a VH and a VL linked by an amino acid linker, wherein the VH, VL and linker, respectively, comprise amino acid sequences encoded by the nucleic acid sequences set forth in SEQ ID NOs: 5, 7, and 11.

In one embodiment, the present disclosure provides an isolated scFv comprising an amino acid sequence represented by SEQ ID NO: 8. In one embodiment, the isolated scFv comprises an amino acid sequence encoded by the nucleic acid sequence set forth in SEQ ID NO: 9.

In one aspect, the present disclosure provides a fusion protein comprising an isolated antigen-binding protein or scFv described herein. In one aspect, the fusion protein is a scFv-Fc fusion protein, an immunoconjugate, or a bispecific antibody. In one aspect, the fusion protein is a scFv-Fc fusion protein comprising a Fc from human IgG1. The fusion protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses) such as a nanoparticle or liposome. In one aspect, the fusion protein comprises a component selected from the group consisting of a cytotoxin, a detectable label, a radioisotope, a therapeutic agent, a nanoparticle, a liposome, a binding protein, an oligonucleotide, an enzyme, or an antibody.

Generation of Chimeric Antigen Receptors (CAR)

In some embodiments of the present disclosure, the antigen-binding protein or scFv is provided in the form of a T cell receptor (TCR) or chimeric antigen receptor (CAR). CARs are engineered receptors, which graft or confer a specificity of interest onto an immune effector cell. For example, CARs can be used to graft the specificity of a monoclonal antibody onto an immune cell, such as a T cell. In some embodiments, transfer of the coding sequence of the CAR is facilitated by nucleic acid vector, such as a retroviral vector.

There are currently three generations of CARs. In some embodiments, the antigen-binding protein or scFv is provided in the form of a "first generation" CAR. "First generation" CARs are typically composed of an extracellular antigen binding domain (e.g., a single-chain variable fragment (scFv)) fused to a transmembrane domain fused to cytoplasmic/intracellular domain of the T cell receptor (TCR) chain. In some embodiments, the extracellular antigen binding domain of the "First generation" CAR comprises an antigen-binding protein disclosed herein. In some embodiments, the extracellular antigen binding domain of the "First generation" CAR comprises a scFv disclosed herein. "First generation" CARs typically encode the intracellular domain from the CD3 chain, which is the primary transmitter of signals from endogenous TCRs. "First generation" CARs can provide de novo antigen recognition and cause activation of both CD4$^+$ and CD8$^+$ T cells through their CD3ζ chain signaling domain in a single fusion molecule, independent of HLA-mediated antigen presentation.

In some embodiments, the antigen-binding protein or scFv is provided in the form of a "second generation" CAR. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-IBB) and activation (e.g., CD3ζ). In some embodiments, the extracellular antigen binding domain of the "Second generation" CAR comprises an antigen-binding protein disclosed herein. In some embodiments, the extracellular antigen binding domain of the "Second generation" CAR comprises a scFv disclosed herein.

In some embodiments, the antigen-binding protein or scFv is provided in the form of a "third generation" CAR. "Third generation" CARs comprise those that provide multiple co-stimulation (e.g., CD28 and 4-1BB) and activation (e.g., CD3ζ). In some embodiments, the extracellular antigen binding domain of the "Third generation" CAR comprises an antigen-binding protein disclosed herein. In some embodiments, the extracellular antigen binding domain of the "Third generation" CAR comprises a scFv disclosed herein.

In accordance with the presently disclosed subject matter, the CARs of the engineered immune cells provided herein comprise an extracellular antigen-binding domain, a transmembrane domain and an intracellular domain.

In various embodiments, the antigen-binding protein can be either exogenous or endogenous. In some embodiments, the antigen-binding protein can be recombinantly produced by fusing portions of immunostimulatory proteins together. In some embodiments, the antigen-binding protein comprises a scFv disclosed herein fused to at least a portion of one or more immunostimulatory proteins. In various embodiments, the different immunostimulatory proteins can be from the same or different animal species, such as human, mouse or canine.

In some embodiments, the CARs disclosed herein are "Third generation" CARs. In some embodiments, the CARs further provide costimulation via one or more costimulatory molecules (also called costimulatory ligands). In some embodiments, the chimeric antigen receptor comprises one or more costimulatory ligands. In some embodiments, the CAR comprises 1, 2, 3, 4, 5, 6, 7, 8, 9, or 10 or more costimulatory ligands. Without intending to be bound by theory, it is contemplated that the interaction with at least one co-stimulatory ligand provides a non-antigen-specific signal important for full activation of an immune cell (e.g., T cell). Co-stimulatory ligands include, without limitation, tumor necrosis factor (TNF) ligands, cytokines (such as IL-2, IL-12, IL-15 or IL21), and immunoglobulin (Ig) superfamily ligands. Tumor necrosis factor (TNF) is a cytokine involved in systemic inflammation and stimulates the acute phase reaction. Its primary role is in the regulation of immune cells. Tumor necrosis factor (TNF) ligands share a number of common features. The majority of the ligands are synthesized as type II transmembrane proteins (extracellular C-terminus) containing a short cytoplasmic segment and a relatively long extracellular region. TNF ligands include, without limitation, nerve growth factor (NGF), CD40L (CD40L)/CD154, CD137L/4-1BBL, tumor necrosis factor alpha (TNFα), CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LT (3), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, without limitation, CD80 and CD86, both ligands for CD28. In some embodiments, the costimulatory molecule is 4-1BBL.

In some embodiments, the intracellular signaling domain of the antigen recognizing receptor is the CD4-chain, CD97, CD11a-CD18, CD2, ICOS, CD27, CD154, CDS, OX40, 4-IBB, CD28 signaling domain, a portion thereof, or combinations thereof. In some embodiments, the antigen recognizing receptor is a CAR comprising at least a portion of CD28, 4-1BB, and/or CD3ζ-chain (see, e.g., Zhong et al., 2010, *Molecular Ther.* 18(2):413-420), together with an antigen binding portion. In some embodiments, the antigen-binding protein is a CAR described in Kohn et al., 2011, *Molecular Ther.* 19(3):432-438), optionally where the antigen binding portion is substituted with amino acid sequence that binds to another tumor or pathogen antigen. In some embodiments, the antigen binding portion of the chimeric antigen receptor is selected from immunoglobulins, variable regions of immunoglobulins (e.g., variable fragments "Fv"), bivalent variable fragments (Fab), and single chain variable fragments (scFv), etc.

In some embodiments, the chimeric antigen receptor comprises at least a portion of CD28, 4-1BB, and/or CD3ζ-chain, together with a scFv that specifically binds to canine CD20 extracellular domain. In some embodiments, the anti-CD20 scFv comprises the amino acid sequence set forth in SEQ ID NO: 8. In some embodiments, the CD28 costimulatory domain comprises the amino acid sequence set forth in SEQ ID NO: 14. In some embodiments, the CD3ζ chain comprises the amino acid sequence set forth in SEQ ID NO: 16. In some embodiments, the 4-1BBL costimulatory domain comprises the amino acid sequence set forth in SEQ ID NO: 18. Exemplary amino acid and encoding nucleotide sequences for a canine CD8 leader, a canine CD28 costimulatory domain, a canine CD3-chain and a canine 4-1BBL costimulatory domain are provided in Table 3. In some embodiments, the chimeric antigen receptor is a recombinantly produced fusion protein comprising one or more segments of amino acid sequences selected from the group consisting of SEQ ID NO: 4, 6, 8, 10, 12, 14, 16, 18, 22, 40, 42, 46, 48, and 50.

TABLE 3

| | | Sequence | SEQ ID NO |
|---|---|---|---|
| K9CD8 leader | amino acid | MASRVTALLLPLALLLRAAAA | 12 |
| | nucleic acid | atggcctctcgggtgaccgccctgctcctgccgctggccctgctgctccgtgcc gcggcggcc | 13 |
| K9CD28 | amino acid | IEVMYPPPYIGNEKSNGTIIHVKEKHLCPDELFPDSS KPFWALVVVGAVLVFYSLLVTVALCAYWIKSKSS RILQSDYMNMTPRRPGPTRRHYQPYAPARDFAAY RS | 14 |
| | nucleic acid | attgaggtcatgtatccacctccttacattggcaatgagaagagcaatgggacca ttatccatgtgaaagaaaaacatctttgtccagatgagctgtttcctgattcttctaa gccatttttgggcactggtggtggttggtgcagtcctagttttctatagcttgctagt aacagtggctctttgtgcctactggataaagagtaagagtagcaggatccttcag agtgactacatgaacatgaccccccggaggccggggcccacccgaaggcac taccaaccctatgccccagcacgcgactttgcagcataccgctcc | 15 |
| K9CD3ζ | amino acid | RLRSTRPAAPPGAPRGPGQSPRRSSRLLQELNLRG REEYEVLDKRRGLDPEMGGKQRKRNPQEVVYNA LQKDKMAEAYSEIGIKSENQRRRGKGHDGLYQGL STATKDTYDALHMQALPPR | 16 |

TABLE 3-continued

| | | Sequence | SEQ ID NO |
|---|---|---|---|
| | nucleic acid | cggctccgctccaccaggcccgcggctccccgggcgccccacggggtcca ggccagagcccccgacggtcttcccgcctcctgcaggagctcaatctgcgag gaagagaggagtacgaggttttggataagagacgcggcctggacccggagat gggaggaaagcagaggaagaggaaccctcaggaggtcgtgtacaatgcact gcagaaagacaagatggcagaggcctacagtgagattgggataaaaagcga gaaccagcgtcggagagggaaggggcatgatggccttaccaggggctcag cacggccaccaaggacacctatgatgccctccacatgcaggccctgcctcctc gc | 17 |
| K9 4-1BBL | amino acid | MRPRSDAAPDPEAPRPPAPPGRACSPLPWALSAA MLLLVGTCAACALRAWVVPGPRPPALPALPAPLP DAGARLPDSPQAVFAQLVARDVQLKEGPLRWYS DPGLAGVFLGPGLSYDQHTRELMVVEPGLYYVFL HLKLQRVMSSTGSGSVSAALHLQPLGTEAAALDL TLDLPPPSSEARDSAAGFRGSLLHLDAGQRLRVHL RAEGAHPAWQLAQGATILGLFRVATKVPTGLPS SWPMDTGPGSPPLDGE | 18 |
| | nucleic acid | atgcgccccgcagcgacgccgccccggaccccgaggccccgcggccgcc cgcgcccccggccgcgcctgcagcccgctgccctgggcgctgagcgccgc gatgctgctgctcgtcggcacctgcgccgcctgcgcgctccgcgcctgggtgg tccccgggcccggccccccgcgctccccgcgctcccccgcgcccctgccgg acgccggcgcccgcctccccgactcccccgcaggccgtgttcgcgcagctggt ggcccgagatgtacagctgaaggaaggacccctgcgctggtacagtgacccg ggcctggcaggtgtattcctggggccgggcctgagttatgaccagcacactcg ggagctgatggtggtggaacccgggctctactatgttttcttgcacctgaagctg cagcgggtaatgtccagcacgggctccggctctgtctctgctgccctgcacctg cagccacttggcaccgaggctgcagccctggacctgaccttgacctgcctcc accatcctcggaggcccgtgactcagcagctggtttccggggcagcctgctgc acctggacgcaggccagcgcctccgtgttcacttgcgagctgaggcagggc ccaccctgcctggcagctggcacaaggtgccacgatcttgggcctcttcagagt ggccaccaaagtccccactggactcccctcgtcatggcccatggacacgggg cctgggtccccgccctggatggagaa | 19 |
| K9 CD34t | amino acid | MLAGRGARAGGGLPRGWTALCLLSLLPFGFTNTE TVITPTTVPTSTEIMSAVSENTSKREAITLTPSGTTT LYSVSQDSSGTTATISETTVHVTSTSEITLTPGTMN SSVQSQTSLAITVSFTPTNFSTSSVTLEPSLLPGNGS DPPYNSTSLVTSPTEYYTSLSPTPSRNDTPSTIKGEI KCSGVKEVKLNQGICLELNETSSCEDFKKDNEEKL TQVLCEKEPAEAGAGVCSLLLAQSEVRPHCLLLVL ANKTELFSKLQLLRKHQSDLKKLGIRDFTEQDVGS HQSYSRKTLIALVTSGILLAVLGTTGYFLMNRRSW SPTGE | 22 |
| | nucleic acid | Atgctggcgggcaggggcgcgcgcgggcggcgggctgccgcgggct ggaccgcgctctgcctgctcagtctgctgccctttgggttcacaaacacagaaa ccgtgattactcctaccacagtgccaacctccacagaaataatgtcagctgtttct gagaatacatccaaacgggaagccatcacactaactccttctggaactaccacc ctgtactctgtctctcaagacagcagtgggaccacagcaaccatctcagagact acagtccatgtcacatctacctctgagatcaccctaacgcctgggaccatgaact cttctgttcagtcgcagacctctttagctatcacggtatcttttaccccaaccaactt ttcaacttcaagtgtgaccttggagcccagctgctacctggaaatggttcggat ccccctacaacagcaccagccttgtgacatcccccacggaatattatacatca ctttctcctaccccaagtagaaatgacaccccaagtaccatcaagggagaaatc aaatgttccggagtcaaagaagtgaaattgaaccaaggtatctgcctagagcta aatgagacctccagctgtgaggactttaagaaagataacgaagaaaaactgac ccaagtcctgtgtgagaaggagccagctgaggctggggccggggtgtgctcc ctgcttctggcccagtctgaggtgaggcctcactgcctgctgctggtcttggcca acaaaacagaactttttcagtaaactccaacttctgagaaagcaccagtctgacct gaaaaagctggggatccgagacttcactgaacaagatgtgggagccaccag agctattcccgcaagacccctgattgcactggtcacctcagggatcctgctggct gtcttgggcaccactggttacttcctgatgaaccgccgcagttggagccctaca ggagaa | 23 |

In some embodiments, provided is a chimeric antigen receptor (CAR) comprising an extracellular antigen binding domain comprising a single chain variable fragment (scFv), wherein the scFv comprises (a) a variable light chain (VL) complementarity determining region (CDR) 1 of SEQ ID NO: 46 or a VL CDR1 having at least 80%, 90%, 91%, 92%, 93%, 94%, 95%, 96%, 97%, 98%, 99% or more sequence identity with SEQ ID NO: 46; (b) a VL CDR2 of SEQ ID NO: 48 or a VL CDR2 having at least 80%, 90%, 91%, 92%, 93%, 94%, 95%, 96%, 97%, 98%, 99% or more sequence identity with SEQ ID NO: 48; and/or (c) a VL CDR3 of SEQ ID NO: 50 or a VL CDR3 having at least 80%, 90%, 91%, 92%, 93%, 94%, 95%, 96%, 97%, 98%, 99% or more sequence identity with SEQ ID NO: 50. In some embodiments, provided is a CAR comprising an extracellular antigen binding domain comprising a scFv, wherein the scFv comprises a VL CDR1 of SEQ ID NO: 46 or a VL CDR1 having at least 80%, 90%, 91%, 92%, 93%, 94%, 95%, 96%, 97%, 98%, 99% or more sequence identity with SEQ ID NO: 46. In some embodiments, provided is a CAR comprising an extracellular antigen binding domain comprising a scFv, wherein the scFv comprises a VL CDR2 of SEQ ID NO: 48 or a VL CDR2 having at least 80%, 90%, 91%, 92%, 93%, 94%, 95%, 96%, 97%, 98%, 99% or more sequence identity with SEQ ID NO: 48. In some embodiments, provided is a CAR comprising an extracellular antigen binding domain comprising a scFv, wherein the scFv comprises a VL CDR3 of SEQ ID NO: 50 or a VL CDR3 having at least 80%, 90%, 91%, 92%, 93%, 94%, 95%, 96%, 97%, 98%, 99% or more sequence identity with SEQ ID NO: 50.

In some embodiments, provided is a CAR comprising an extracellular antigen binding domain comprising a scFv, wherein the scFv comprises (a) a variable heavy chain (VH) complementarity determining region (CDR) 1 of SEQ ID NO: 40 or a VH CDR1 having at least 80%, 90%, 91%, 92%, 93%, 94%, 95%, 96%, 97%, 98%, 99% or more sequence identity with SEQ ID NO: 40; (b) a VH CDR2 of SEQ ID NO: 42 or a VH CDR2 having at least 80%, 90%, 91%, 92%, 93%, 94%, 95%, 96%, 97%, 98%, 99% or more sequence identity with SEQ ID NO: 42; and/or (c) a VH CDR3 consisting of a threonine (T) residue. In some embodiments, provided is a CAR comprising an extracellular antigen binding domain comprising a scFv, wherein the scFv comprises a VH CDR1 of SEQ ID NO: 40 or a VH CDR1 having at least 80%, 90%, 91%, 92%, 93%, 94%, 95%, 96%, 97%, 98%, 99% or more sequence identity with SEQ ID NO: 40. In some embodiments, provided is a CAR comprising an extracellular antigen binding domain comprising a scFv, wherein the scFv comprises a VH CDR2 of SEQ ID NO: 42 or a VH CDR2 having at least 80%, 90%, 91%, 92%, 93%, 94%, 95%, 96%, 97%, 98%, 99% or more sequence identity with SEQ ID NO: 42. In some embodiments, provided is a CAR comprising an extracellular antigen binding domain comprising a scFv, wherein the scFv comprises a VH CDR3 consisting of a threonine (T) residue.

In some embodiments, provided is a CAR comprising an extracellular antigen binding domain comprising a scFv, wherein the scFv comprises (a) a variable light chain (VL) comprising (i) a complementarity determining region (CDR) 1 of SEQ ID NO: 46 or a CDR1 having at least 80%, 90%, 91%, 92%, 93%, 94%, 95%, 96%, 97%, 98%, 99% or more sequence identity with SEQ ID NO: 46; (ii) a CDR2 of SEQ ID NO: 48 or a CDR2 having at least 80%, 90%, 91%, 92%, 93%, 94%, 95%, 96%, 97%, 98%, 99% or more sequence identity with SEQ ID NO: 48; and/or (iii) a CDR3 of SEQ ID NO: 50 or a CDR3 having at least 80%, 90%, 91%, 92%, 93%, 94%, 95%, 96%, 97%, 98%, 99% or more sequence identity with SEQ ID NO: 50; and (b) a variable heavy chain (VH) of SEQ ID NO: 4 or a variable heavy chain (VH) having at least 80%, 90%, 91%, 92%, 93%, 94%, 95%, 96%, 97%, 98%, 99% or more sequence identity with SEQ ID NO: 4.

In some embodiments, provided is a CAR comprising an extracellular antigen binding domain comprising a scFv, wherein the scFv comprises (a) a VL of SEQ ID NO: 6 or a VL having at least 80%, 90%, 91%, 92%, 93%, 94%, 95%, 96%, 97%, 98%, 99% or more sequence identity with SEQ ID NO: 6; and (b) a VH comprising (i) a CDR1 of SEQ ID NO: 40 or a CDR1 having at least 80%, 90%, 91%, 92%, 93%, 94%, 95%, 96%, 97%, 98%, 99% or more sequence identity with SEQ ID NO: 40; (ii) a CDR2 of SEQ ID NO: 42 or a CDR2 having at least 80%, 90%, 91%, 92%, 93%, 94%, 95%, 96%, 97%, 98%, 99% or more sequence identity with SEQ ID NO: 42; and/or (ii) a CDR3 consisting of a threonine (T) residue.

In some embodiments, provided is a CAR comprising an extracellular antigen binding domain comprising a scFv, wherein the scFv comprises (a) a VL comprising (i) a CDR1 of SEQ ID NO: 46 or a CDR1 having at least 80%, 90%, 91%, 92%, 93%, 94%, 95%, 96%, 97%, 98%, 99% or more sequence identity with SEQ ID NO: 46; (ii) a CDR2 of SEQ ID NO: 48 or a CDR2 having at least 80%, 90%, 91%, 92%, 93%, 94%, 95%, 96%, 97%, 98%, 99% or more identity with SEQ ID NO: 48; and/or (iii) a CDR3 of SEQ ID NO: 50 or a CDR3 having at least 80%, 90%, 91%, 92%, 93%, 94%, 95%, 96%, 97%, 98%, 99% or more sequence identity with SEQ ID NO: 50; and (b) a VH comprising (i) a CDR1 of SEQ ID NO: 40 or a CDR1 having at least 80%, 90%, 91%, 92%, 93%, 94%, 95%, 96%, 97%, 98%, 99% or more sequence identity with SEQ ID NO: 40; (ii) a CDR2 of SEQ ID NO: 42 or a CDR2 having at least 80%, 90%, 91%, 92%, 93%, 94%, 95%, 96%, 97%, 98%, 99% or more sequence identity with SEQ ID NO: 42; and/or (ii) a CDR3 consisting of a threonine (T) residue.

In some embodiments, provided is a CAR comprising an extracellular antigen binding domain comprising a scFv, wherein the scFv comprises a variable heavy chain (VH) encoded by the nucleic acid of SEQ ID NO: 5 and/or a variable light chain (VL) encoded by the nucleic acid of SEQ ID NO:7. In some embodiments, provided is a CAR comprising an extracellular antigen binding domain comprising a scFv, wherein the scFv comprises a VH encoded by the nucleic acid having at least 80%, 90%, 91%, 92%, 93%, 94%, 95%, 96%, 97%, 98%, 99% or more sequence identity with SEQ ID NO: 5. In some embodiments, provided is a CAR comprising an extracellular antigen binding domain comprising a scFv, wherein the scFv comprises a VL encoded by the nucleic acid having at least 80%, 90%, 91%, 92%, 93%, 94%, 95%, 96%, 97%, 98%, 99% or more sequence identity with SEQ ID NO: 7.

In some embodiments, provided is a CAR comprising an extracellular antigen binding domain comprising a scFv, wherein the scFv comprises (a) a VL CDR1 encoded by the nucleic acid of SEQ ID NO: 47 or a VL CDR1 encoded by the nucleic acid having at least 80%, 90%, 91%, 92%, 93%, 94%, 95%, 96%, 97%, 98%, 99% or more sequence identity with SEQ ID NO: 47; (b) a VL CDR2 encoded by the nucleic acid of SEQ ID NO: 49 or a VL CDR2 encoded by the nucleic acid having at least 80%, 90%, 91%, 92%, 93%, 94%, 95%, 96%, 97%, 98%, 99% or more sequence identity with SEQ ID NO: 49; and/or (c) a VL CDR3 encoded by the nucleic acid of SEQ ID NO: 51 or a VL CDR3 encoded by the nucleic acid having at least 80%, 90%, 91%, 92%, 93%, 94%, 95%, 96%, 97%, 98%, 99% or more sequence identity with SEQ ID NO: 51. In some embodiments, provided is a CAR comprising an extracellular antigen binding domain comprising a scFv, wherein the scFv comprises a VL CDR1 encoded by the nucleic acid of SEQ ID NO: 47 or a VL CDR1 encoded by the nucleic acid having at least 80%, 90%, 91%, 92%, 93%, 94%, 95%, 96%, 97%, 98%, 99% or more sequence identity with SEQ ID NO: 47. In some embodiments, provided is a CAR comprising an extracellular antigen binding domain comprising a scFv, wherein the scFv comprises a VL CDR2 encoded by the nucleic acid of SEQ ID NO: 49 or a VL CDR2 encoded by the nucleic acid having at least 80%, 90%, 91%, 92%, 93%, 94%, 95%, 96%, 97%, 98%, 99% or more sequence identity with SEQ ID NO: 49. In some embodiments, provided is a CAR comprising an extracellular antigen binding domain comprising a scFv, wherein the scFv comprises a VL CDR3 encoded by the nucleic acid of SEQ ID NO: 51 or a VL CDR3 encoded by the nucleic acid having at least 80%, 90%, 91%, 92%, 93%, 94%, 95%, 96%, 97%, 98%, 99% or more sequence identity with SEQ ID NO: 51.

In some embodiments, provided is a CAR comprising an extracellular antigen binding domain comprising a scFv, wherein the scFv comprises (a) a VH CDR1 encoded by the nucleic acid of SEQ ID NO: 41 or a VH CDR1 encoded by the nucleic acid having at least 80%, 90%, 91%, 92%, 93%, 94%, 95%, 96%, 97%, 98%, 99% or more sequence identity with SEQ ID NO: 41; (b) a VH CDR2 encoded by the nucleic acid of SEQ ID NO: 43 or a VH CDR2 encoded by the nucleic acid having at least 80%, 90%, 91%, 92%, 93%, 94%, 95%, 96%, 97%, 98%, 99% or more sequence identity with SEQ ID NO: 43; and/or (c) a VH CDR3 encoded by the nucleic acid consisting of SEQ ID NO: 45. In some embodiments, provided is a CAR comprising an extracellular antigen binding domain comprising a scFv, wherein the scFv comprises a VH CDR1 encoded by the nucleic acid of SEQ ID NO: 41 or a VH CDR1 encoded by the nucleic acid having at least 80%, 90%, 91%, 92%, 93%, 94%, 95%, 96%, 97%, 98%, 99% or more sequence identity with SEQ ID NO: 41. In some embodiments, provided is a CAR comprising an extracellular antigen binding domain comprising a scFv, wherein the scFv comprises a VH CDR2 encoded by the nucleic acid of SEQ ID NO: 43 or a VH CDR2 encoded by the nucleic acid having at least 80%, 90%, 91%, 92%, 93%, 94%, 95%, 96%, 97%, 98%, 99% or more sequence identity with SEQ ID NO: 43. In some embodiments, provided is a CAR comprising an extracellular antigen binding domain comprising a scFv, wherein the scFv comprises a VH CDR3 encoded by the nucleic acid consisting of SEQ ID NO: 45.

In some embodiments, provided is a CAR comprising an extracellular antigen binding domain comprising a scFv, wherein the scFv comprises (a) a VL comprising (i) a CDR1 encoded by the nucleic acid of SEQ ID NO: 47 or a CDR1 encoded by the nucleic acid having at least 80%, 90%, 91%, 92%, 93%, 94%, 95%, 96%, 97%, 98%, 99% or more sequence identity with SEQ ID NO: 47; (ii) a CDR2 encoded by the nucleic acid of SEQ ID NO: 49 or a CDR2 encoded by the nucleic acid having at least 80%, 90%, 91%, 92%, 93%, 94%, 95%, 96%, 97%, 98%, 99% or more sequence identity with SEQ ID NO: 49; and/or (iii) a CDR3 encoded by the nucleic acid of SEQ ID NO: 51 or a CDR3 encoded by the nucleic acid having at least 80%, 90%, 91%, 92%, 93%, 94%, 95%, 96%, 97%, 98%, 99% or more sequence identity with SEQ ID NO: 51; and (b) a VH encoded by the nucleic acid of SEQ ID NO: 5 or a VH encoded by the nucleic acid having at least 80%, 90%, 91%, 92%, 93%, 94%, 95%, 96%, 97%, 98%, 99% or more sequence identity with SEQ ID NO: 5.

In some embodiments, provided is a CAR comprising an extracellular antigen binding domain comprising a scFv, wherein the scFv comprises (a) a VL encoded by the nucleic acid of SEQ ID NO: 7 or a VL encoded by the nucleic acid having at least 80%, 90%, 91%, 92%, 93%, 94%, 95%, 96%, 97%, 98%, 99% or more sequence identity with SEQ ID NO: 7; and (b) a VH comprising (i) a CDR1 encoded by the nucleic acid of SEQ ID NO: 41 or a CDR1 encoded by the nucleic acid having at least 80%, 90%, 91%, 92%, 93%, 94%, 95%, 96%, 97%, 98%, 99% or more sequence identity with SEQ ID NO: 41; (ii) a CDR2 encoded by the nucleic acid of SEQ ID NO: 43 or a CDR2 encoded by the nucleic acid having at least 80%, 90%, 91%, 92%, 93%, 94%, 95%, 96%, 97%, 98%, 99% or more sequence identity with SEQ ID NO: 43; and/or (ii) a CDR3 encoded by the nucleic acid consisting of SEQ ID NO: 45.

In some embodiments, provided is a CAR comprising an extracellular antigen binding domain comprising a scFv, wherein the scFv comprises (a) a VL comprising (i) a CDR1 encoded by the nucleic acid of SEQ ID NO: 47 or a CDR1 encoded by the nucleic acid having at least 80%, 90%, 91%, 92%, 93%, 94%, 95%, 96%, 97%, 98%, 99% or more sequence identity with SEQ ID NO: 47; (ii) a CDR2 encoded by the nucleic acid of SEQ ID NO: 49 or a CDR2 encoded by the nucleic acid having at least 80%, 90%, 91%, 92%, 93%, 94%, 95%, 96%, 97%, 98%, 99% or more sequence identity with SEQ ID NO: 49; and/or (iii) a CDR3 encoded by the nucleic acid of SEQ ID NO: 51 or a CDR3 encoded by the nucleic acid having at least 80%, 90%, 91%, 92%, 93%, 94%, 95%, 96%, 97%, 98%, 99% or more sequence identity with SEQ ID NO: 51; and (b) a VH comprising (i) a CDR1 encoded by the nucleic acid of SEQ ID NO: 41 or a CDR1 encoded by the nucleic acid having at least 80%, 90%, 91%, 92%, 93%, 94%, 95%, 96%, 97%, 98%, 99% or more sequence identity with SEQ ID NO: 41; (ii) a CDR2 encoded by the nucleic acid of SEQ ID NO: 43 or a CDR2 encoded by the nucleic acid having at least 80%, 90%, 91%, 92%, 93%, 94%, 95%, 96%, 97%, 98%, 99% or more sequence identity with SEQ ID NO: 43; and/or (ii) a CDR3 encoded by the nucleic acid consisting of SEQ ID NO: 45.

In some embodiments, the CARs disclosed herein further comprise a transmembrane domain. In some embodiments, the transmembrane comprises at least a portion of the transmembrane domain of the cluster of differentiation (CD) 28 protein. In some embodiments, the CD28 protein is a human CD28 protein. In some embodiments, the CD28 protein is a canine CD28 protein. In some embodiments, the CAR comprises a transmembrane domain of SEQ ID NO: 14 or a transmembrane domain having at least 80%, 90%, 91%, 92%, 93%, 94%, 95%, 96%, 97%, 98%, 99% or more sequence identity with SEQ ID NO: 14. In some embodiments, the CAR comprises a transmembrane domain encoded by the nucleic acid of SEQ ID NO: 15 or a transmembrane domain encoded by the nucleic acid having at least 80%, 90%, 91%, 92%, 93%, 94%, 95%, 96%, 97%, 98%, 99% or more sequence identity with SEQ ID NO: 15. In some embodiments, the transmembrane domain is fused to the extracellular antigen binding domain. In some embodiments, the transmembrane domain is fused to the C terminus of the extracellular antigen binding domain.

In some embodiments, the CARs disclosed herein further comprise an intracellular signaling domain. In some embodiments, the intracellular signaling domain comprises at least a portion of the signaling domain of the cluster of differentiation (CD) 3 protein. In some embodiments, the CD3 protein is a human CD3 protein. In some embodiments, the CD3 protein is a canine CD3 protein. In some embodiments, the CAR comprises an intracellular signaling domain of SEQ ID NO: 16 or an intracellular signaling domain having at least 80%, 90%, 91%, 92%, 93%, 94%, 95%, 96%, 97%, 98%, 99% or more sequence identity with SEQ ID NO: 16. In some embodiments, the CAR comprises an intracellular signaling domain encoded by the nucleic acid of SEQ ID NO: 17 or an intracellular signaling domain encoded by the nucleic acid having at least 80%, 90%, 91%, 92%, 93%, 94%, 95%, 96%, 97%, 98%, 99% or more sequence identity with SEQ ID NO: 17. In some embodiments, the intracellular signaling domain is fused to the transmembrane domain. In some embodiments, the intracellular signaling domain is fused to the C terminus of transmembrane domain.

In some embodiments, the CARs disclosed herein further comprise a leader sequence. In some embodiments, the leader sequence comprises at least a portion of the leader sequence of the cluster of differentiation (CD) 8 protein. In some embodiments, the CD8 protein is a human CD8 protein. In some embodiments, the CD8 protein is a canine CD8 protein. In some embodiments, the CAR comprises a leader sequence of SEQ ID NO: 12 or a leader sequence having at least 80%, 90%, 91%, 92%, 93%, 94%, 95%, 96%, 97%, 98%, 99% or more sequence identity with SEQ ID NO: 12. In some embodiments, the CAR comprises a leader sequence encoded by the nucleic acid of SEQ ID NO: 13 or a leader sequence encoded by the nucleic acid having at least 80%, 90%, 91%, 92%, 93%, 94%, 95%, 96%, 97%, 98%, 99% or more sequence identity with SEQ ID NO: 13. In some embodiments, the leader sequence is fused to the extracellular antigen binding domain. In some embodiments, the leader sequence is fused to the N-terminus of extracellular antigen binding domain.

In some embodiments, the CARs disclosed herein further comprise a surface marker. In some embodiments, the surface marker comprises at least a portion of the cluster of differentiation (CD) 34 protein. In some embodiments, the surface marker comprises a truncated portion of the CD34 protein (called CD34t). In some embodiments, the CD34 protein is a human CD34 protein. In some embodiments, the CD34 protein is a canine CD34 protein. In some embodiments, the CAR comprises a surface marker of SEQ ID NO: 22 or a surface marker having at least 80%, 90%, 91%, 92%, 93%, 94%, 95%, 96%, 97%, 98%, 99% or more sequence identity with SEQ ID NO: 22. In some embodiments, the CAR comprises a surface marker encoded by the nucleic acid of SEQ ID NO: 23 or a surface marker encoded by the nucleic acid having at least 80%, 90%, 91%, 92%, 93%, 94%, 95%, 96%, 97%, 98%, 99% or more sequence identity with SEQ ID NO: 23. In some embodiments, the surface marker is fused to the leader sequence. In some embodiments, the surface marker is attached to the leader sequence through a linker sequence.

In some embodiments, the CARs disclosed herein are "Third generation" CARs. In some embodiments, the CARs further provide costimulation via one or more costimulatory molecules (also called costimulatory ligands). In some embodiments, the costimulatory molecule comprises at least a portion of the 4-1BB ligand (4-1BBL). In some embodiments, the 4-1BBL is a human 4-1BBL. In some embodiments, the 4-1BBL is a canine 4-1BBL. In some embodiments, the CAR comprises a costimulatory molecule of SEQ ID NO: 18 or a costimulatory molecule having at least 80%, 90%, 91%, 92%, 93%, 94%, 95%, 96%, 97%, 98%, 99% or more sequence identity with SEQ ID NO: 18. In some embodiments, the CAR comprises a costimulatory molecule encoded by the nucleic acid of SEQ ID NO: 19 or a costimulatory molecule encoded by the nucleic acid having at least 80%, 90%, 91%, 92%, 93%, 94%, 95%, 96%, 97%, 98%, 99% or more sequence identity with SEQ ID NO: 19.

In some embodiments, the costimulatory molecule comprises at least a portion of the programmed cell death protein 1 dominant negative receptor (PD1-DNR). In some embodiments, the PD1-DNR is a human PD1-DNR. In some embodiments, the PD1-DNR is a canine PD1-DNR. In some embodiments, the PD1-DNR comprises a PD1 signal peptide. In some embodiments, the CAR comprises a costimulatory molecule of SEQ ID NO: 53 or a costimulatory molecule having at least 80%, 90%, 91%, 92%, 93%, 94%, 95%, 96%, 97%, 98%, 99% or more sequence identity with SEQ ID NO: 53. In some embodiments, the costimulatory molecule further comprises a signal peptide of SE ID NO: 57 or a signal peptide having at least 80%, 90%, 91%, 92%, 93%, 94%, 95%, 96%, 97%, 98%, 99% or more sequence identity with SEQ ID NO: 53. In some embodiments, the CAR comprises a costimulatory molecule of SEQ ID NO: 55 or a costimulatory molecule having at least 80%, 90%, 91%, 92%, 93%, 94%, 95%, 96%, 97%, 98%, 99% or more sequence identity with SEQ ID NO: 55. In some embodiments, the CAR comprises a costimulatory molecule encoded by the nucleic acid of SEQ ID NO: 54 or a costimulatory molecule encoded by the nucleic acid having at least 80%, 90%, 91%, 92%, 93%, 94%, 95%, 96%, 97%, 98%, 99% or more sequence identity with SEQ ID NO: 54. In some embodiments, the CAR comprises a costimulatory molecule encoded by the nucleic acid of SEQ ID NO: 56 or a costimulatory molecule encoded by the nucleic acid having at least 80%, 90%, 91%, 92%, 93%, 94%, 95%, 96%, 97%, 98%, 99% or more sequence identity with SEQ ID NO: 56.

Nucleic Acids

Genetic modification of immunoresponsive cells (e.g., T cells, CTL cells, NK cells) can be accomplished by transducing a substantially homogeneous cell composition with a recombinant DNA construct.

In one aspect, the present disclosure provides a nucleic acid encoding the antigen-binding protein or fragment or derivative thereof, isolated scFv, or a fusion protein described herein. In one embodiment, the nucleic acid encodes an antigen-binding peptide comprising one or more of amino acid sequences selected from the group consisting of SEQ ID NO: 4, 6, 8, 10, 12, 14, 16 and 18. In one embodiment, the nucleic acid comprises one or more coding sequences operably linked with one another. In some embodiments, the one or more coding sequences are selected from the group consisting of SEQ ID NO: 5, 7, 9, 11, 13, 15, 17 and 19.

In one embodiment, the nucleic acid encodes a chimeric antigen receptor (CAR) comprising an anti-CD20 scFv and one or more costimulatory domains selected from a CD28 extracellular signaling domain, a CD3 domain of T-cell receptor (TCR), and a 4-1BBL costimulatory domain. In some embodiments, the anti-CD20 scFv comprises the amino acid sequence set forth in SEQ ID NO: 8. In some embodiments, the CD28 extracellular signaling domain comprises the amino acid sequence set forth in SEQ ID NO: 14. In some embodiments, the CD3ζ domain comprises the amino acid sequence set forth in SEQ ID NO: 16. In some embodiments, the 4-1BBL costimulatory domain comprises the amino acid sequence set forth in SEQ ID NO: 18.

In one embodiment, the nucleic acid encodes a chimeric antigen receptor (CAR) comprising an anti-CD20 scFv and one or more costimulatory domains selected from a CD28 extracellular signaling domain, a CD3 domain of T-cell receptor (TCR), and a 4-1BBL costimulatory domain. In some embodiments, the nucleic acid comprises the coding sequence for an anti-CD20 scFv as set forth in SEQ ID NO: 9. In some embodiments, the nucleic acid comprises the coding sequence for the CD28 extracellular signaling domain as set forth in SEQ ID NO: 15. In some embodiments, the nucleic acid comprises the coding sequence for the CD3ζ domain as set forth in SEQ ID NO: 17. In some embodiments, the nucleic acid comprises the coding sequence for the 4-1BBL costimulatory domain as set forth in SEQ ID NO: 19.

In another related aspect, the present disclosure also provides an expression vector comprising a nucleic acid described herein, and a host cell transfected with an expression vector described herein.

In one embodiment, a retroviral vector (either gamma-retroviral or lentiviral) is employed for the introduction of the DNA construct into the cell. For example, a polynucleotide encoding a chimeric antigen receptor that binds an antigen (e.g., a tumor antigen, or a variant, or a fragment thereof), can be cloned into a retroviral vector and expression can be driven from its endogenous promoter, from the retroviral long terminal repeat, or from a promoter specific for a target cell type of interest. Non-viral vectors, such as CRISPR/Cas, can be used as well.

For initial genetic modification of the cells, to provide tumor or viral antigen-specific cells, a retroviral vector is generally employed for transduction, however any other suitable viral vector or non-viral delivery system can be used. For subsequent genetic modification of the cells, to provide cells expressing an antigen presenting complex comprising at least two co-stimulatory ligands, retroviral gene transfer likewise proves effective for transduction, however any other suitable viral vector or non-viral delivery system can be used. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); HEK293; and CRIP (Danos, et al. (1988) *Proc. Natl. Acad. Sci. USA* 85:6460-6464). Non-amphotropic particles are suitable too, e.g., particles pseudo-typed with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J Clin. Invest.* 89:1817.

Other transducing viral vectors can be used to express a co-stimulatory ligand of the present disclosure in an immunoresponsive cell. Preferably, the chosen vector exhibits high efficiency of infection and stable integration and expression (see, e.g., Cayouette et al., *Human Gene Therapy* 8:423-430, 1997; Kido et al., *Current Eye Research* 15:833-844, 1996; Bloomer et al., *Journal of Virology* 71:6641-6649, 1997; Naldini et al., *Science* 272:263-267, 1996; and Miyoshi et al., *Proc. Natl. Acad. Sci. U.S.A.* 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, *Human Gene Therapy* 15-14, 1990; Friedman, *Science* 244:1275-1281, 1989; Eglitis et al., *BioTechniques* 6:608-614, 1988; Tolstoshev et al., *Current Opinion in Biotechnology* 1:55-61, 1990; Sharp, *The Lancet* 337: 1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; Miller et al., *Biotechnology* 7:980-990, 1989; LeGal La Salle et al., *Science* 259:988-990, 1993; and Johnson, *Chest* 107:77S-83S, 1995). Retroviral vectors are particularly well developed and have been used in clinical settings (Rosenberg et al., *N. Engl. J. Med* 323:370, 1990; Anderson et al., U.S. Pat. No. 5,399,346).

Non-viral approaches can also be employed for the expression of a protein in a cell. For example, a nucleic acid molecule can be introduced into a cell by administering the nucleic acid in the presence of lipofection (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or by micro-injection under surgical conditions (Wolff et al., *Science* 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g., Zinc finger nucleases, meganucleases, CRISPR nucleases, or TALE nucleases). Transient expression can be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Immunoresponsive Cells

In some embodiments, the present disclosure provides engineered immunoresponsive cells that express a desired chimeric antigen receptor (CAR) or T cell receptor (TCR). Binding of the chimeric antigen receptor to a target antigen activates the immunoresponsive cells to provide an enhanced immune response. In some embodiments, the target antigen is a tumor antigen or pathogenic antigen.

Immunoresponsive cells can be obtained using any suitable method known in the art. In some embodiments, the immune cells are primary immune cells. In some embodiments, the immune cells are lymphocytes, such as T and B cells. In some embodiments, the immune cells are natural killer (NK) cells. In some embodiments, the immune cells are a mixture of lymphocytes and NK cells. In some embodiments, the immune cells are peripheral blood mononuclear cells (PBMC). In some embodiments, the immune cells are T cells that have infiltrated a tumor (e.g., tumor infiltrating lymphocytes). In some embodiments, the T cells are removed during surgery of a tumor. For example, in some embodiments, the T cells are isolated after removal of tumor tissue by biopsy. In some embodiments, the immune cells are modified following isolation from a donor.

The unpurified source of immunoresponsive cells can be any known in the art, such as the bone marrow, fetal, neonate or adult or other hematopoietic cell source, e.g., fetal liver, leukapheresis, peripheral blood or umbilical cord blood. Various techniques can be employed to separate the cells. For instance, negative selection methods can remove non-T lymphocytes or non-cytotoxic T lymphocytes (CTLs) initially. Monoclonal antibodies (mAbs) are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g., plate, chip, elutriation, fluidic method, or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% to 5% human serum, 2% fetal calf serum (FCS) or 0.2% bovine serum albumin (BSA) or any other suitable, preferably sterile, isotonic medium.

In some embodiments, the isolated immunoresponsive cells are genetically modified to target tumors or cancer cells through the introduction of vectors encoding a chimeric antigen receptor as described herein.

Methods of Treatment

In one aspect, the present disclosure provides methods for treating a B-cell cancer in a subject comprising administration of the CD20 antigen binding proteins or antigen binding fragments thereof or cells expressing the CD20 antigen binding proteins or antigen binding fragments thereof provided herein. Also contemplated herein are methods for treating autoimmune diseases comprising administration of the CD20 antigen binding proteins or antigen binding fragments thereof or cells expressing the CD20 antigen binding proteins or antigen binding fragments thereof provided herein. Also contemplated herein are methods for treating a pathogen infection or other infectious disease in a subject, such as an immunocompromised subject comprising administration of the CD20 antigen binding proteins or antigen binding fragments thereof or cells expressing the CD20 antigen binding proteins or antigen binding fragments thereof provided herein.

In some embodiments, an effective amount of the antigen-binding protein provided herein, or a fragment or analog thereof, are administered to alleviate one or more symptoms of a cancer, an autoimmune disease or an infectious disease. In some embodiments, the antigen-binding protein binds specifically to the extracellular domain of canine CD20 protein. In various embodiments, the antigen-binding protein is a full immunoglobulin, an antibody binding fragment (Fab) thereof, the variable regions thereof (Fv) or a recombinantly produced single chain variable fragment (scFv) thereof.

In another related aspect, the present method of treatment relates to cells comprising the nucleic acids or antigen binding proteins disclosed herein, including recombinant immunoresponsive cells, such as, CAR-T cells genetically modified to express a chimeric antigen receptor comprising an antigen binding region in accordance with the present disclosure. In some embodiments, the method of treatment comprises isolating immunoresponsive cells from a subject or a donor, transfecting the isolated cells with an expression vector comprising a nucleic acid encoding an isolated antigen-binding protein or fragment or derivative thereof described herein, and administering the transfected or transduced immunoresponsive cells to the subject.

In some embodiments, the B-cell cancer is a B-cell lymphoma or a B-cell leukemia. In some embodiments, the B-cell cancer is selected from among B-cell chronic lymphocytic leukemia, B-cell prolymphocytic leukemia, B-cell lymphoma, non-Hodgkin's lymphoma, or B-cell malignancies or other malignancies expressing CD20 or a cross reacting protein or peptide.

In some embodiments, the CD20 antigen binding proteins or antigen binding fragments thereof or cells expressing the CD20 antigen binding proteins or antigen binding fragments thereof are administered for treatment of canine CD20+ B-cell lymphoma, immune-mediated hemolytic anemia, immune-mediated thrombocytopenia, and systemic lupus erythematosus (SLE) or other disease or disorder associated with aberrant CD20 or B-cell expression (e.g., over-expression of B cells or CD20 or dysfunctional B cells).

In some embodiments, the autoimmune disease is selected from the group consisting of rheumatoid arthritis, systemic lupus erythematosus (SLE), Sjogren's syndrome, vasculitis, multiple sclerosis, Graves' disease, idiopathic thrombocytopenia, dermatomyositis, immune mediated thrombocytopenia, polymyocytosis, pemphigus, immune mediated hemolytic anemia and bullous pemphigoid.

The methods of treatment of the present disclosure comprising administration of the CD20 antigen binding proteins or antigen binding fragments thereof or cells expressing the CD20 antigen binding proteins or antigen binding fragments thereof provided herein encompass alleviation or prevention of at least one symptom or other aspect of a disorder, or reduction of disease severity as compared to a subject that has not been administered the CD20 antigen binding proteins or antigen binding fragments thereof or cells expressing the CD20 antigen binding proteins or antigen binding fragments thereof provided herein. An antigen-binding protein or fragment or derivative thereof, scFv, fusion protein, nucleic acid, expression vector, host cell, cell expressing a CAR, or pharmaceutical composition described herein need not effect a complete cure, or eradicate every symptom or manifestation of a disease, to constitute a viable therapeutic agent. As is recognized in the art, therapeutic agents can reduce the severity of a given disease state, but need not abolish every manifestation of the disease to be regarded as useful. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject as compared to a non-treated subject, is sufficient.

Dosages and the frequency of administration for use in the methods of the present disclosure can vary according to such factors as the route of administration, the particular antigen-binding proteins employed, the nature and severity of the disease to be treated, whether the condition is acute or chronic, and the size and general condition of the subject. Appropriate dosages can be determined by procedures known in the pertinent art, e.g., in clinical trials that can involve dose escalation studies. An antigen-binding protein or fragment or derivative thereof, scFv, fusion protein, nucleic acid, expression vector, host cell, cell expressing a CAR, or pharmaceutical composition of the present disclosure can be administered, for example, once or more than once, e.g., at regular intervals over a period of time. In various embodiments, time interval between administration of doses of the antigen-binding protein or fragment or derivative thereof, scFv, fusion protein, nucleic acid, expression vector, host cell, cell expressing a CAR, or pharmaceutical composition can be at least one, two, three, four, five, six, or seven days or one, two, three, four, five, six, seven, or eight weeks, or can be at least one, two, three, four, five, six, seven, eight, nine, ten, or eleven months, or at least one, two, three, or four years. In general, the antigen-binding protein or fragment or derivative thereof, scFv, fusion protein, nucleic acid, expression vector, host cell, cell expressing a CAR, or pharmaceutical composition is administered to a subject until the subject manifests a medically relevant degree of improvement over baseline for the chosen indicator or indicators.

In general, the amount of an antigen-binding protein or fragment or derivative thereof, scFv, or fusion protein described herein present in a dose, or produced in situ by an encoding polynucleotide present in a dose, ranges from about 0.01 pg to about 10 mg per kg of host. In one embodiment, cells expressing a CAR, are administered at a dose of $1.5 \times 10^6$ to $3.0 \times 10^6$ CAR-expressing cells/kg. Other host cells can also be administered at a dose of $1.5 \times 10^6$ to $3.0 \times 10^6$ cells/kg. The use of the minimum dosage that is sufficient to provide effective therapy is usually preferred. Patients can generally be monitored for therapeutic or prophylactic effectiveness using assays suitable for the condition being treated or prevented, which assays will be familiar to those having ordinary skill in the art and which are described herein. The methods disclosed herein can include oral administration of an antigen-binding protein or fragment or derivative thereof, scFv, or fusion protein or delivery by injection of a liquid pharmaceutical composition. A liquid pharmaceutical composition can include, for example, one or more of the following: a sterile diluent such as water for injection, saline solution, sodium chloride, fixed oils that can serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes, single or multiple dose bags or vials made of glass or plastic. The use of physiological saline is preferred, and an injectable pharmaceutical composition is preferably sterile. When administered in a liquid form, suitable dose sizes will vary with the size of the subject, but will typically range from about 1 ml to about 500 ml (comprising from about 0.01 pg to about 10 mg per kg) for a 10-60 kg subject. Optimal doses can generally be determined using experimental models and/or clinical trials. The optimal dose can depend upon the body mass, body area, weight, or blood volume of the subject. As described herein, the appropriate dose can also depend upon the patient's (e.g., human) condition, that is, stage of the disease, tumor burden, general health status, as well as age, gender, and weight, and other factors familiar to a person skilled in the medical art.

In particular embodiments of the methods described herein, the subject is a human or non-human animal. A subject in need of the treatments described herein can exhibit symptoms or sequelae of a disease, disorder, or condition described herein or can be at risk of developing the disease, disorder, or condition. Non-human animals that can be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

In some embodiments, the antigen-binding protein or fragment or derivative thereof, scFv, fusion protein, nucleic acid, expression vector, or host cell described herein are administered in combination with one or more therapeutic agents. In some embodiments, the CD20 antigen binding proteins or antigen binding fragments thereof or cells expressing the CD20 antigen binding proteins or antigen binding fragments thereof provided herein are administered in combination with one or more therapeutic agents.

In some embodiments, the therapeutic agent is an immunosuppressant, anti-cancer agent, an inhibitor of mitogen-activated protein kinase (MAPK) signaling. In some embodiments, the anti-cancer agent is a proapoptotic agent. In some embodiments, the anti-cancer agent is selected from the group comprising gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allyl amino-17-Demethoxygeldanamycin (17-AAG), flavopiridol, L Y294002, bortezomib, trastuzumab, BAY 11-7082, PKC412, or PD184352, Taxol™, also referred to as "paclitaxel", analogs of Taxol™, such as Taxotere™. In some embodiments, the anti-cancer agent is selected from the group comprising Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; bendamustin; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon a-2a; interferon a-2b; interferon a-nl; interferon a-n3; interferon b-1 a; interferon y-1 b; iproplatin; irinotecan hydrochloride; lameotide acetate; lenalidomide; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine;

meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vimosidine sulfate; vinzolidine sulfate; vorozole; zeniplatin; zinostatin; zombicin hydrochloride.

Examples of inhibitors of MAPK signaling include, but are not limited to, U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Compositions

In another aspect, the present disclosure provides a pharmaceutical composition comprising an antigen-binding protein or fragment or derivative thereof, scFv, fusion protein, nucleic acid, expression vector, or host cell described herein, and a physiologically acceptable diluent, excipient, or carrier. Optionally, the composition additionally comprises one or more physiologically active agents, for example, a second inflammation- or immune-inhibiting substance, an anti-angiogenic substance, an analgesic substance, etc. In various particular embodiments, the composition comprises one, two, three, four, five, or six physiologically active agents in addition to an antigen-binding protein or fragment or derivative thereof, scFv, fusion protein, nucleic acid, expression vector, or host cell.

In one aspect, a pharmaceutical composition of the present disclosure comprises an antigen-binding protein or fragment or derivative thereof described herein with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol can also be added. The composition can be formulated as a lyophilizate using appropriate excipient solutions (e.g., sucrose) as diluents. Suitable components are nontoxic to recipients at the dosages and concentrations employed. Further examples of components that can be employed in pharmaceutical formulations are presented in Remington's Pharmaceutical Sciences, 16tA Ed. (1980) and 20tA Ed. (2000), Mack Publishing Company, Easton, Pa.

As is understood in the art, pharmaceutical compositions comprising the molecules of the present disclosure are administered to a subject in a manner appropriate to the indication. A pharmaceutical composition of the present disclosure comprising an antigen-binding protein or fragment or derivative thereof, scFv, fusion protein, or cell expressing a CAR described herein can be formulated for delivery by any route that provides an effective dose of the immunogen. Pharmaceutical compositions can be administered by any suitable technique, including but not limited to parenterally, topically, or by inhalation. If injected, the pharmaceutical composition can be administered, for example, via intraarticular, intravenous, intramuscular, intralesional, intraperitoneal, intratumoral, or subcutaneous routes, by bolus injection, or continuous infusion. Localized administration, e.g., at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including tablets, capsules, syrups, lozenges or chewing gum; and topical preparations such as lotions, gels, sprays, patches, and ointments.

Kits

In another aspect, the present disclosure provides a kit comprising an antigen-binding protein or fragment or derivative thereof, scFv, fusion protein, nucleic acid, expression vector, host cell, cell expressing a CAR, or pharmaceutical composition described herein. Kits for use by medical practitioners include an antigen-binding polypeptide of the present disclosure and a label or other instructions for use in treating any of the conditions discussed herein. Instructions typically describe methods for administration, including methods for determining the proper state of the subject, the proper dosage amount, and the proper administration method, for administering the composition. Instructions can also include guidance for monitoring the subject over the duration of the treatment time. Kits provided herein also can include devices for administration of a pharmaceutical composition described herein to a subject. Any of a variety of devices known in the art for administering medications, immunogenic compositions, and vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a composition is compatible with the active components of the kit.

EXAMPLES

Example 1. Synthesis of Canine CD20 Antigen

In this example, an exemplary canine CD20 extracellular antigen was chemically synthesized. The CD antigen contains a CD20 epitope sequence that includes the 17 amino acids of the smaller extracellular loop of canine CD20 and six additional amino acids of the larger extracellular loop: YVDIHNCDPANPSEKNSLSIQYC (SEQ ID NO: 20). The two cysteine residues form a sulfhydryl bond that cyclizes peptide. The presence of the ring and formation of a partial secondary structure of the cyclic peptide is intended mimic that of native extracellular loop of CD20. This allows for antibody recognition that is conformational as opposed to linear as in the case of the linear 16 amino acid epitope for rituximab (YNCEPANPSEKNSPST (SEQ ID NO: 21)).

Additional design elements were included in the CD20 antigen synthesis procedure to facilitate the chemical synthesis of the antigen construct and/or focus immunogenicity on the CD20 epitope sequence rather than the spacer elements. For example, the N-terminal amino acid in the construct was kept as a free amino group instead of an acetylated N-terminus in order to give an advantage to immunogenicity towards N-acetylated termini. A spacer, Gly-Ser-Gly-Gly-Gly (SEQ ID NO: 58), was inserted on the C terminal side of the CD20 epitope sequence to insure proper separation and presentation by the carrier protein, Keyhole limpet hemocyanin (KLH). The peptide terminates in a lysine that is further linked to a terminal sulfhydryl group to facilitate linking chemistry to the carrier protein. FIG. 4 illustrates the exemplary canine CD20 antigen construct prior to attachment of the carrier protein.

The number of sulfhydryl groups present on the CD20 epitope and their structural arrangement vis-a-vis the small extracellular loop and its correct formation and consequent conformation presented a challenge to chemical synthesis of the antigen. In particular, there are two sulfhydryl groups emanating from the two cysteine side chains at positions 7 and 23 of SEQ ID NO:20 (i.e., cysteines 167 and 183 of the full-length CD20), which must form the extracellular loop, and a terminal sulfhydryl, which is used for linking to KLH. Together, the three sulfhydryl groups have the tendency to scramble at oxidation or cyclization step should they be liberated at the same time and could form a multitude of cyclic peptides as well as linear polymers connected through S—S bonds. Therefore, the synthesis steps and protecting group strategy was planned such that only the two cysteine side chains are released for cyclization in a synchronous manner with the terminal sulfhydryl protected during cyclization reaction.

Figure 21:
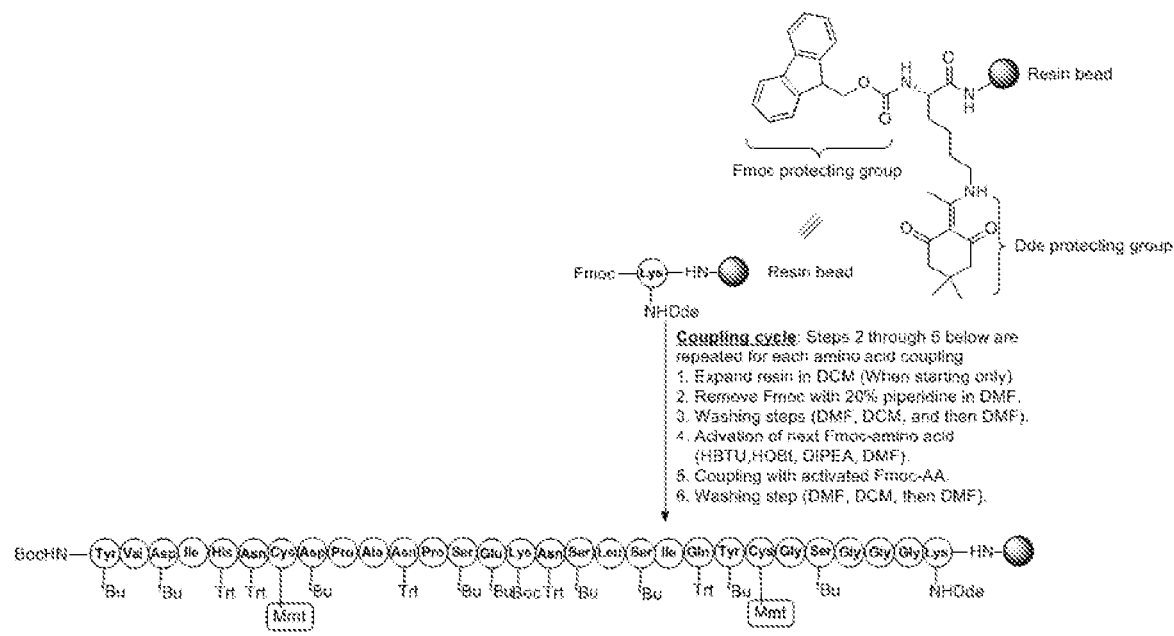
FIG. 21 illustrates an exemplary schema for solid phase peptide synthesis and protecting group strategy.

FIG. 21 illustrates exemplary synthesis steps and protecting group strategy. As shown in FIG. 21, sulfhydryl group protections were orthogonal here as they permitted the selective removal and oxidation of only the pair that was to be cyclized. Some of the amino acid coupling could be executed using commercially available pairs that properly functionalized for use in an automatic synthesis setting. For example, the Ser-Leu pair (in purple) was introduced as a pre-functionalized and properly protected dimer which is commercially available.

An additional connecting group was used to connect the terminal sulfhydryl group to KLH. The additional connecting groups also provided further flexibility as well as ease of synthesis by offering a better protecting group control, for example, in order to execute on-bead transformations prior to release of the full construct. As shown in FIG. 21, lysine with an orthogonal protecting group such as Dde at its side chain was removed on-bead without deprotecting the other amino acids side chains. Once the lysine side chain was released from Dde protecting group, an S-trityl mercapto propionic acid was connected to the liberated ε-amino group resulting in the full construct on-bead. As shown in FIG. 21, in anticipation of a final unified and global deprotecting step under the same trifluoroacetic acid condition, this attachment is brought in as an acid-labile trityl group whose removal conditions are comparable to all side chain protecting groups in black; tertiobutyl esters ($^t$Bu) and tertiobutyoxy carbonyl (Boc) protecting groups, which are much harder to remove than the monomethoxytrityl (Mmt) groups on the side chain sulfhydryl groups of the two cysteines (in fluorescent green).

Figure 22:
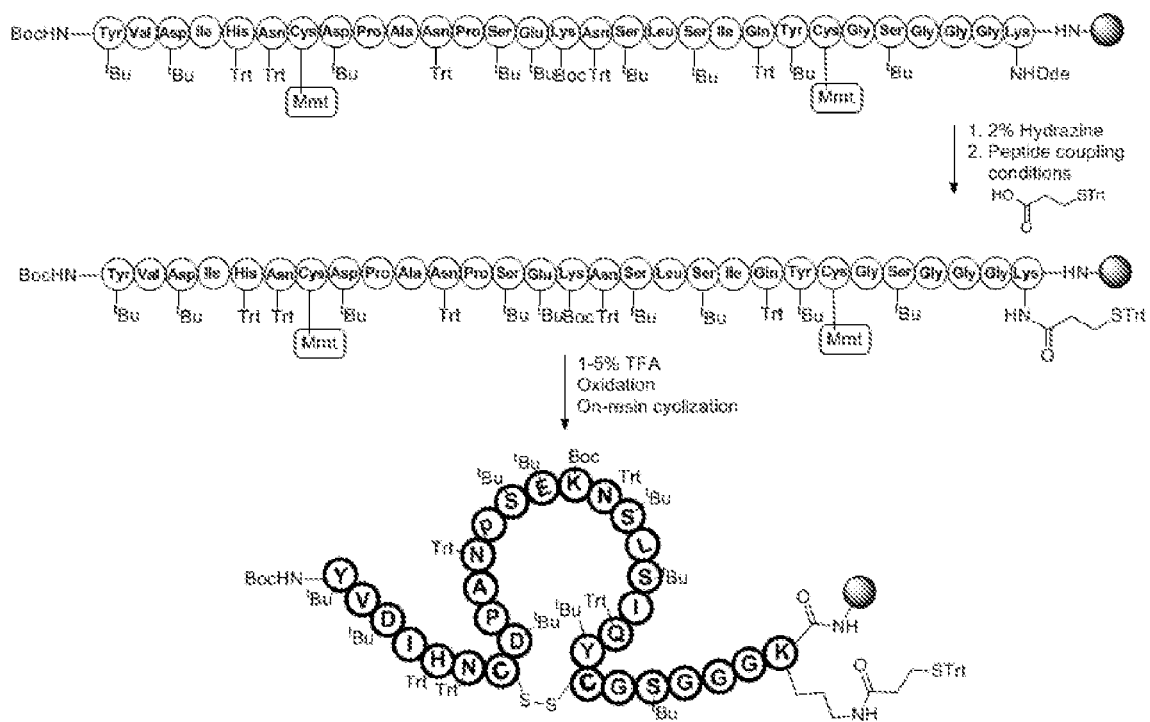
FIG. 22 illustrates an exemplary schema for solid phase peptide synthesis and the selective deprotection of cysteine side chains.

Selective oxidation of cysteines 167 and 183 and final deblocking of the whole sequence under non-reducing conditions resulted in generation of the crude construct. As shown in FIG. 22, the side chain cysteines (in fluorescent green) were selectively deprotected with low concentration TFA (1-5%) under oxidizing conditions which led directly to the selective S—S bond formation which consequently cyclized the peptide into a ring. This would have been a difficult task in homogeneous phase.

Figure 23:
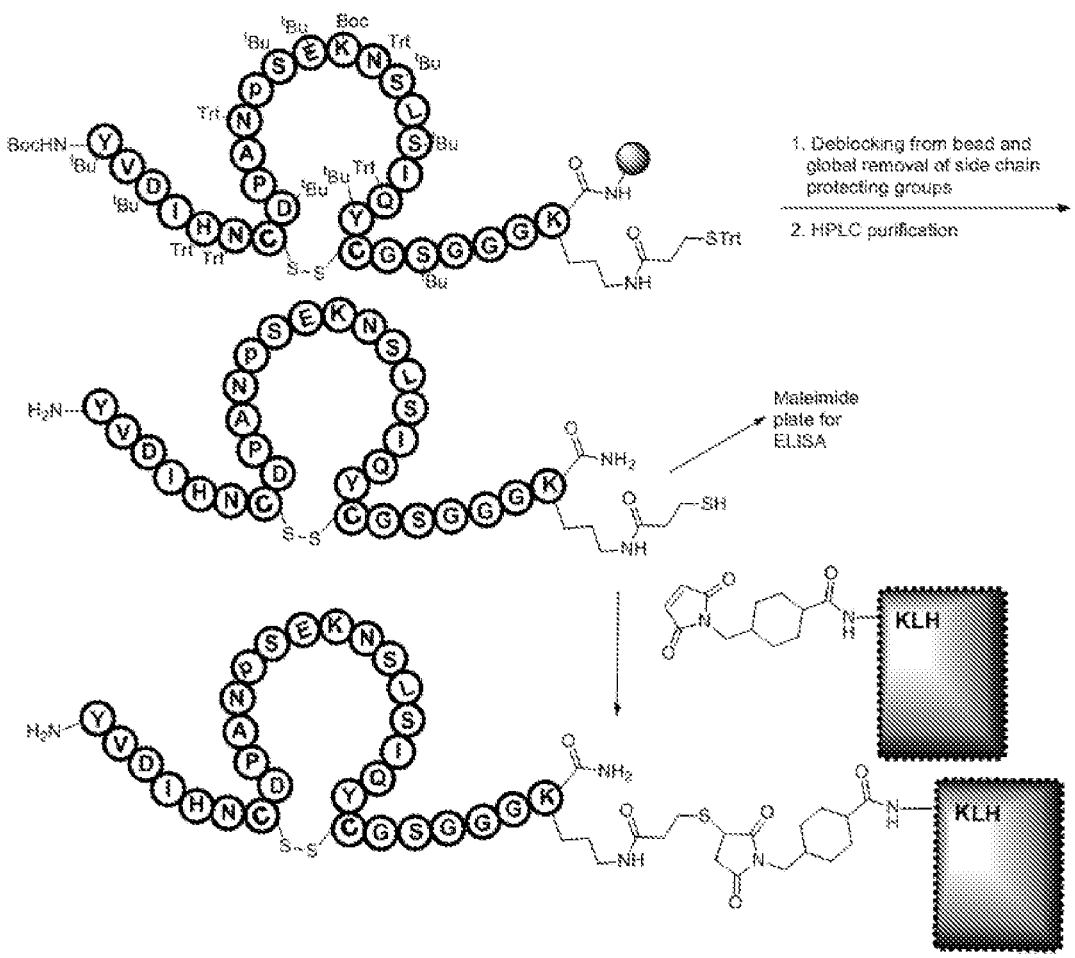
FIG. 23 illustrates an exemplary schema for solid phase peptide synthesis and conjugation to KLH.

As shown in FIG. 23, once the peptide cyclized selectively, all protecting groups were removed and the peptide was deblocked (removed) from resin under non-reducing conditions followed by HPLC purification also under non-reducing conditions, lyophilization provided the pure peptide which was divided between a part that was conjugated to KLH for inoculation, a smaller part was used as target for ELISA follow up assessments, and the third part was used for affinity purification.

Once the crude construction was precipitated and purified to a high level (e.g., 99% or higher) and lyophilized, the fractions containing the product were then conjugated to KLH preactivated with a cross-linker, Sulfo-SMCC ((sulfosuccinimidyl 4-(N-maleimidomethyl)cyclohexane-1-carboxylate)) (FIG. 5).

Example 2. Immunization of Rats with Synthetic Canine CD20 Peptide

Synthetic canine CD20 peptide as generated above was used to immunize rats. Particularly, four rats were each immunized subcutaneously with 50 μg of KLH-peptide conjugate (aka CP-29-KLH) emulsified in TiterMax® adjuvant 8 times over the course of 7 months. Then the rats rested for 22 weeks before antigen specific memory B cells were stimulated with acute intravenous boost of the KLH-peptide conjugate (no adjuvant). 3 days after, the animals were sacrificed and splenocytes were prepared for generation of hybridoma cells lines for monoclonal antibody selection.

A pre-immune bleed was taken prior to administering the first immunization dose, and production-bleeds were taken according to the following immunization and bleed schedule:

| Procedure | Day | Procedure | Day |
|---|---|---|---|
| Prime | 1 | | |
| Boost 1 | 21 | Test bleed 1 | 28 |
| Boost 2 | 42 | Test bleed 2 | 49 |
| Boost 3 | 63 | Test bleed 3 | 70 |
| Boost 4 | 84 | Test bleed 4 | 98 |
| Boost 5 | 119 | Test bleed 5 | 126 |
| Boost 6 | 175 | Test bleed 6 | 182 |
| Boost 7 | 210 | Test bleed 7 | 217 |
| Long Rest | | | |
| Fusion | 371 | | |

Antibody production in the bleeds was monitored using enzyme-linked immunosorbent assay (ELISA). After the color-changing assay was completed, the optical density (OD) value of each sample was measured as an indicator of antibody titer within that sample, as antibody titer correlates positively with the OD value.

Figure 6A:
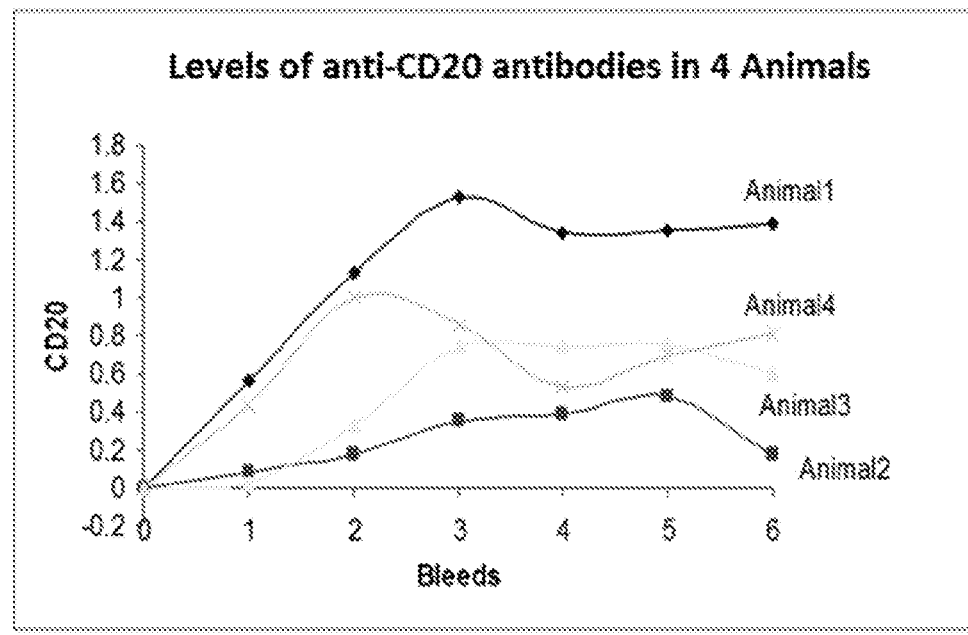
FIG. 6A and FIG. 6B each illustrate one replica of ELISA screening of all bleeds collected from four rats immunized with a synthetic canine CD20 antigenic peptide, according to one embodiment of the present disclosure.
Figure 6B:
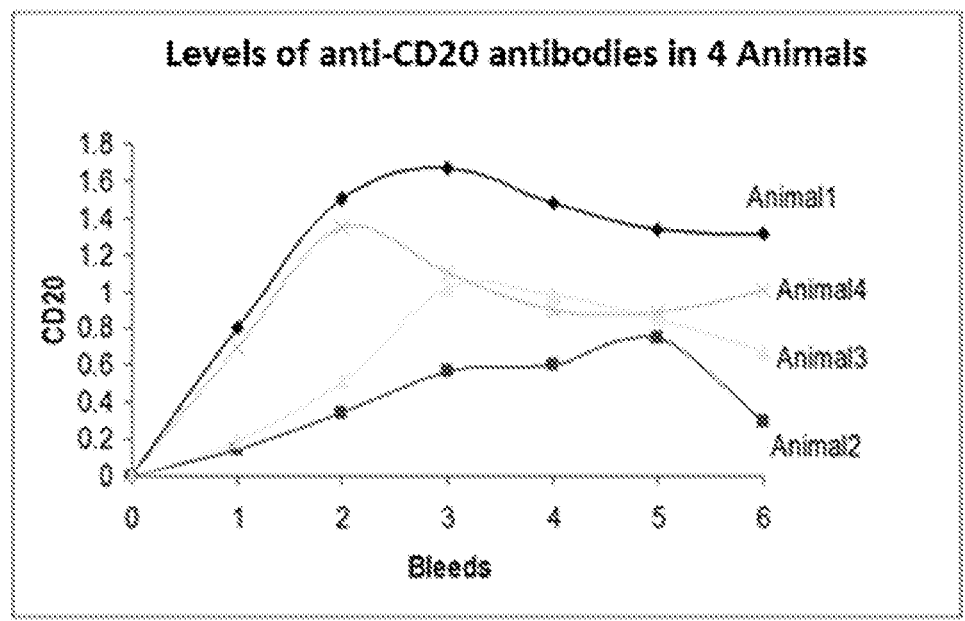

All bleeds collected from the immunized animals were screened with ELISA. Duplicate ELISA assays were performed, and the date are summarized in Tables 4 and 5, and plotted in FIGS. 6A and 6B, respectively. In FIGS. 6A and 6B, animal 1 is represented by the diamond, animal 2 is represented by the square, animal 3 is represented by the triangle, and animal 4 is represented by the x. As shown by the results, the immunization scheme triggered antibody production in all immunized animals.

TABLE 4

Optical density values in ELISA replica I

| Bleed | Animal | | | |
|---|---|---|---|---|
| | 1 | 2 | 3 | 4 |
| 0 | −0.001 | −0.001 | −0.001 | −0.001 |
| 1 | 0.57 | 0.08 | 0.02 | 0.43 |
| 2 | 1.13 | 0.18 | 0.33 | 1.00 |
| 3 | 1.53 | 0.35 | 0.74 | 0.86 |
| 4 | 1.34 | 0.39 | 0.74 | 0.53 |
| 5 | 1.35 | 0.48 | 0.76 | 0.70 |
| 6 | 1.39 | 0.18 | 0.60 | 0.81 |

TABLE 5

Optical density values in ELISA replica II

| Bleed | Animal | | | |
|---|---|---|---|---|
| | 1 | 2 | 3 | 4 |
| 0 | 0.001 | 0.001 | 0.001 | 0.001 |
| 1 | 0.81 | 0.14 | 0.19 | 0.70 |
| 2 | 1.51 | 0.35 | 0.51 | 1.35 |
| 3 | 1.67 | 0.57 | 1.01 | 1.10 |
| 4 | 1.48 | 0.60 | 0.98 | 0.90 |
| 5 | 1.34 | 0.74 | 0.86 | 0.88 |
| 6 | 1.31 | 0.30 | 0.68 | 1.01 |

Figure 7:
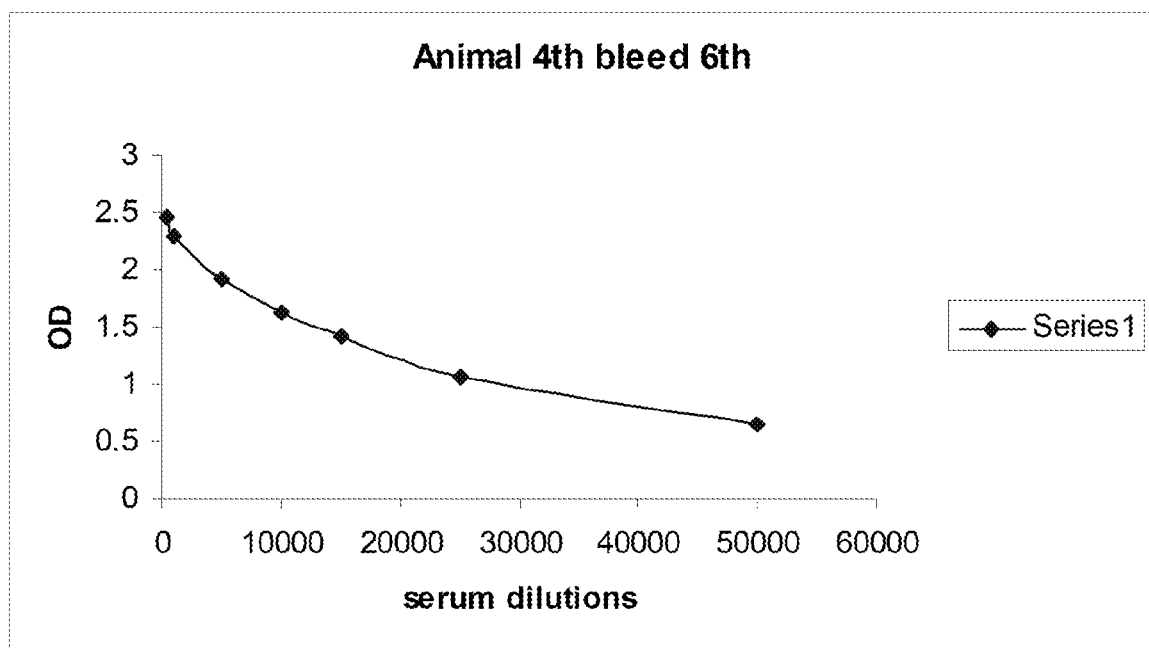
FIG. 7 illustrates a plot of ELISA OD values versus sample concentrations for serial dilutions of serum collected from a rat immunized with a synthetic canine CD20 antigenic peptide, according to one embodiment of the present disclosure.

A serial dilution was performed on the last bleed of Rat No. 4, and the resulting diluted samples were screened by ELISA. The results were summarized in Table 6, and plotted in FIG. 7. As shown, further diluted samples with lower expected antibody titers consistently showed lower OD values, thus confirming the positive correlation between antibody titer and the OD value in this assay.

TABLE 6

Optical density values of serial dilutions of Animal 4, 6th bleed after immunization

| dilutions | OD | OD | OD | OD |
|---|---|---|---|---|
| 500 | 2.298 | 2.673 | 2.408 | 2.459667 |
| 1000 | 2.298 | 2.302 | 2.252 | 2.284 |
| 5000 | 1.992 | 1.868 | 1.869 | 1.909667 |
| 10000 | 1.607 | 1.638 | 1.615 | 1.62 |
| 15000 | 1.476 | 1.413 | 1.36 | 1.416333 |
| 25000 | 1.126 | 1.028 | 1.036 | 1.063333 |
| 50000 | 0.67 | 0.642 | 0.61 | 0.640667 |

Specificity of the CD20 antibody produced by the immunized animals was analyzed by western blot. NIH3T3 cells were transduced with IRES-puro vectors encoding a canine CD20 peptide of between 32 to 36 kilo Dalton (kD) (T). Untransduced 3T3 cells were used as a negative control (UT). The cells were lysed and the contents were homogenized before loading onto a SDS-PAGE gel. A suitable size standard was also included.

Protein electrophoresis and western blotting were performed according to standard protocols. Particularly, for western blotting, serum of bleeds were diluted 1000 fold before use as the source of primary antibody (anti-CD20), and an anti-rat secondary antibody was used.

Figure 8:
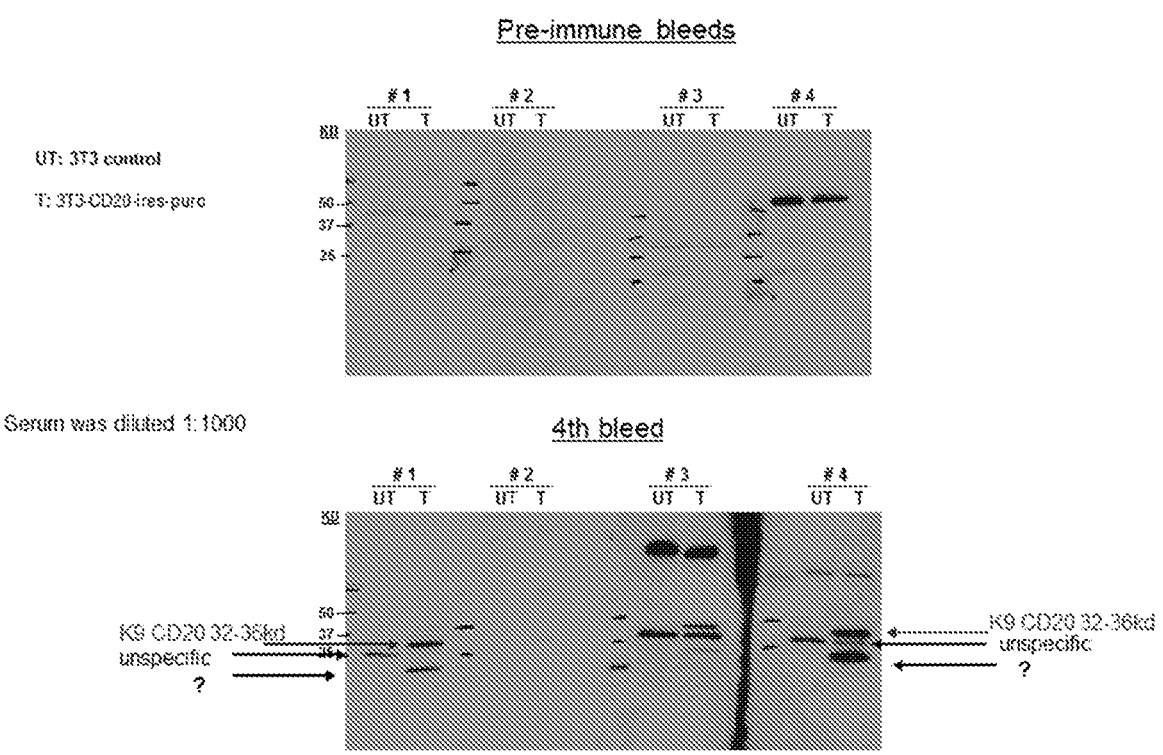
FIG. 8 illustrates anti-canine CD20 specificity of antibodies produced by animals immunized with a synthetic canine CD20 antigenic peptide, according to one embodiment of the present disclosure.
Figure 9:
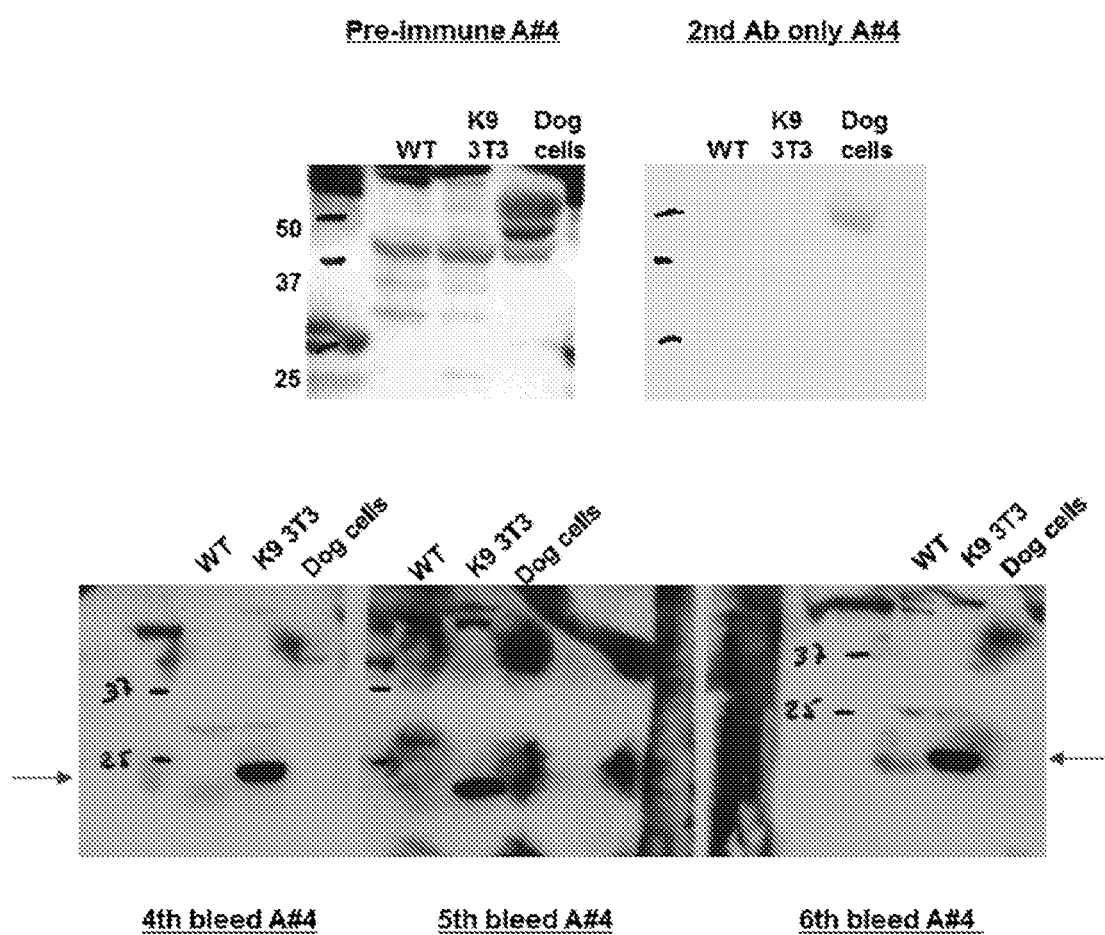
FIG. 9 illustrates anti-canine CD20 specificity of antibodies produced by animals immunized with a synthetic canine CD20 antigenic peptide for cells expressing canine CD20 (K9 3T3) versus normal dog cells.

The western blot results are shown in FIG. 8. The upper panel shows the results for the pre-immune bleeds of the four immunized animals. As expected, no specific band was recognized by western blotting, as the pre-immune bleeds were expected to lack anti-canine CD20 activity. By comparison, the lower panel shows the results for the 4$^{th}$ production bleeds from the four immunized animals. All samples show the specific 32-36 kD band corresponding to the canine CD20 peptide expressed by the transduced 3T3 cells, which was missing for all negative controls using untransduced 3T3 cells, as expected. These results confirm anti-canine CD20 specificity of the antibody produced by immunization of animals using the synthetic canine CD20 peptide.

Example 3: Construction of Hybridoma Cell Lines

An exemplary protocol for producing hybridoma cell lines is described in this Example. The hybridoma cell lines were generated by fusing myeloma cells with splenocytes. The splenocytes were obtained from rats that were immunized with CD20 antigen as described in Examples 1 and 2.

Day 1:

Myeloma cells, P3x63Ag8.653, were passaged twice: early in the morning with HSFM+10% FBS at $0.5 \times 10^6$ viable cells/ml; and at the end of the day to with HT media at $0.25 \times 10^6$ viable cells/ml.

Day 2:

Before 10 am, the myeloma cells were passaged with HT media to a concentration of $0.5 \times 10^6$ viable cells/ml.

The spleen was harvested using a standard protocol from rats that were immunized with CD20 antigen and placed in a conical tube containing HT media. Generally, rats were euthanized with carbon dioxide as per the American Veterinary Medical Association guidelines, the surgical area on the rats was disinfected, the abdominal cavity was opened, and the spleen was dissected out.

Blood was collected from the rat by cutting open the chest of the rat such that the blood pools in the thoracic cavity after the heart is cut. The blood was transferred into a microfuge tube using a 1 ml syringe without a needle. To maximize recovery of the blood, the lungs were removed prior to cutting the heart. Sera was prepared from the blood using a standard protocol.

The spleen and HT media were poured into a 60 mm petri dish. Without disrupting the capsule of the spleen, non-splenic tissue was removed from the spleen. The spleen was transferred to a new 60 mm petri dish.

A single cell suspension of splenocytes was obtained by employing the "syringe" method, followed by the "slide" method. To perform the "syringe" method, a 10 cc syringe was filled with HT media. A 26-gauge needle was attached to the syringe. HT media was slowly injected into the spleen with the bevel side of the needle up, such that the spleen swelled and RBCs leaked out. Once the injection spot of the spleen appears pale, the syringe was removed and the process of slowly injecting the HT media into the spleen was repeated throughout the spleen. If the spleen did not become pale/translucent after injecting the HT media, the syringe was not refilled with the cell/media mixture. After performing the "syringe" method, the "slide" method was performed by pressing the spleen between the frosted areas of two slides until the spleen started breaking into clumps. The bulk of the organ was pushed above the frosted area and the clumps were dissociated by gently rubbing them between the frosted areas. The cells were rinsed off the frosted areas into the HT. The "slide" method was repeated until the spleen appeared completely white or did not become paler.

The splenocyte suspension was passed through a single cell filter into a 50 ml conical tube to remove aggregates.

A petri dish was rinsed with ~2 mls of HT media and the media was passed through the same single cell filter that the splenocyte suspension was passed through into the same 50 ml conical tube that the splenocytes were collected in.

Cells in the 50 ml conical tube were mixed and ~100 ul of the cell suspension was used for counting.

The total cell number and viability of the nucleated splenocytes and myelomas were determined by dye exclusion technique. Generally, the cells were mixed with eosin (final concentration of 1%) in phosphate buffered saline and immediately counted with a hemocytometer.

Myeloma cells were added to the splenocytes to obtain a final ratio of 5 nucleated splenocytes:1 myeloma (Total # not Viable #). If necessary, multiple tubes could be used to hold the myeloma cells and the multiple tubes can be combined later.

For a control sample, 20 mls of the myeloma were diluted with 20 mls of Fusion Recovery Media and incubated until plating.

The cell mixture was centrifuged. Without disturbing the pellet, the media was aspirated.

Cells were resuspended in 45 ml serum free HSFM. If multiple tubes were used to centrifuge the myeloma cells, the myeloma cells were combined into the tube containing the splenocytes.

If cell aggregates developed as the sera was washed away, the cell aggregates were removed by passing the cell suspension through another single cell filter.

Repeat the centrifugation step three times, resuspension step two times, and removal of cell aggregates step as needed.

During the final centrifugation, the following items (pre-warmed at just above 37° C.) were placed into the hood:
large beaker of water
a container (i.e. in a destain box) of warm water with a rack containing:
15 ml conical with 500 ul 50% PEG and a 2 ml pipet
50 ml conical with 15 ml HSFM and a 25 ml pipet.

After the final centrifugation, without disrupting the cell pellet, the media was aspirated.

The cell pellet was disrupted by flicking/tapping the bottom of the tube

The cells were warmed up in the 37° C. beaker of water for 1 minute with mild agitation (by tapping the tube against the wall of the beaker).

Taking care not to touch the cells with the pipet, but rather to coat the walls of the tube, 500 ul of 50% PEG was added to the cells over 45 seconds, with gentle and constant agitation in the 37° C. beaker of water The cells/PEG mixture was immediately diluted with 15 ml HSFM in a drop-wise fashion, over 90 seconds (5 ml/30 seconds), and with gentle and constant agitation in the 37° C. beaker of water.

The cells were incubated without agitation for 8 min at RT in 50 ml conical tube styrofoam rack, then 2 min at just above 37° C. (~40° C.).

The fusion mixture was centrifuged for 4 minute at 450×g, which is just before "5" on the Fisher clinical centrifuge (Centrific™, Model #225, Cat #04-978-50).

The fusion was stopped immediately by aspirating as much media as possible without disturbing the pellet.

The pellet was resuspended by gently tapping the tube 3 to 5 times.

Resuspension of the pellet was continued with a large bore (i.e. 25 ml) pipet and 30 ml of fresh Fusion Recovery Media by pipetting up and down a few times without forcing the cells between the pipet and bottom of the tube.

Any remaining clumps were allowed to settle for a few seconds and then "single" cells were transferred into T75 flask(s).

"Single" cells were continued to be recovered from the tube by additional aliquots of Fusion Recovery Media and added to the flask(s). If the clumps did not break apart easily, each subsequent wash volume was pipetted more forcefully.

The final suspension of cells should be approximately 2.5 to $3 \times 10^6$ pre-fusion viable cells/ml if recovering >8 hours (preferred) or approximately 4 to $4.5 \times 10^6$ pre-fusion viable cells/ml if recovering for 4 to 8 hours.

The cells in the T25 flask(s) were incubated for 4 to 20 hours in the cell culture incubator.

Day 3:

150 ul/well of 1.3×HAT media was dispensed into 96 well plates and each well was numbered.

In a sterile trough, fused cells were diluted with Fusion Recovery Media to obtain a concentration of $100 \times 10^6$ pre-fusion viable nucleated/lymphoid in 50 ml ($0.1 \times 10^6$/50 ul).

Without delay, 50 ul of the diluted fusion suspension was dispensed into 10 of the 96 well plates pre-filled with HAT media.

The dilution and dispension of fused cells were repeated until the desired number of plates were made (i.e. 25). If final set of plates was less than 10, the same cell concentration as maintained by adjusting the volume of Fusion Recovery Media added to the wells.

50 ul/well of the control sample (consisting of 20 ml of myeloma cells diluted with 20 ml of Fusion Recovery Media) was plated into 1 pre-filled 96 well plate.

Plates were incubated for 5 to 8 days undisturbed. One or two plates can be checked for growth, but care should be taken to not disturb colonies.

Days 7 to 10:

To determine fusion efficiency, the number of clones was counted (cluster of ≥10 spherical/glowing cells) using a 4× objective, usually on day 8 or 9. The number of colonies/well and percent wells with hybridoma growth were recorded.

The fusion was fed on day 9 or 10 by aspirating the media and adding 150 ul Fusion Recovery Media. If the clones were particularly small (most colonies are <25 cells) or infrequent (<0.5 clones/well), then feeding began on the Day 7 or 8. If the clones were particularly large (e.g., can be seen by the naked eye on day 7 or 8) and show noticeable growth by day 9 or 10, then feeding was delayed until day 13.

Day 23 to 30:

For Quality Control data, the number hybridomas from all plates was counted and the percent of wells from all plates that contained hybridomas was calculated. The number of colonies/well was adjusted with this final count.

Materials used in Example 3:
Myelomas:
P3x63Ag8.653 For rats/hamsters (ATCC/Cat #CRL-1580)
Reagents:
Gentamycin: (Invitrogen/Cat. #15710-064)
50% PEG 1500: in 75 mM Hepes (w/v) (Roche/Cat. #783 641)
Hypoxanthine, Thymidine (HT): (100× from Invitrogen/Cat. #11067-030)
Hypoxanthine, Aminopterin, Thymidine (HAT): (50× HAT from Sigma/Cat. #H0262)
Media/Supplements:
Hybridoma Serum Free Media (HSFM) (Invitrogen/Cat. #12300-067 . . . for powder)

(Invitrogen/Cat. #12045-076 . . . 1000 ml liquid)
(Invitrogen/Cat. #12045-084 . . . 500 ml liquid)
Fetal Bovine Serum (FBS) (pre-screened fusion/cloning quality)
Growth Factor Supplement Need to be titered for each new lot
For rat/hamster fusions Hybridoma Cloning Factor (HCF)
Fusion Base Media:
HSFM
15% FBS
1× Appropriate Growth Factor Supplement
10 mg/ml Gentamycin
HT Media (Fusion Growth Media):
Fusion Base Media
1×HT
Fusion Recovery Media:
HT media
2× Growth Factor Supplement
1.3×HAT Media (Fusion Selection Media=1×):
Fusion Base Media
2× Growth Factor Supplement rather than 1×
1.3×HAT
Equipment:
Cell Culture Incubator maintained at:
37° C.
7% CO2
Humidified
Misc Items:
500 ml FRESH 70% EtOH made in bottle
60 mm petri dishes
1 ml syringe
10 ml syringe and 26 g needle
Sterile frosted glass slides for disrupting spleen—
Prepared by scraping the excess frosting off with the edge of another slide, washing glass dust off the slides with ultra pure water and autoclaving the slides in sets of 2/bag.
Sterile single cell filter (Fisher/Cat #08-771-1)
Sterile flat bottom 96 well tissue culture plates
Construction of Cells Expressing the K9CD20 Antigen
Construction of SFG-K9CD20-dsRed Plasmid The plasmid SFG-K9CD20-dsRed was used to express K9CD20 antigen in NIH3T3, EL4 and NALM-6 cells. It was prepared by replacing the IRES-Puro elements of the SFG-K9CD20-IRES-Puro construct with P2A-dsRed. K9CD20P2AdsRed was generated with overlapping PCR using equal molar mixture of 2 PCR fragments. Fragment 1 consisting of PmlI-K9CD20 and P2A was generated using primers k9CD20-F1: 5'-GGCCCACGTGGCCAC-CATGACAACACCCAGAAATT-3' (SEQ ID NO: 30) and K9CD20-R1: 5'-GGGTCCGGGATTCTCCACGT-CACCTGCTTGTTTGAGTAGTGAGAAGTTTGTTGCTCCAGATCCAGGGATGCTGTCGTTTTCTATTGGT-3' (SEQ ID NO: 31) using SFG-K9CD20-IRES-Puro. Fragment 2 consisting of P2A C-terminal sequence-dsRed-BamHI site was generated with primers K9CD20-F2:5'-CAAGCAGGTGACGTGGAGGAGAATCCCGGACCCA TGGACAACACCGAGGACGT CAT-3' (SEQ ID NO: 32) and k9CD20-R2:5'-TTAAGGATCCCTACTGGGAGCCG-GAGTGGCGGG-3' (SEQ ID NO: 33) using SFG-PZ1-IRES-dsRed as template. The primers used for overlapping PCR were K9CD20-F1 and K9CD20-R2. K9CD20dsRed was cloned into the SFG vector backbone between the PmlI and BamHI sites to produce the vector SFG-K9CD20-P2A-dsRed. All PCR reactions were performed using ProFlex PCR system (Applied Biosystems) and Platinum PCR super-mix (Invitrogen) kit per manufacture's recommendations. The resulting cassette K9CD20P2AdsRed was cloned in the backbone of SFG-anti-K9CD2028zLNGFR by replacing the PmlI-BamH1 cassette as shown in FIG. 14K. FIG. 14D shows an illustration of the K9CD20dsRed cassette and FIG. 14J an illustration of the SFG-vector backbone.

Example 4: Construction and Characterization of K9CD20-Targeted CAR T Cells

In this Example, the methods for generating and analyzing CAR T cells are described.

Construction of an anti-canine CD20 single-chain variable fragment (scFv)-CD3ζ-chain fusion gene (K9CAR)

Figure 17:
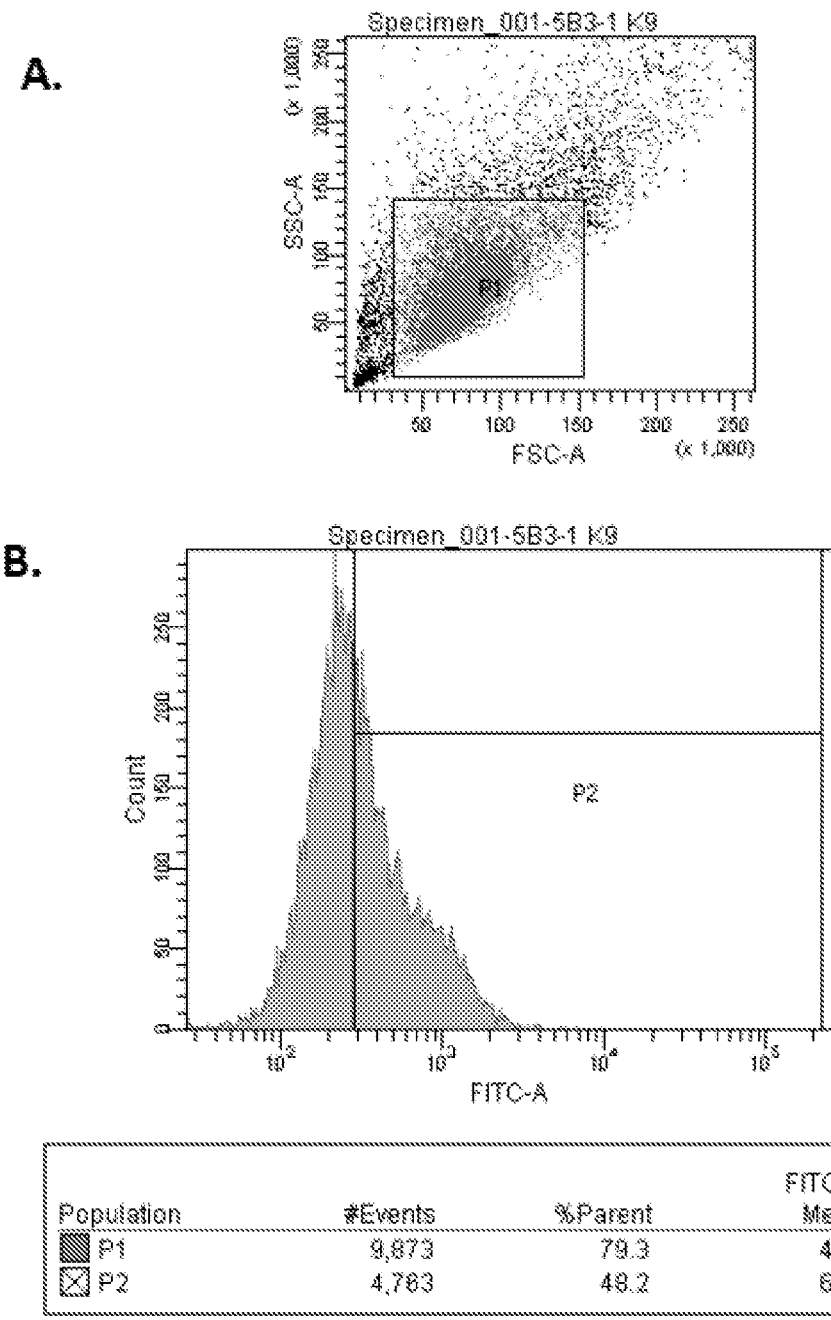
FIG. 17 illustrates the flow cytometry data for 3T3-K9CD20 cells stained with the supernatant from hybridoma clone 5B3.
Figure 18:
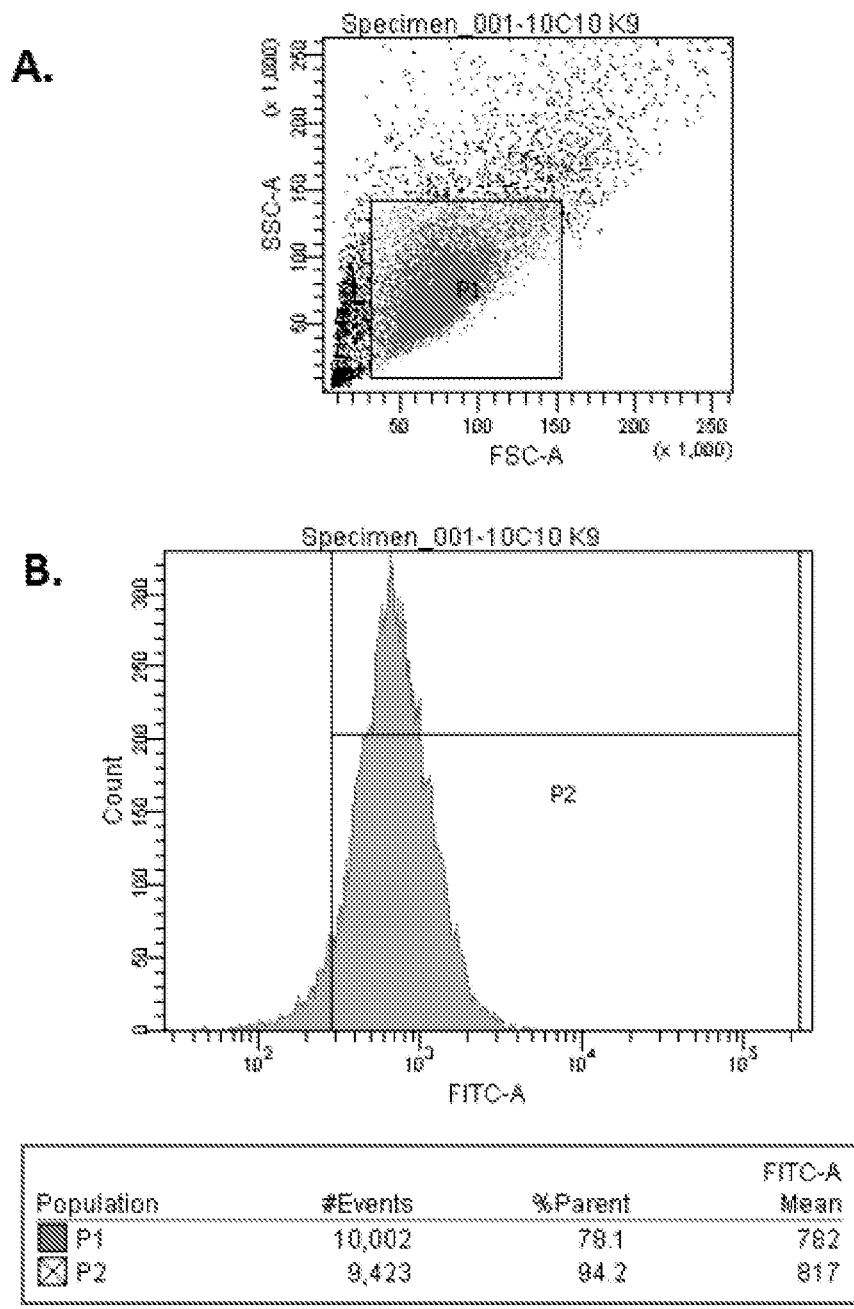
FIG. 18 illustrates the flow cytometry data for 3T3-K9CD20 cells stained with the supernatant from hybridoma clone 10C10.
Figure 19:
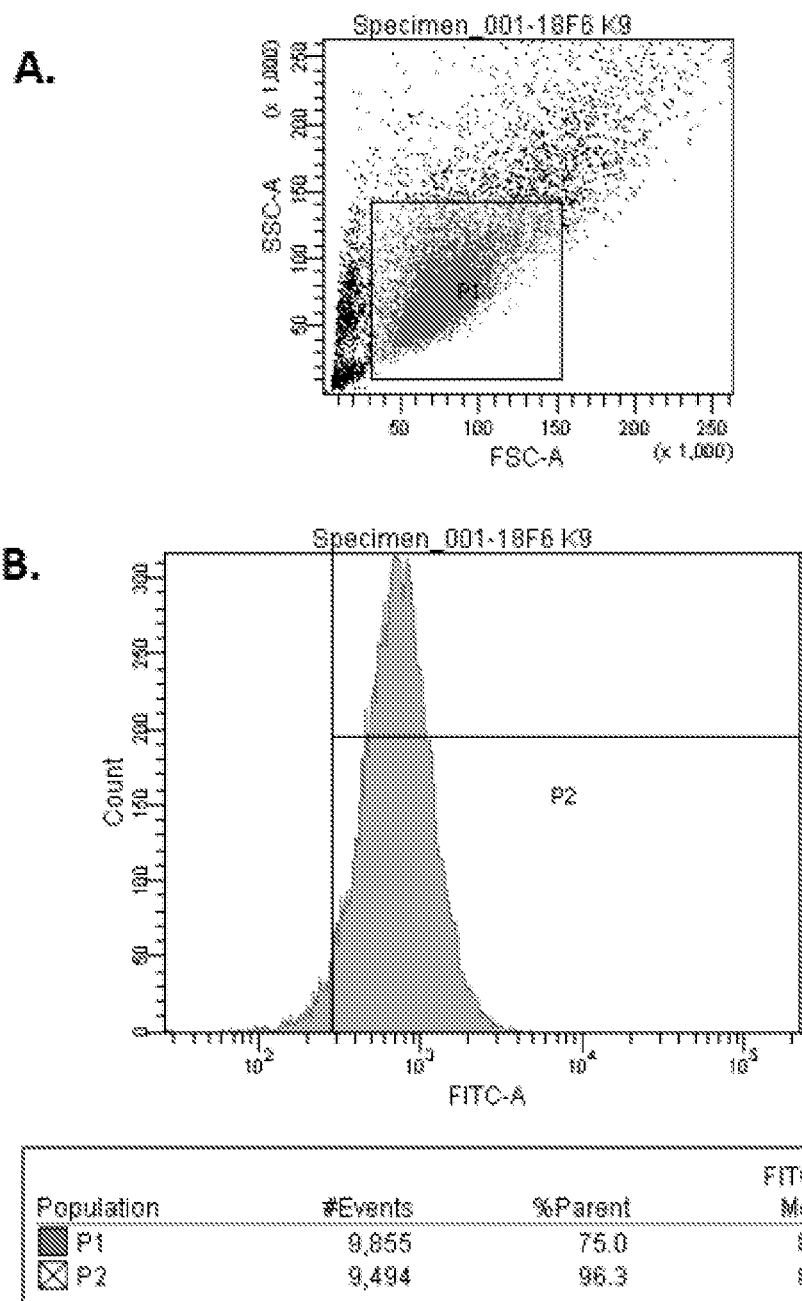
FIG. 19 illustrates the flow cytometry data for 3T3-K9CD20 cells stained with the supernatant from hybridoma clone 18F6.
Figure 20:
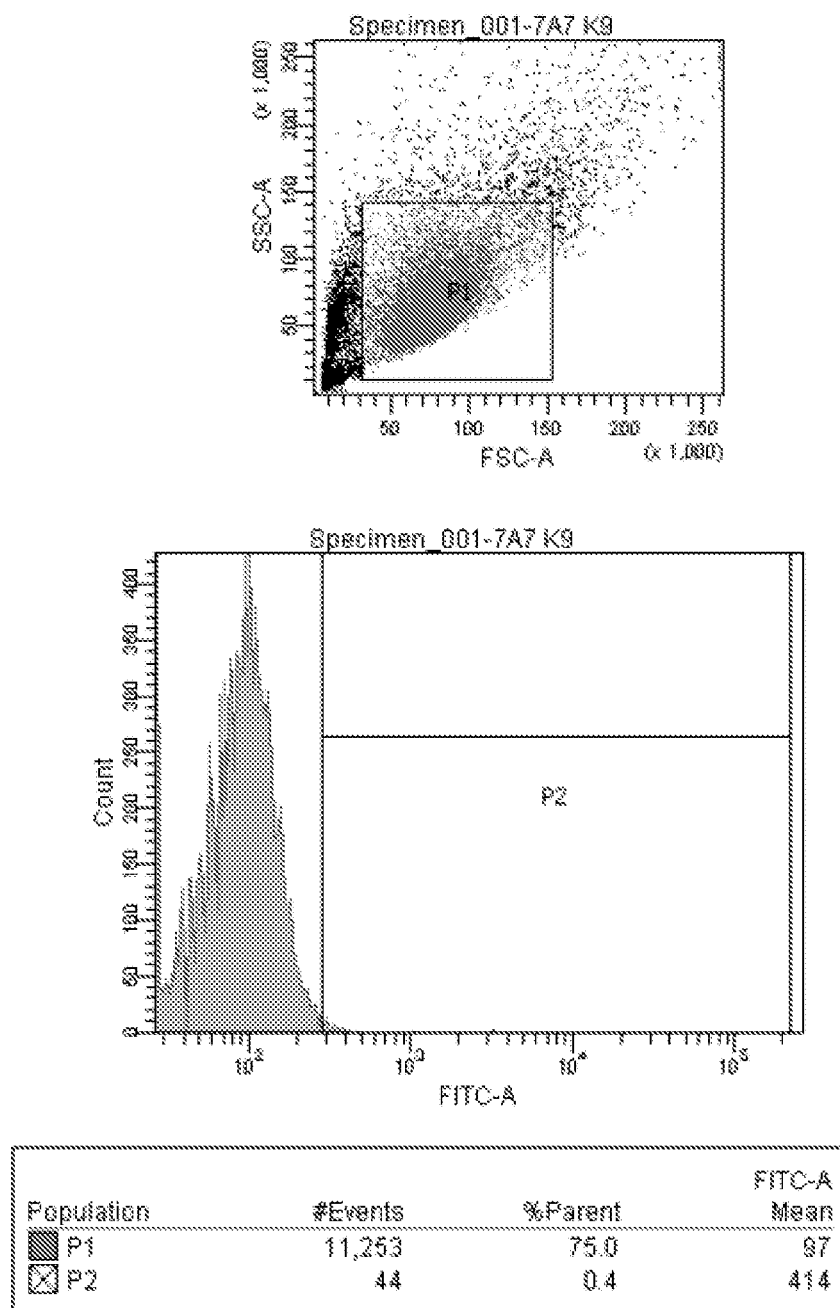
FIG. 20 illustrates the flow cytometry data for 3T3-K9CD20 cells stained with the supernatant from hybridoma clone 7A7 K9 (negative control).

To construct an anti-canine CD20-specific scFv, a rat antibody targeted to canine CD20 (K9CD20) was generated by immunization of rats with the CD20 antigen shown in FIG. 5 and as described in Examples 1 and 2. Splenocytes were isolated from the immunized rats and used to generate hybridoma cell lines as described in Example 3. Hybridomas were screened by ELISA. Hybridomas that were positive by ELISA were further screened by flow cytometry analysis using NIH3T3 cells expressing k9CD20 (3T3-K9CD20). 3T3-K9CD20 cells were stained with the hybridomas supernatant (and with secondary anti-Rat IgG FITC antibody) and analyzed by flow cytometry (FIGS. 17A-B, 18A-B, and 19A-B). As shown in FIGS. 17B, 18B, and 19B, respectively, clones 5B3, 10C10 and 18F6 were all positives for anti-K9CD20 antibody production. As a negative control, clone 7A7 K9 was confirmed negative for anti-K9CD20 antibody (FIG. 20B).

cDNA was isolated from the anti-K9CD20 antibody-producing hybridoma (18F6 clone). The nucleic acid encoding light chain (SEQ ID NO: 4) and heavy chain (SEQ ID NO: 6) variable regions of the rat anti-K9CD20 antibody were cloned from the cDNA isolated from the hybridoma 18F6 clone by 5' Rapid Amplification of cDNA Ends (5'RACE) using the following gene specific primers (GSPs):

| | Sequence | SEQ ID NO: |
|---|---|---|
| GSP(r2a)-1 | 5'-GGAAATAGCCCTTGACCAGGC | 24 |
| GSP(r2a)-2 | 5'-GAGCCAGTGGATAGACAGATG | 25 |
| GSP(r2a)-3 | 5'-GTGGATAGACAGATGGGGCTG | 26 |
| GSP(κ)-1 | 5'-AGGATGATGTCTTATGAACAA | 27 |
| GSP(κ)-2 | 5'-ATGAACAACCTCACAGGTATAGAGG | 28 |
| GSP(κ)-3 | 5'-CTCACAGGTATAGAGGTTATG | 29 |

The GSP (r2a)-1, GSP (r2a)-2, and GSP (r2a)-3 primers were used to clone the heavy chain variable region (HCVR) and the GSP (κ)-1, GSP (κ)-2, and GSP (κ)-3 primers were used to clone the light chain variable region (LCVR). FIG. 14A shows an illustration of the cloning of the light chain and heavy chain variable regions using 5'RACE.

A single-chain fragment variable (scFv) antibody (SEQ ID NO:8) (called anti-K9CD20 scFv) was generated by fusing the nucleic acids encoding light and heavy chains separated by nucleic acid encoding a Gly-Ser linker (SEQ ID NO: 10). FIG. 14B shows an illustration of the anti-K9CD20 scFv.

The anti-K9CD20 scFv was further modified by fusing the human CD8 (hCD8) leader sequence, human CD28 (hCD28) transmembrane domain, and the intracellular signaling domain of the CD3 zeta chain of the human T cell receptor (TCR) (hCD3z) to generate a chimeric antigen receptor (CAR) named K9CAR (or SFG-anti-K9CD20 CAR LNGFR). FIG. 14C shows an illustration of the K9CAR cassette.

Construction of K27

The K27 (also called K27CAR) cassette contains three canine components, the canine CD8 leader (K9CD8; SEQ ID NO:12), canine CD28 transmembrane domain (K9CD28; SEQ ID NO:14), and canine CD3z signaling domain (K9CD3z; SEQ ID NO:16), in addition to the anti-K9CD20scFv sequence. The K27 DNA fragment was generated by replacing the hCD8 leader, hCD28, and hCD3z regions in the K9CAR cassette with the corresponding canine sequences. FIG. 14E shows an illustration of the K27 cassette.

Construction of SGF-K27/41BBL

The K27/41BBL (also named K27CAR/41BBL and K36CAR) cassette contains the K27 cassette and the canine 41BBL costimulatory ligand (SEQ ID NO:18). Sequences of K9CD8 leader-anti-K9CD20ScFv-K9CD28-K9CD3zeta-P2A-K9-41BBL flanked by AgeI and XhoI sites was synthesized in pUC backbone by Blue Heron Technology (pUC-K36). The fragment between Age I and Xho I in pUC-K36 was used to replace the partial SFG backbone and 1928z sequences between AgeI and Xho I site of the SFG-1928z vector (described in Hollyman et al., *J. Immunother*, 32(2):169-80 (2009)) to produce the SFG-K36 vector. FIG. 14F shows an illustration of the K36CAR cassette.

Construction of SFG-K27

The SFG-K27 vector contains the K27 cassette. The SFG-K27 vector was produced by amplifying the K27 cassette using forward primer: 5'-GGCCGGATCCTTCAGAGTGACTACATGAA-3' (SEQ ID NO: 34) and reverse primer: 5'-TTAAGGATCCGCGGCCGCTCAGCGAGGAGGCAGGGCCTGCATG-3' (SEQ ID NO: 35) using the synthesized pUC-K36 plasmid as template. The K36 DNA fragment in SFG-K36 between BamHI sites was replaced by the K27 DNA fragment to produce the SFG-K27 vector. Orientation of K27 insert was confirmed by sequencing.

Construction of SFG-K9CD34t-K2 7 and SFG-k9CD34t-K36

The K9CD34t sequence (SEQ ID NO: 23) was synthesized and cloned in pUC by Blue Heron Technology (pUC-K9CD34t). The K9CD34t DNA fragment with an Afe I restriction site at the 5' end was amplified was amplified with primers k9CD34-F1-5'-GGCCAGCGCTGCCAC-CATGCTGGCGG (SEQ ID NO: 36) and k9CD34-R1-5'-GGGTCC AGGGTTCTCCTCCACGT (SEQ ID NO: 37) using pUC-K9CD34t plasmid as template. The K27 DNA fragment with overlapping sequence with K9-CD34 on the 5' end and a SbfI restriction site on the 3' end was amplified with primers k9CD34-F2-5'-GCTGGAGACGTGGAG-GAGAACCCTGGACC-CATGGCCTCTCGGGTGACCGCCC (SEQ ID NO: 38) and k9CD34-R2-5'-TTAACCTGCAGGAGGCGGGAA-GACCG (SEQ ID NO: 39) using SFG-K27 as template. The K9CD34t-K27 DNA fragment was amplified with primers k9CD34-F1 and k9CD34-R2 using the equal molar mixture of the K9CD34t and K27 PCR products. The K27 element in SFG-K27 was replaced by K9CD34t-K27 using the AfeI and SbfI sites to produce the SFG-K9CD34t-K27 vector construct. The K27 element in SFG-K36 was replaced by K9CD34t-K27 using the AfeI and SbfI sites to get vector SFG-k9CD34t-K36. FIGS. 14G and 14H show illustrations of the K9CD34t-K27 and K9CD34t-K36 cassettes, respectively.

Human T-Cell Cultures, Activation and Retroviral Transduction.

Blood samples were obtained from a healthy donor. Peripheral blood mononuclear cells (PBMC) were separated on Ficoll, then activated and magnet selected with CD3/CD28 dynabeads at 1:1 ratio cultured in X-VIVO 15 containing 5% human serum, 2 mmol/L L-glutamine (Life Technologies), 100 units/mL penicillin, and 100 ug/mL streptomycin (Life Technologies), 100 units/ml of IL2 (R&D Systems), HEPES buffer and pyruvate Na (day 0). After 72 hours (day 3), the human T cells were transduced by centrifugation on retronectin-coated 6-well plates with retroviral supernatant (1:1 of volume ratio) at the final density about 0.35E+6 cells/ml. On day 7, the cells were analyzed by FACS analysis for transduction efficiency. At day 10 or after, transgene expression was measured again by FACS analysis, and cytotoxicity assays were performed.

Characterization of CAR T Cells by Flow Cytometry

Flow cytometry was performed on a BD-LSRII cytometer and data analyzed with FlowJo software (Treestar). The following mAbs were used for phenotypic analysis for human T cells: phycoerythrin (PE)-labeled anti human LNGFR (CAR), APC-conjugated anti-human CD3, Pacific Blue-conjugated anti-human CD4 (BD Biosciences), and PE-Cy7-conjugated anti-human CD8. The following mAbs were used for phenotypic analysis for tumor cells NALM6: GFP for luciferase and dsRed for canine CD20.

Figure 10:
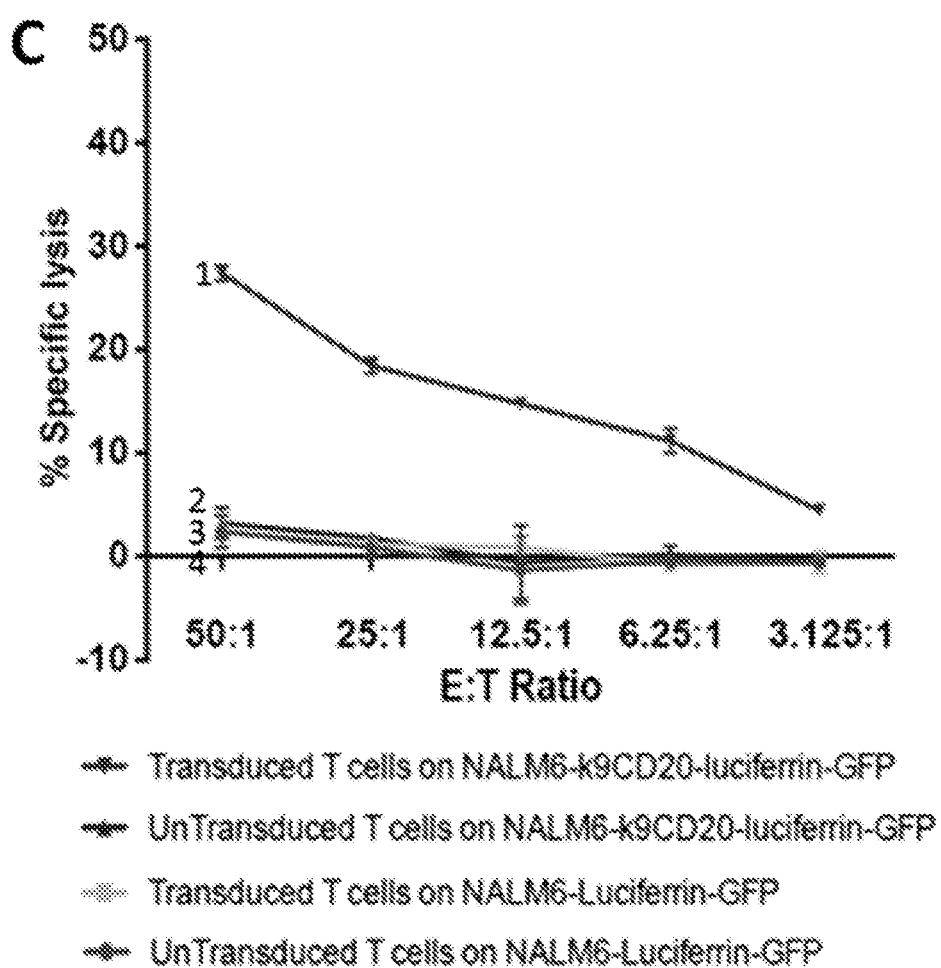
FIG. 10 illustrates that human T cells targeted to K9CD20 are functional and cytotoxic.

FIG. 10A shows the transduction efficiency of the anti-K9CD20 CAR co-expressing the L-NGFR (using the SFG-anti-K9CD20 CAR LNGFR vector as shown in FIG. 14C) in human T cells as measured by flow cytometry. The transduction efficiency was assessed by coexpression of L-NGFR. As shown in FIG. 10A, transduced human T cells expressed L-NGFR (top row), whereas non-transduced human T cells did not express L-NGFR (bottom row), and the transduction efficiency in human T cells was approximately 30%.

Cytotoxic T Lymphocyte (CTL) Assays

The cytotoxic activity of human T cells transduced with K9CD20 constructs was assessed by standard $^{51}$Cr release assays. Briefly, human T cells were transduced with the SFG-anti-K9CD20 CAR LNGFR construct, which results in expression of the CAR targeted to K9CD20 together with hu-LNGFRt, hu-CD28 signaling domain and hu-CD3z chain. Transduced T cells were assessed by LNGFR-PE for CAR expression as well as CD4:CD8 ratio on the same performing CTL. NALM-6 or EL4 tumor cells were labeled with $^{51}$Cr for 1 hour at 37° C., washed with RPMI medium supplemented with 10% FCS, and resuspended in the same medium at a concentration of $1 \times 10^5$ tumor cells/mL. Transduced T cells and non-transduced T cells were added to tumor cells at varying effector to target cell ratios in 96-well tissue culture plates in a final volume of 200 uL, and incubated for 4 hours at 37° C. Thereafter, 40 uL of supernatant from each well was analyzed using Lumaplate-96 microplates (Packard Bioscience) by a Top Count NXT microplate scintillation counter (Packard Bioscience). Effector cell number in all CTL assays was calculated based on the total number of T cells.

FIG. 10B shows the results for the Cr51 cytotoxic release assay in EL4 tumor cells. Line 1 refers to transduced T cells applied to EL4 tumor cells expressing K9CD20; Line 2 refers to non-transduced T cells applied to EL4 tumor cells expressing K9CD20; Line 3 refers to transduced T cells applied to EL4 tumor cells that do not express K9CD20; and Line 4 refers to non-transduced T cells applied to EL4 tumor cells that do not express K9CD20As shown in FIG. 10B, transduced T cells specifically killed EL4 tumor cells expressing K9CD20 (see line number 1 in FIG. 10B) but not EL4 wild-type tumor cells (see Line 3 in FIG. 10B). In addition, non-transduced T cells did not kill EL4 tumor cells (see Lines 2 and 4 in FIG. 10B).

FIG. 10C shows the results for the Cr51 cytotoxic release assay in NALM6 tumor cells. Line 1 refers to transduced T cells applied to NALM6 tumor cells expressing K9CD20; Line 2 refers to non-transduced T cells applied to NALM6 tumor cells expressing K9CD20; Line 3 refers to transduced T cells applied to NALM6 tumor cells that do not express K9CD20; and Line 4 refers to non-transduced T cells applied to NALM6 tumor cells that do not express K9CD20 As shown in FIG. 10C, transduced T cells specifically killed NALM6 tumor cells expressing K9CD20 (see line number 1 in FIG. 10C) but not NALM6 tumor cells expressing Luciferin control (see Line 3 in FIG. 10C). In addition, non-transduced T cells did not kill any tumor cells (see Lines 2 and 4 in FIG. 10C).

In Vivo NOD.Cg-Prkdc$^{scid}$ Il2rg$^{tm1Wjl}$/SzJ (NSG) Mouse Tumor Models 6- to 8-week-old NSG mice were inoculated with 0.5×10$^6$NALM-6 tumor cells that expressed more than 95% luciferase-GFP and canine CD20-dsRed by tail vein injection each mouse (day 0). Mice were treated with 5×10$^6$ of CAR+ T cells (transduced group) and equal amount UT cells (untransduced group) by tail vein injection at day 4.

Figure 11:
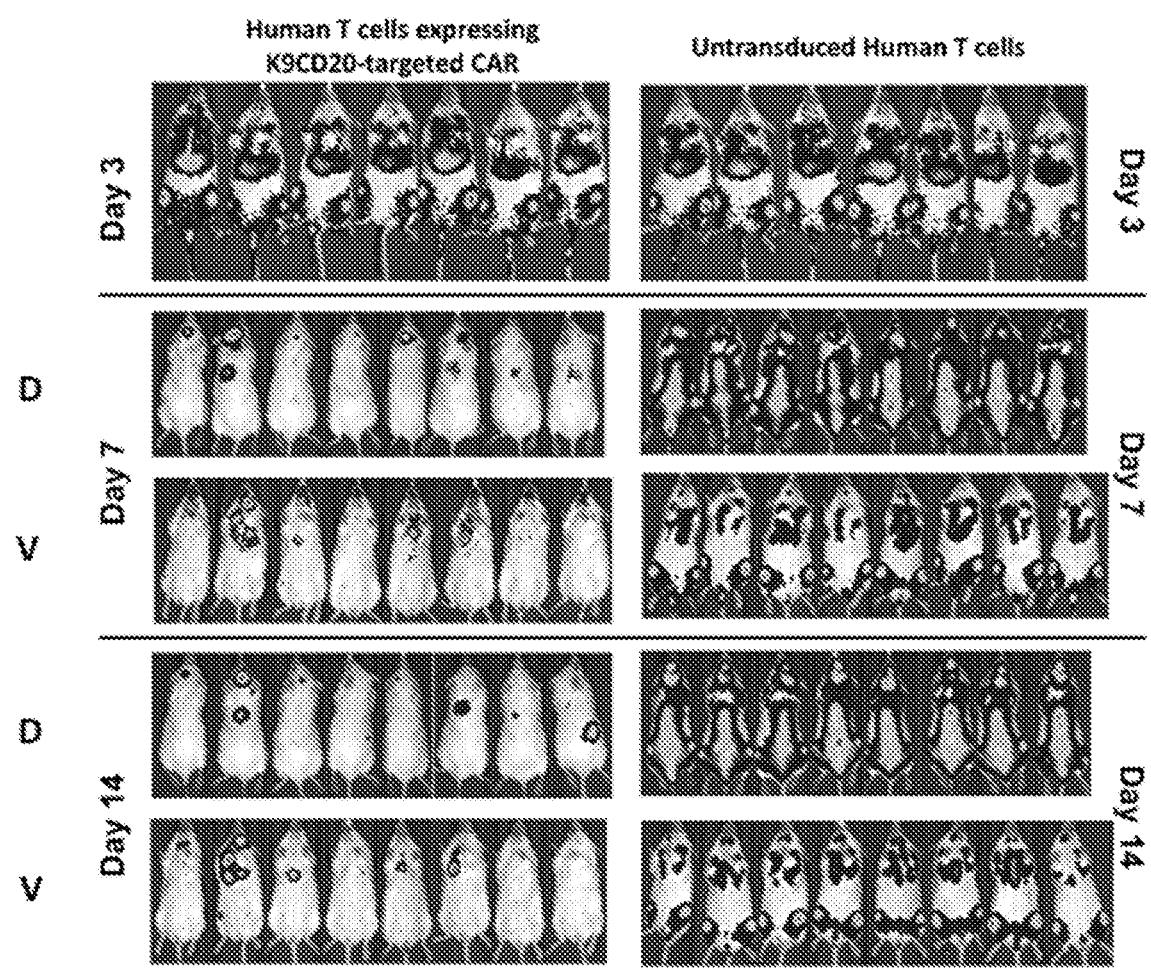
FIG. 11 illustrates human T cells expressing K9CD20-targeted CAR are functional in vivo.

FIG. 11 shows that human T cells expressing K9CD20-targeted CAR are functional in vivo in a mouse model of lymphoma as the NALM-6 tumor cells expressing luciferase are eradicated over time in mice infused with K9CD20-CAR and expand in mice treated with untransduced T cells (as shown by luminescence upon infusion with luciferin). V: ventral view; D: Dorsal view.

Canine T-Cell Cultures, Activation and Retroviral Transduction

Blood samples were obtained from healthy canine donor. Peripheral blood mononuclear cells (PBMC) were separated on Ficoll-paque™ plus (GE healthcare). Thawed or freshly isolated canine PBMCs were activated with PHA (Fisher Scientific) in RPMI (Corning) containing 15% FBS, 2 mmol/L L-glutamine (Life Technologies), 100 units/mL penicillin, 100 ug/mL streptomycin (Life Technologies), and 50 to 200 units/ml of IL2 (R&D Systems) for 48 hours. Activated canine T cells were transduced in RetroNectin-coated 6-well plates with retroviral vector at the final density of approximately 0.5×10$^6$ cells/mL by spinoculation at 1200 rpm for 1 hour. Transduction efficiency is evaluated 7 days post transduction by qPCR analysis.

Cytotoxic Lymphocyte (CTL) Assay Using Canine T Cells

Cytotoxic activity of transduced canine T cells was determined by $^{51}$Cr release assays as previously described (Yuan et al., *J Immunol* 176 (4), 2006). Briefly, NALM-6 tumor cells were labeled with $^{51}$Cr for 1 hour at 37° C., washed with RPMI medium supplemented with 10% FCS, and resuspended in the same medium at a concentration of 1×10$^5$ tumor cells/mL. Transduced canine T cells or non-transduced canine T cells were added to pre-labeled tumor cells at varying effector to target cell ratios in 96-well tissue culture plates in a final volume of 200 uL and incubated for 4 hours at 37° C. 40 uL of supernatant from each well was subsequently analyzed using Lumaplate-96 microplates (Packard Bioscience) by a Top Count NXT microplate scintillation counter (Packard Bioscience). CAR expression as well as CD4:CD8 ratio on the same performing CTL were assessed by specific antibodies using FACS analysis. Effector cell numbers in CTL assays were calculated based on the total number of T cells.

Figure 12:
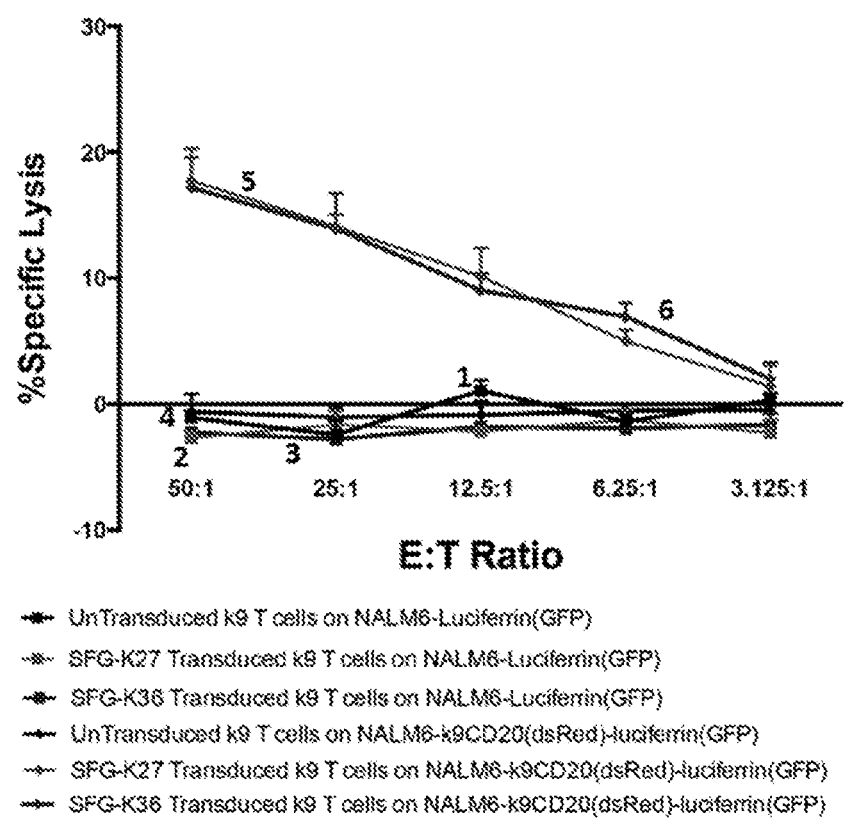
FIG. 12 shows the results of a Cr51 cytotoxic release assay in NALM6 or NALM6-K9CD20 tumor cells.

FIG. 12 shows the results for the Cr51 cytotoxic release assay in NALM6 tumor cells treated with canine T cells. Line 1 refers to non-transduced canine T cells applied to NALM6 tumor cells expressing luciferin; Line 2 refers to canine T cells transduced with the SFG-K27 CAR construct applied to NALM6 tumor cells expressing luciferin; Line 3 refers to canine T cells transduced with the SFG-K36 CAR construct applied to NALM6 tumor cells expressing luciferin; Line 4 refers to non-transduced canine T cells applied to NALM6 tumor cells expressing K9CD20; Line 5 refers to canine T cells transduced with the SFG-K27 CAR construct applied to NALM6 tumor cells expressing K9CD20; and Line 6 refers to canine T cells transduced with the SFG-K36 CAR construct applied to NALM6 tumor cells expressing K9CD20. As shown in FIG. 12, transduced canine T cells specifically killed NALM6 tumor cells expressing K9CD20 antigen (NALM6-K9CD20) but not control NALM6 tumor cells expressing luciferin (NALM6-Luciferin). Canine T cells transduced with SFG-K27 CAR express the K27 CAR comprising the anti-K9CD20scFv, K9-CD28 signaling domain and K9-CD3z chain. Canine T cells transduced with SFG-K36 CAR co-express the K27 CAR and 41BBL.

FIG. 13 shows the results for the Cr51 cytotoxic release assay in NALM6 tumor cells treated with canine T cells. Line 1 refers to non-transduced canine T cells applied to NALM6 tumor cells expressing luciferin; Line 2 refers to canine T cells transduced with the SFG-K27 CAR construct applied to NALM6 tumor cells expressing luciferin; Line 3 refers to canine T cells transduced with the SFG-K36 CAR construct applied to NALM6 tumor cells expressing luciferin; Line 4 refers to canine T cells transduced with the SFG-k9CD34t-K27 CAR construct applied to NALM6 tumor cells expressing luciferin; Line 5 refers to canine T cells transduced with the SFG-k9CD34t-K36 CAR construct applied to NALM6 tumor cells expressing luciferin; Line 6 refers to non-transduced canine T cells applied to NALM6 tumor cells expressing K9CD20; Line 7 refers to canine T cells transduced with the SFG-K27 CAR construct applied to NALM6 tumor cells expressing K9CD20; Line 8 refers to canine T cells transduced with the SFG-K36 CAR construct applied to NALM6 tumor cells expressing K9CD20; Line 9 refers to canine T cells transduced with the SFG-k9CD34t-K27 CAR construct applied to NALM6 tumor cells expressing K9CD20; and Line 10 refers to canine T cells transduced with the SFG-k9CD34t-K36 CAR construct applied to NALM6 tumor cells expressing K9CD20. As shown in FIG. 13, transduced canine T cells specifically killed NALM6 tumor cells expressing K9CD20 antigen (NALM6-K9CD20) but not control NALM6 tumor cells expressing luciferin (NALM6-Luciferin). Canine T cells transduced with SFG-K27 CAR express the K27 CAR comprising the anti-K9CD20scFv, K9-CD28 signaling domain and K9-CD3z chain. Canine T cells transduced with SFG-K36 CAR co-express the K27 CAR and 41BBL. Canine T cells transduced with SFG-K9CD34t-K27 express the K27CAR and the truncated K9CD34t. Canine T cells transduced with SFG-K9CD34t-K36 express the K36CAR and the truncated K9CD34t.

Example 5: Evaluation of Optimal Dose and Combination of CAR T Cell Therapy

In this Example, the efficacy and safety profile of CAR T cell therapy in canines are evaluated. Dogs are treated with a CAR T cell therapy comprising K27CAR-4-1BBL T cells and/or K27CAR-PD1-DNR T cells. In a CAR T cell therapy, dogs are infused with CAR T cells. The efficacy of CAR T cell therapy is measured by B cell lymphodepletion.

In addition, dogs may be treated with therapeutic regimens comprising K27CAR-4-1BBL T cells and/or K27CAR-PD1-DNR T cells in combination with cyclophosphamide (Cy) and/or total body irradiation (TBI) (e.g., low dose TBI, for example 0.01 Gy to 1.0 Gy). In the CAR T combination therapy, dogs may be treated with Cy at least 24 hours prior to the first T cell infusion. The CAR T combination therapy may be performed in a myeloablative setting. Alternatively, the CAR T combination therapy is performed in a nonmyeloablative setting.

Methods for collecting T cells, transducing T cells, infusing CAR T cells, and evaluating the efficacy and toxicity of CAR T cell therapy are described in this Example.

T Cell Collection

Prior to the T cell infusion, autologous T cells are collected from a leukapheresis product. Leukapheresis is performed for example on a COBE Spectra machine. A single leukapheresis cell product should be enough for expansion and generation of autologous CAR T cells. Additionally, lymph node aspirates are collected to determine baseline disease. Additionally, lymph node aspirates are collected without anesthesia using a 21- or 22-gauge needle.

T Cells Purification, Transduction and Ex Vivo Characterization

The collected T cells are separated on a Ficoll gradient, expanded, and activated ex vivo. Briefly, canine PBMCs are stimulated with PHA and transduced with K27/PD1-DNR or K27/41BBL CAR vectors pseudotyped with RD114 envelope using 50 to 200 U/ml of human IL-2 (hIL-2). The leukapheresis product is characterized by flow cytometry analysis of CD3+, CD4+, CD8+, CCR7+, CD62L+, CD28+, CD27+ cells to identify T cells. The expression of CD21 together with CD20 are evaluated to identify B cells. CD20 expression is assessed with an 18F6 rat antibody from which the anti-K9CD20 ScFv was derived and which co-stains the majority of the CD21+ normal B cells in canine peripheral blood by FACS. The phenotype of transduced CART cells and remaining B cells, if any, is subsequently characterized by flow cytometry with the same antibodies in addition to CD34 (which is used as a surrogate for transduction efficiency). Functionality of CAR T cells is assessed in a $^{51}$Cr release assay using K9CD20-expressing target cells. Cytokine production in end-of-production (EOP) CAR T cells is evaluated upon restimulation with K9CD20 AAPCs (NIH3T3 fibroblasts expressing K9CD20) using the Luminex technology (CCYTOMAG-90K Milliplex EMD Millipore). CAR T cells can be infused either fresh or post-thaw.

CAR T Cell Infusion

Following ex vivo transduction, expansion and characterization, the CAR T cell product is infused intravenously in dogs. Depending on CAR T cell persistence after the first infusion, each dog could receive a second dose 2 to 4 weeks later as indicated in Table 7. For K27/PD1-DNR CAR T cell therapy (also called 28z/PD1-DNR), the first infusion consists of $10^6$ cells/kg and the second infusion consists of $3\times10^6$ cells/kg. For K27/41BBL CART cell therapy (also called 28z/41BBL), the first infusion consists of $10^5$ cells/kg and the second infusion consists of $3\times10^5$ cells/kg. The same doses of both CAR-T cells are infused in the CAR T cell combination therapy (also called Combo 28z/PD1-DNR 28z/41BBL) (Table 7 and FIG. 15).

TABLE 7

| | Dose escalation/de-escalation | | | |
|---|---|---|---|---|
| Dose Level | T cell Dose 28z/PD1-DNR | T cell Dose 28z/41BBL | Combo | Number of Dogs |
| −1 | $10^6$ CAR T cells/kg | $10^5$ CAR T cells/kg | 28z/PD1-DNR + 28z/41BBL | 3 |
| 1 | $3 \times 10^6$ CAR T cells/kg | $3 \times 10^5$ CAR T cells/kg | 28z/PD1-DNR + 28z/41BBL | 3 |
| 2 | $10^7$ CAR T cells/kg | $10^6$ CAR T cells/kg | 28z/PD1-DNR + 28z/41BBL | 3 |

Engraftment Monitoring

The engraftment of the infused CAR T cells is monitored in the peripheral blood and lymph nodes. Blood draws are performed on days 1, 3, and 7 following T cell infusion, then once a week until CAR T cells are not detected in two consecutive blood draws. Lymph node aspirates are also collected 1, 2, and 4 weeks after the infusion to monitor CAR T cell trafficking and persistence. The CAR T constructs are tagged with the truncated canine CD34 (tCD34), allowing for CAR T cells tracking in vivo. Flow cytometry analyses are performed on both peripheral blood and lymph nodes aspirates using canine CD45, CD3, CD4, CD8, CD34, CD62L, CD27, CCR7, and CD28 staining. Alternatively, if an insufficient number of cells is obtained, especially in the lymph nodes, RNA is extracted to enable the detection of CAR T cells by quantitative PCR analysis (utilizing PCR primers specific for the junction with 41BBL or PD1-DNR). If T cell numbers allow, retrieved CAR T cells are analyzed by RNA Seq (see Example 7). A leukapheresis is performed at day 28 to provide additional material for complete functional (cytotoxicity, cytokine secretion), flow cytometry (differentiation and exhaustion phenotype), and genomic (vector copy number, RNAseq) studies (see Example 7).

Determination of Maximum Tolerated Doses and Toxicities

Toxicities are closely monitored. To this end, lymphodepletion and, more specifically, the kinetics of B cell aplasia as well as recovery are evaluated by flow cytometry detection of CD21+ cells at the same time points as indicated (FIG. 15) in both peripheral blood and popliteal lymph nodes. B cell aplasia may be indirectly monitored by serum immunoglobulin quantified by serum protein electrophoresis. Additionally, severe CRS has been characterized in humans by the release of a variety of cytokines such as interleukin-6 (IL-6), interferon-γ, and IL-10 in the serum of patients experiencing fever, tachycardia, and hypotension symptoms. Such increase in cytokines release has also been associated with B cell lymphoma in dogs and is quantified in the serum at each blood draw using Luminex technology (EMD Millipore Milliplex) with a special emphasis on IL-6, interferon-γ and TNFα and correlated with toxicities and adverse events. To resolve AEs, steroids such as dexamethasone may be injected to curtail the expansion of CAR T cells. In the event of neurotoxicity following T cell infusion, CSF is collected and analyzed for presence of CAR T cells and cytokines. CRP levels are measured daily until the CAR T cell expansion riches a plateau using the LifeAssays® Canine CRP Test to determine if it may serve as a predictor of severe cytokine release syndrome (sCRS). Serum immunoglobulin and serum protein electrophoresis.

Statistical Considerations

Two CAR T cell constructs (K27/41BBL and K27/PD1-DNR) may be tested, each individually and upon co-infusion of both subsets of CAR T cells. The primary objective for each group is to identify a dose that is safe and efficacious. Efficacy is assessed by the appearance of B-cell aplasia and safety is defined as lack of sCRS. Any occurrence of sCRS results in de-escalation of the dose for one or the combined two CAR T cell constructs. If the occurrence of B-cell aplasia is not frequent enough, then the dose of CAR T cells is escalated to the next higher dose level. Only two dose levels are considered unless sCRS occurs at the starting dose level, in which case the dose is de-escalated.

Conditions to be considered for identifying whether a dose has sufficient efficacy and an acceptable toxicity profile include the frequency of occurrence of sCRS and B cell aplasia.

Example 6: Determining the Efficacy of Lymphodepletion and CAR Design in Companion Dogs with CD20+ B Cell Lymphoma In this Example, the functional persistence, safety, and efficacy of autologous CAR T cells expressing either K27/PD1-DNR or K27/41BBL and/or both subsets in canine companion patients with B cell lymphoma (n=9 to 15) using the optimal dosing identified in Example 5 are evaluated. Correlative studies focus on B cell aplasia and recovery, tumor eradication, CAR T cell persistence, functionality, and exhaustion, and the impact of CAR T cells on endogenous lymphoid and myeloid cells (see Example 7).

Dog Studies and Chemotherapy

Similar to the experimental animals in Example 5, companion dogs are treated with Cy prior to CAR T cell infusion. As possible, blood draws and lymph nodes aspirates are performed on the same schedule as described in Example 5 and FIG. 15, in order to monitor CAR T cell persistence.

Enrollment criteria is similar to human patients treated with CD19 targeted CAR T cells: Patient dogs must have B cell lymphoma that has relapsed after a response to at least one prior therapy regimen or is refractory to prior therapy. Patient dogs come to the laboratory for apheresis and then return to their owner or referring veterinarian physicians. After CAR T cells have been generated, dogs return to the laboratory and receive Cy as conditioning as discussed in Example 5. At least 24 hours after Cy, the patient dogs receive the CAR T cells with appropriate premedication. Animals return to the veterinary clinic for close observation and monitoring for cytokine release syndrome (CRS). Disease is assessed by analysis of CD79a, IgM, and/or CD21 expression on lymph node aspirates when possible. The expression of CD20 is also evaluated using the antibody 18F6, from which the anti-K9CD20 ScFv was derived and which co-stains most of the CD21+ normal B cells in canine peripheral blood.

FIG. 24 shows flow cytometry data demonstrating detection canine CD20 with antibody 18F6. The figure shows Canine PBMCs cells stained with CD21 (PE/FL2-H) alone or in combination with antibody 18F6.

CAR T Cells Generation and Infusion

Autologous T lymphocytes are obtained through Ficoll density gradient, activated, and expanded ex vivo as described in Example 4. Following the same experimental procedure as described in Examples 4 and 5, the cells are transduced with CAR construct(s) described in Example 5 with the most efficient and least toxic dose identified in Example 5. The leukapheresis and generated CAR T cells are characterized by flow cytometry analysis with the same antibody panels as described in Example 5. A $^{51}$chromium release assay and cytokine quantification may be performed as described in Example 5.

Engraftment Monitoring

CAR T cell persistence is analyzed on peripheral blood and lymph node samples collected as described in Example 5. T cell infusion engraftment is monitored at each blood draw at days 1, 3, and 7 following the T cell infusion, then once a week until CAR T cells are not detected in two consecutive blood draws. Additionally, CAR T cells trafficking to and persistence in the lymph nodes are evaluated at 1, 2, and 4 weeks post-infusion. Infused CAR T cells can be tracked in vivo by staining of the truncated canine CD34 (and corroborated by qPCR for vector sequences). The phenotype of T cells is monitored using CD3, CD4, CD8, CD34, CCR7, CD62L, CD28, CD27 staining. If T cell numbers allow, retrieved CART cells are analyzed by RNA Seq. A leukapheresis is performed at day 28 to provide additional material for complete functional (cytotoxicity, cytokine secretion), flow cytometric (differentiation and exhaustion phenotype), and genomic (vector copy number, RNAseq) studies.

Toxicities

Figure 15:
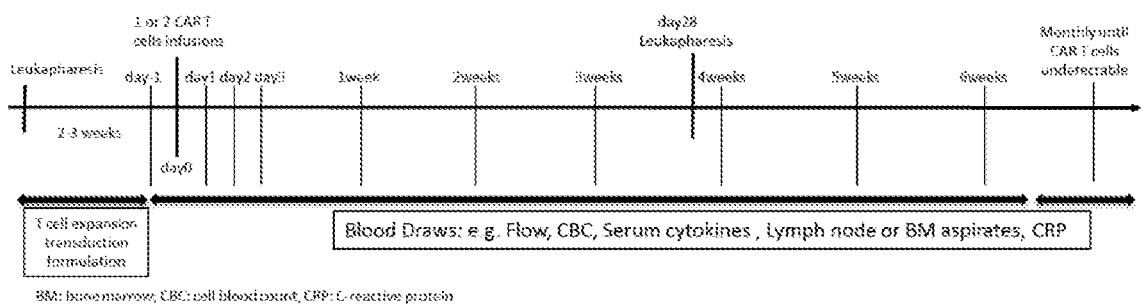
FIG. 15 illustrates a canine treatment timeline
Figure 16:
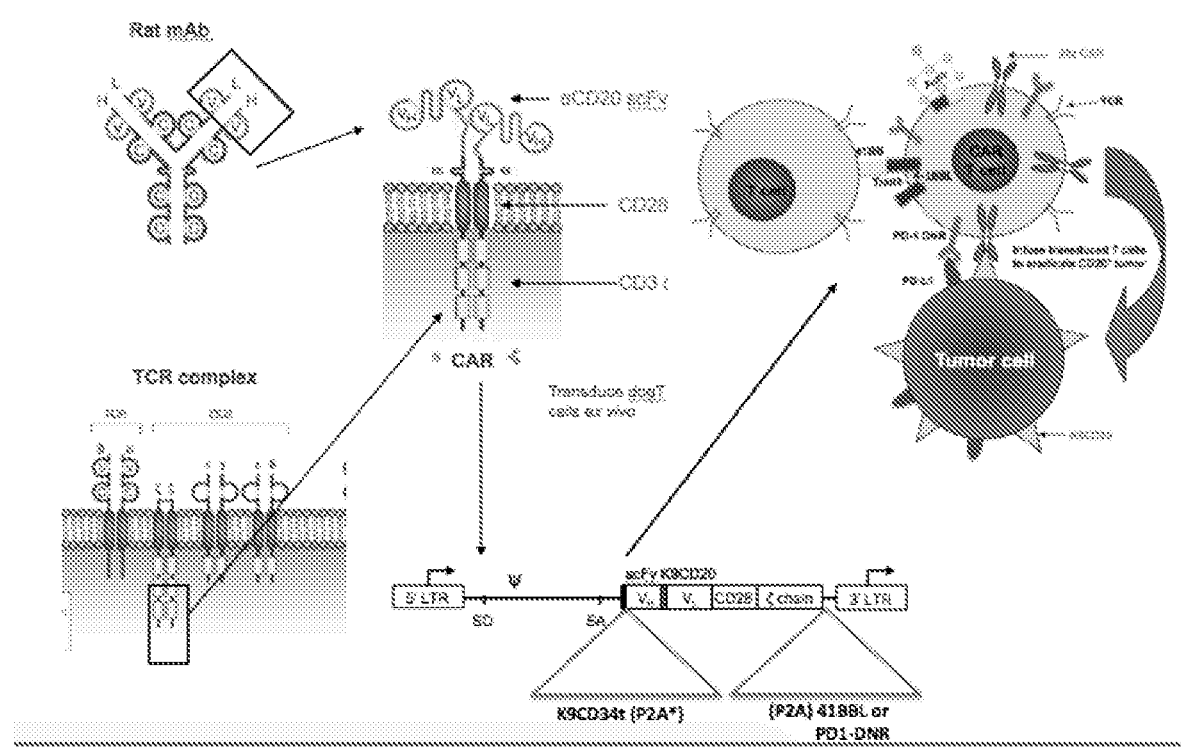
FIG. 16 illustrates a schematic of the use of K9CD20-targeted CAR canine T cells for the treatment of B cell malignancies. CAR function can be potentiated by co-expression of PD1-DNR or 41BBL. 41BBL can interact in cis upon activation and upregulation of 41BB on CART cells (auto: autocostimulation) and in trans by interacting with 41BB on other CAR or endogenous T cells (trans: transcostimulation). PD1-DNR interacts with PDL-1 expressed on tumor cells and offsets the inhibition of CAR T cell function.

The kinetics of B cell aplasia versus recovery is monitored at the time points indicated in FIG. 15 by flow cytometry analysis of CD20 (with 18F6 antibody), CD21+ cells in the peripheral blood, plus lymph nodes aspirates at weeks 1, 2, and 4 post-infusion. Serum immunoglobulin, serum protein electrophoresis, cytokines in the serum for each blood draw of each patient, CRP levels are measured as described in Example 5 at the same time points. To resolve AEs, steroids such as dexamethasone may be injected to curtail the expansion of CAR T cells. In the event of neurotoxicity, CSF is analyzed for presence of CAR T cells and cytokines.

Tumor Eradication

Tumor eradication is evaluated based on the disappearance of clinical (physical evaluation) and cellular evidence of leukemic cells (flow cytometry with CD79a, IgM CD21, and/or 18F6 antibodies), restoration of normal hematopoiesis, as well as serum concentrations of cytokines.

Example 7: Comprehensive Correlative Studies to Evaluate Safety and Efficacy of CD20 CAR T Cell Therapy in Companion Dogs The main focus of this Example is to determine the action of either 28z/PD-1 DNR or 28z/4-1BBL CAR T cells alone or in combination on endogenous T cells and on the tumor microenvironment. Specifically, this Example focuses on a) the functional persistence of infused CAR T cells, b) cytokine responses in vitro in EOP CAR T cells, in vivo in peripheral blood and in CRS, and on c) the trans-costimulatory effect of constitutive 4-1BBL expression in CAR T cells and CAR T cell cytokine secretion is assessed in tumor specimens (bone marrow or lymph node). In addition to enumerating tumor cells, T cells (CAR T cells, non-CAR T cells, and Tregs) and myeloid cells, the level of expression of for example PD-L1 and HLA class I on tumor cells and surrounding cells including Tregs and myeloid cells are examined. Peripheral blood and serum are collected at 1, 3, 7 days and weekly thereafter for analysis. Lymph node aspirates are collected pretreatment and at 1, 2 and 4 weeks post infusion as possible. Apheresis is collected 28 days after CAR T cell infusion.

Flow Cytometric Studies and qPCR Assay

CAR, B, T and myeloid lineage cells' phenotypes are examined as described in Examples 5 and 6. T cell peak expansion (PK) and persistence are measured by FACS analysis and corroborated by qPCR measuring the average vector copy number (VCN) in tissues samples. The qPCR assay is designed to distinguish K27/PD1-DNR and K27/41BBL and is performed on cells from CSF. If T cell numbers allow, RNA is performed at these time points and at day 28 (apheresis).

Cytokine Studies and CSF Analyses

Multiple cytokines and chemokines are monitored using (CCYTOMAG-90K Milliplex EMD Millipore) and read on Luminex. Cytokines are monitored in canine serum, plasma pre- and post-infusion, in CSF and in EOP CAR T cells prior to infusion and upon restimulation in vitro. If possible (especially in day 28 apheresis), CAR T cells are selected based on the expression of truncated CD34 molecule to conduct these assays. Post CAR T cell infusion, pro-inflammatory cytokines, such as IL-6, are monitored. The cytokine profiles between K27CAR/PD1-DNR and K27CAR/41BBL-treated dogs are compared.

CRP Monitoring

CRP levels are measured daily until the CAR T cell expansion reaches a plateau using the LifeAssays® Canine CRP Test to determine if it may serve as a predictor of severe CRS.

RNAseq/Gene Expression Profiling

RNA seq technology is used to characterize the tumor, the tumor environment and the host immunologic responses to CAR T cells. RNAseq is performed. Lymph nodes aspirates are collected before treatment and 1, 2 and 4 weeks post infusion, 4 weeks being the time point by which most responses are observed in clinical trials using human 1928z CAR T cells. RNA extracted from isolated cells are submitted to whole genome sequencing. Gene expression profile is analyzed using the CanFam3.1 Assembly of the dog genome that encompasses ~15,000 annotated gene transcripts is regularly updated. The RNAseq assay is used to inform on the detection of CAR T cells in the tumor. The analysis focuses on identifying genes in which transcription is altered after infusion of CAR T cells. Gene expression profile results are compared between responders and non-responders and used to identify factors in the tumor, the tumor environment, or infiltrating immune cells that impact clinical outcome. A similar analysis of peripheral blood leucocytes is undertaken at the same time points to study immune responses more broadly.

TCRseq

To elucidate the role of the native T cell response in establishing and maintaining clinically sustainable anti-tumor immunity under CAR therapy, high-throughput T cell receptor sequencing (TCRseq) is used to study the canine TCR repertoire throughout treatment with K27CAR/PD1-DNR and K27CAR/41BBL CAR T cells. TCRseq allows bulk profiling of the complementarity-determining region 3 (CDR3) sequences that are generated uniquely in each T cell and clonally expanded in the population upon antigen stimulation. The C-domains of both the T cell receptor alpha (TRA) and T cell receptor beta (TRB) loci are well mapped, making both chains accessible to TCRseq library generation using universal 5' amplification methods. Reagents are used to amplify and sequence the canine TRA/TRB (and eventually TRG/TRD) loci.

TCRseq is used to determine the extent of epitope spreading during response to CAR T cell therapy, and whether the additional trans-stimulatory effects of PD1-DNR and 4-1BBL facilitate epitope spreading to provide a therapeutic benefit. TCRseq of the canine repertoire, combined with the computational and analytical resources, is used to determine the timing, strength, and breadth of the induction of antigen-driven clonal/oligoclonal expansion of native canine T cells in the presence of CAR-T activity, and evaluate the impact of 4-1BBL stimulation on this process.

---

What is claimed is:

1. An isolated antibody or an antigen binding portion thereof that specifically binds to a canine CD20 cyclic peptide having the sequence of SEQ ID NO: 20, wherein the cysteine at position 7 of SEQ ID NO: 20 forms a disulfide bond with the cysteine at position 23 of SEQ ID NO: 20, wherein the antibody or the antigen binding portion comprises a heavy chain variable domain (VH) complementarity determining region (CDR)1 of SEQ ID NO: 40, a VH CDR2 of SEQ ID NO: 42, a VH CDR3 consisting of a threonine (T) residue, and a light chain variable domain (VL) CDR1 of SEQ ID NO: 46, a VL CDR2 of SEQ ID NO: 48, and a VL CDR3 of SEQ ID NO: 50.

2. The isolated antibody or antigen binding portion of claim 1, comprising a heavy chain variable domain (VH) comprising SEQ ID NO: 4 and/or a light chain variable domain (VL) comprising SEQ ID NO: 6.

3. The isolated antibody or antigen binding portion of claim 1, wherein the isolated antibody or antigen binding portion is a full length antibody, a Fab fragment, a F(ab')2 fragment, or a single chain variable fragment (scFV).

4. The isolated antibody or antigen binding portion of claim 1, wherein the isolated antibody or antigen binding portion comprises SEQ ID NO: 8.

5. A fusion protein comprising the isolated antibody or antigen binding portion of claim 1, wherein the fusion protein comprises a scFv-Fc fusion protein, immunoconjugate, or bispecific antibody, optionally wherein the fusion protein comprises a second component selected from the group consisting of a cytotoxin, a detectable label, a radioisotope, a therapeutic agent, a liposome, a nanoparticle, a binding protein, or an antibody.

6. A nucleic acid encoding the isolated antibody or antigen binding portion of claim 1.

7. An expression vector comprising the nucleic acid of claim 6.

8. A cell comprising the nucleic acid of claim 6 or a vector comprising said nucleic acid.

9. A chimeric antigen receptor comprising (i) an antigen binding portion comprising the isolated antibody or antigen binding portion of claim 1; (ii) a transmembrane portion; and (iii) a cytoplasmic signaling portion.

10. A cell expressing a chimeric antigen receptor of claim 9, wherein the cell is a T cell or natural killer (NK) cell.

11. A pharmaceutical composition comprising the isolated antibody or antigen binding portion of claim 1; and a physiologically acceptable diluent, excipient or carrier.

12. A method of treating a condition mediated by B-cells in a subject in need thereof comprising administering to the subject an effective amount of the cell of claim 10, wherein the condition mediated by B-cells is a B cell lymphoma or an immune mediated disease.

13. The method of claim 12, wherein the immune mediated disease is an autoimmune disease.

14. A method for detecting a CD20 protein or an extracellular domain of a CD20 protein in a biological sample, comprising contacting a biological sample with the antibody or antigen binding portion of claim 1.

15. A kit for detecting a CD20 protein or an extracellular domain of a CD20 protein in a biological sample, comprising the antibody or antigen binding portion of claim 1 and at least one reagent for the detection of the antibody or antigen binding portion.

16. The isolated antibody or antigen binding portion of claim 1, wherein the antibody or antigen binding portion binds to the canine CD20 cyclic peptide at a higher affinity than a linear peptide having the sequence of SEQ ID NO: 21.

17. The cell of claim 8, wherein the cell is an immune cell, a T-cell or natural killer (NK) cell.

18. The chimeric antigen receptor of claim 9, wherein the chimeric antigen receptor comprises a CD8 leader sequence, a CD28 costimulatory domain, a CD3-chain, a 4-1BBL costimulatory domain, a PD1-DNR domain, a CD34 domain, or any combination thereof.

19. The autoimmune disease of claim 13, wherein the autoimmune disease is selected from the group consisting of rheumatoid arthritis, systemic lupus erythematosus (SLE), Sjogren's syndrome, vasculitis, multiple sclerosis, Graves' disease, idiopathic thrombocytopenia, dermatomyositis, immune mediated thrombocytopenia, polymyocytosis, pemphigus, immune mediated hemolytic anemia and bullous pemphigoid.

20. The biological sample of claim 14, wherein the biological sample is a biopsy, tissue, blood, serum, plasma, or lymphatic fluid sample; or comprises cells that express a CD20 protein or a fragment thereof or is a cell lysate prepared from cells that express a CD20 protein or a fragment thereof; or comprises B cells or a B cell lysate.

* * * * *